United States Patent
Dietrich et al.

(10) Patent No.: US 11,390,891 B2
(45) Date of Patent: Jul. 19, 2022

(54) RECOMBINANT HOST CELLS AND METHODS FOR THE PRODUCTION OF D-LACTIC ACID

(71) Applicant: LYGOS, INC., Berkeley, CA (US)

(72) Inventors: Jeffrey A. Dietrich, Berkeley, CA (US); Mario Ouellet, Berkeley, CA (US); Andrew Jonathan Conley, Berkeley, CA (US)

(73) Assignee: Lygos, Inc., Berkeley, CA (US)

( * ) Notice: Subject to any disclaimer, the term of this patent is extended or adjusted under 35 U.S.C. 154(b) by 0 days.

(21) Appl. No.: 17/046,703

(22) PCT Filed: Apr. 11, 2019

(86) PCT No.: PCT/US2019/026960
§ 371 (c)(1),
(2) Date: Oct. 9, 2020

(87) PCT Pub. No.: WO2019/200079
PCT Pub. Date: Oct. 17, 2019

(65) Prior Publication Data
US 2021/0108236 A1   Apr. 15, 2021

Related U.S. Application Data

(60) Provisional application No. 62/657,432, filed on Apr. 13, 2018, provisional application No. 62/809,156, filed on Feb. 22, 2019, provisional application No. 62/809,196, filed on Feb. 22, 2019.

(51) Int. Cl.
*C12P 7/56* (2006.01)
*C12N 15/81* (2006.01)
*C12N 9/04* (2006.01)
*C12N 1/16* (2006.01)
*C12N 1/14* (2006.01)
*C12N 1/20* (2006.01)

(52) U.S. Cl.
CPC .......... *C12P 7/56* (2013.01); *C12N 1/14* (2013.01); *C12N 1/16* (2013.01); *C12N 1/20* (2013.01); *C12N 9/0006* (2013.01); *C12N 15/81* (2013.01); *C12N 15/815* (2013.01); *C12Y 101/01027* (2013.01); *C12Y 101/02004* (2013.01)

(58) Field of Classification Search
None
See application file for complete search history.

(56) References Cited

U.S. PATENT DOCUMENTS

| | | | |
|---|---|---|---|
| 2009/0275095 A1* | 11/2009 | Ishida | C12P 7/56 435/139 |
| 2011/0039327 A1* | 2/2011 | Winkler | A23L 31/00 435/254.21 |
| 2013/0302866 A1* | 11/2013 | Finley | C12Y 604/01001 435/145 |
| 2015/0232894 A1 | 8/2015 | Kim et al. | |
| 2017/0349920 A1 | 12/2017 | Sohn et al. | |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Alignment of SEQ ID No. 4 of US20090275095 to SEQ ID No. 1 (Year: 2009).*
Bornscheuer et al. Curr Protoc Protein Sci. Nov. 2011;Chapter 26:Unit26.7. (Year: 2011).*
International Search Report and Written Opinion issued in PCT/US2019/026960, dated Jul. 15, 2019.

* cited by examiner

*Primary Examiner* — Christian L Fronda
(74) *Attorney, Agent, or Firm* — Faegre Drinker Biddle & Reath LLP

(57) ABSTRACT

Methods and materials related to producing D-lactic acid are disclosed. Specifically, isolated synthetic or natural nucleic acids, synthetic or natural polypeptides, host cells, and methods and materials for producing D-lactic acid by direct fermentation from carbon sources are disclosed, along with methods of preparing D-lactic acid polymers.

15 Claims, No Drawings
Specification includes a Sequence Listing.

RECOMBINANT HOST CELLS AND METHODS FOR THE PRODUCTION OF D-LACTIC ACID

CROSS-REFERENCE TO RELATED APPLICATION

This application claims the benefit of priority under 35 U.S.C. 119(e) and Article 2 of the Paris Convention for the Protection of Industrial Property (1883) to U.S. Provisional Application No. 62/657,432, filed Apr. 13, 2018, U.S. Provisional Application No. 62/809,156, filed Feb. 22, 2019, and U.S. Provisional Application No. 62/809,196, filed Feb. 22, 2019, the contents of which are incorporated herein by reference.

REFERENCE TO SEQUENCE LISTING

This application contains a Sequence Listing submitted via EFS-web in computer readable form, which is hereby incorporated by reference in its entirety for all purposes. The ASCII copy, created on Apr. 11, 2019, is named LYGOS_0013_01_WO_ST25 and is 104 KB in size.

FIELD

This disclosure relates to methods and materials for the production of D-lactic acid including, for example, isolated synthetic and natural nucleic acids, synthetic and natural polypeptides, host cells, and methods and materials for producing D-lactic acid by direct fermentation from carbon sources, along with methods of preparing D-lactic acid polymers.

BACKGROUND

Lactic acid has been used historically for food acidulation and preservation. Recently, the global market for lactic acid has increased due to demand for biodegradable plastics in food packaging, medical devices, and personal care products, all of which comprise lactic acid-based polymers such as polylactic acid (PLA), which is predominantly manufactured from L-lactic acid. PLA can be a competitive replacement for petrochemical-derived plastics that employ depleting feedstocks and hazardous, energy-intensive manufacturing processes.

Current PLA polymers are used for single-use products, such as disposable, non-microwaveable food packaging. However, high-temperature PLA can replace the durable petrochemical plastics polypropylene and polystyrene, which opens up new market applications.

D-lactic acid can be manufactured by microbial fermentation. However, existing materials and methods to produce high purity D-lactic acid by microbial fermentation are incapable of satisfying performance metrics at commercial scale (see, for example, Okano et al, Appl Microbiol Biotechnol (2010) 85:413-423). Existing bacterial fermentations may also require complex and expensive nutrients in fermentation media, prohibiting applications at commercial scale. In the yeast *Saccharomyces cerevisiae*, efforts may be impaired by the inability of engineered host cells to grow, which lead to low D-lactic acid yields and productivities. There is a need to produce D-lactic acid in high yield, in some instances with acid tolerant organisms and with reduced byproduct formation from bio-based, renewable sources.

SUMMARY

The long-term economic and environmental concerns associated with the petrochemical industry have provided the impetus for the development and use of renewable chemicals (such as bio-based chemicals) that can be utilized instead of petroleum-derived chemicals. Such renewable chemicals include lactic acids, which are important building block chemicals that are used in a wide range of industries and applications, including polypropylene and polystyrene. Recent development of biorefining processes which convert renewable feedstocks into bio-based lactic acid can provide the necessary reagents for producing bio-based products. As a more sustainable alternative to petrochemically-derived products, there is a great need for bio-based D-lactic acid and polymers made therefrom, such as bio-based polypropylene and polystyrene, as well as methods of making these renewable compositions.

The present disclosure provides materials and methods for efficient production of high purity and high yield D-lactic acid by microbial fermentation. The materials and methods described herein enable high fermentation yields, titers, and/or productivities of D-lactic acid. The materials and methods described herein comprise a renewable and low-cost starting material and an environmentally-benign biosynthetic process.

In one aspect, the present disclosure provides a recombinant cell comprising a heterologous nucleic acid encoding a D-lactate dehydrogenase. In some embodiments, the D-lactate dehydrogenase is selected from a sequence having at least 60% amino acid identity with SEQ ID NO: 1, SEQ ID NO: 2, SEQ ID NO: 3, SEQ ID NO: 4, SEQ ID NO: 5, SEQ ID NO: 6, SEQ ID NO: 17, SEQ ID NO: 18, SEQ ID NO: 19, SEQ ID NO: 20, SEQ ID NO: 21, SEQ ID NO: 22 or SEQ ID NO: 23. In some embodiments, the heterologous nucleic acid is expressed in sufficient amount to produce D-lactic acid. In some embodiments, the recombinant cell is a yeast cell. In some embodiments, the recombinant cell is a prokaryotic cell.

In some embodiments, the present disclosure provides a recombinant cell further comprising one or more additional heterologous nucleic acids encoding one or more proteins selected from organic acid transporters and redox cofactor biogenesis proteins. In some embodiments, the additional heterologous nucleic acid encodes an organic acid transporter having at least 90% amino acid identity with a sequence selected from SEQ ID NO: 7, SEQ ID NO: 8, SEQ ID NO: 9, and SEQ ID NO: 10. In some embodiments, the present disclosure provides a recombinant cell further comprising a genetic disruption of one or more genes encoding pyruvate decarboxylase, a protein subunit of the pyruvate dehydrogenase complex, glycerol-3-phosphate dehydrogenase, NAD(P)H dehydrogenase, or combinations thereof. In some embodiments, the genetic disruption is in a pyruvate decarboxylase gene having at least 90% amino acid identity with a sequence selected from SEQ ID NO: 11, SEQ ID NO: 12, SEQ ID NO: 13, and SEQ ID NO: 14. In other embodiments, the genetic disruption is in a glycerol-3-phosphate dehydrogenase gene having at least 90% amino acid identity with SEQ ID NO: 15. In other embodiments, the genetic disruption is in an NAD(P)H dehydrogenase gene having at least 90% amino acid identity with SEQ ID NO: 16.

In another aspect, provided herein is a method for producing D-lactic acid that comprises culturing the recombinant cells of this disclosure under fermentation conditions suitable to produce D-lactic acid, or a salt thereof. In some embodiments, the method further comprises isolating the D-lactic acid, or salt thereof.

In another aspect, provided herein is a method for producing a lactic acid polymer that comprises culturing the recombinant cells of this disclosure under fermentation conditions suitable to produce D-lactic acid, or a salt thereof. In some embodiments, the method comprises isolating the D-lactic acid or salt thereof. In some embodiments, the method comprises optionally converting the D-lactic acid or salt thereof to a D-lactic acid derivative. In some embodiments, the method comprises producing a lactic acid polymer using the isolated D-lactic acid, salt thereof, or D-lactic acid derivative.

DETAILED DESCRIPTION

The present disclosure provides materials and methods for the biological production and purification of D-lactic acid. This Detailed Description contains parts identified by headings merely for a reader's convenience, and, as will be apparent to the skilled artisan, disclosure found in any part can be relevant to any other part of this disclosure. The present disclosure is not limited to particular nucleic acids, expression vectors, enzymes, biosynthetic pathways, host microorganisms, processes, or enantiomers, as such may vary. Because lactic acid encompasses two different enantiomers—D-lactic acid (synonymous with R-lactic acid and (+)-lactic acid) and L-lactic acid (synonymous with S-lactic acid and (−)-lactic acid)—many materials, methods, and embodiments disclosed that relate to D-lactic acid also pertain to L-lactic acid. In addition, many modifications may be made to adapt a particular situation, material, composition of matter, process, process steps or process flows, in accordance with this disclosure. All such modifications are within the scope of the claims appended hereto.

Definitions

As used herein, the following terms have the following meanings.

The term "heterologous" as used herein refers to a material that is non-native to a cell. In one embodiment, a nucleic acid is heterologous to a cell, and so is a "heterologous nucleic acid" with respect to that cell, if at least one of the following is true: 1) the nucleic acid is not naturally found in that cell (that is, it is an "exogenous" nucleic acid); 2) the nucleic acid is naturally found in a given host cell (that is, "endogenous to"), but the nucleic acid or the RNA or protein resulting from transcription and translation of this nucleic acid is produced or present in the host cell in an unnatural (for example, greater or lesser than naturally present) amount; 3) the nucleic acid comprises a nucleotide sequence that encodes a protein endogenous to a host cell but differs in sequence from the endogenous nucleotide sequence that encodes that same protein (having the same or substantially the same amino acid sequence), typically resulting in the protein being produced in a greater amount in the cell, or in the case of an enzyme, producing a mutant version possessing altered (for example, higher or lower or different) activity; and/or 4) the nucleic acid comprises two or more nucleotide sequences that are not found in the same relationship to each other in the cell. In an embodiment, a protein is heterologous to a host cell if it is produced by translation of RNA or the corresponding RNA is produced by transcription of a heterologous nucleic acid. In another embodiment, a protein is heterologous to a host cell if it is a mutated version of an endogenous protein, and the mutation was introduced by genetic engineering.

The terms "homologous," "homology," "identity," "sequence identity" and variations thereof refer to the similarity of a nucleic acid or amino acid sequence, in some embodiments in the context of a coding sequence for a gene or the amino acid sequence of a protein. Homology or identity searches can be employed using a known, or reference, amino acid or coding sequence for a useful protein to identify coding sequences or proteins that have similar sequences and thus are likely to perform the same function as the protein defined by the reference sequence. In one embodiment, such coding sequences or proteins are homologous to the reference sequence. A protein having homology or high sequence identity to a reference protein can be identified, for example and without limitation, by a BLAST (https://blast.ncbi.nlm.nih.gov) search. A protein with high percent homology or sequence identity is highly likely to carry out the identical biochemical reaction as the reference protein. In an embodiment, two enzymes having greater than 60% homology or sequence identity will carry out identical biochemical reactions, and the higher the homology or sequence identity, i.e., 65%, 70%, 75%, 80%, 85%, 90% or greater than 95% homology or sequence identity, the more likely the two proteins have the same or similar function. In another embodiment, a protein with at least 60% homology or sequence identity to its reference protein is defined as homologous to its reference protein.

Generally, homologous proteins share substantial sequence identity. Sets of homologous proteins generally possess one or more specific amino acids that are conserved across all members of the consensus sequence protein class. The percent sequence identity of a protein relative to a consensus sequence is determined by aligning the protein sequence against the consensus sequence. Various sequence alignment algorithms are suitable for aligning a protein with a consensus sequence. See, for example, Needleman, S B, et al., "A general method applicable to the search for similarities in the amino acid sequence of two proteins." Journal of Molecular Biology 48 (3): 443-53 (1970). Following alignment of the protein sequence relative to the consensus sequence, the percentage of positions where the protein possesses an amino acid described by the same position in the consensus sequence determines the percent sequence identity or homology to the consensus sequence. When a degenerate amino acid is present in a consensus sequence, any of the amino acids described by the degenerate amino acid may be present in the protein at the aligned position for the protein to be identical to the consensus sequence at the aligned position. In one embodiment, when it is not possible to distinguish between two closely related amino acids, the following one-letter symbols may be used—"B" refers to aspartic acid or asparagine; "Z" refers to glutamine or glutamic acid; "J" refers to leucine or isoleucine; and "X" or "+" refers to any amino acid. A dash (-) in a consensus sequence indicates that there is no amino acid at the specified position.

In addition to identification of useful enzymes by percent homology or sequence identity with a given consensus sequence, in one embodiment enzymes useful in the compositions and methods provided herein can also be identified by the number of highly conserved amino acid residues relative to a consensus sequence. For the consensus sequence provided herein, a number of highly conserved amino acid residues are described. In this embodiment, enzymes useful in the compositions and methods provided herein have a substantial number, and sometimes all, of the highly conserved amino acids at positions aligning with the indicated residues in the consensus sequence. As with percent homology or sequence identity, the presence or absence of these highly conserved amino acids can be determined by alignment of the query protein sequence relative to the consensus sequence, as described above.

The terms "expression vector" or "vector" refer to a nucleic acid and/or a composition comprising a nucleic acid that can be introduced into a host cell, for example, by transduction, transformation, or infection, such that the cell then produces (i.e., expresses) nucleic acids and/or proteins contained in or encoded by the sequence of the vector, which in some embodiments are nucleic acids and/or proteins other than those native to the cell, or in a manner not native to the cell. Thus, an "expression vector" contains nucleic acids to be expressed by the host cell. Optionally, the expression vector can be contained in materials to aid in achieving entry of the nucleic acids into the host cell, such as the materials associated with a virus, liposome, protein coating, or the like. Expression vectors suitable for use in various aspects and embodiments of the present disclosure comprise those into which a nucleic acid sequence can be, or has been, inserted, along with any operational elements. Thus, an expression vector can be introduced into a host cell and replicated therein. In an embodiment, an expression vector that integrates into chromosomal, mitochondrial, or plastid DNA is employed. In another embodiment, an expression vector that replicates extrachromosomally is employed. Typical expression vectors include plasmids, and expression vectors typically contain operational elements for transcription of a nucleic acid in the vector.

The terms "ferment", "fermentative", and "fermentation" are used herein to describe culturing microbes under conditions to produce useful chemicals, including but not limited to conditions under which microbial growth, be it aerobic or anaerobic, occurs.

The terms "host cell", "recombinant host cell," "recombinant cell" and "recombinant host microorganism" are used interchangeably herein to refer to a living cell that can be, or has been, transformed via introduction of an expression vector. A host cell or microorganism as described herein may be a prokaryotic cell (for example, a microorganism of the kingdom Eubacteria) or a eukaryotic cell. A prokaryotic cell lacks a membrane-bound nucleus, while a eukaryotic cell has a membrane-bound nucleus.

The terms "isolated" or "pure" refer to material that is substantially, for example, greater than 50% 75%, 90%, 95%, 98% or 99%, free of components that normally accompany it in its native state, for example, the state in which it is naturally found or the state in which it exists when it is first produced. Additionally, any reference to a "purified" material is intended to refer to an isolated or pure material.

The terms "genetic disruption," "genetic modification," "genetic mutation" and "genetic alteration" are used interchangeably to refer to ways of altering genomic, chromosomal or plasmid-based gene expression. Non-limiting examples of genetic disruptions include gene editing (for example CRISPR/Cas9, zinc finger nucleases, TALEN), RNAi, nucleic acid deletions, nucleic acid insertions, nucleic acid substitutions, nucleic acid mutations, knockouts, premature stop codons, transcriptional promoter modifications, and the like. Genetic disruptions give rise to altered gene expression and or altered protein activity. Altered gene expression encompasses decreased, eliminated and increased gene expression levels. In one embodiment, altered gene expression results in altered protein expression.

As used herein, "recombinant" refers to the alteration of genetic material by human intervention. In some embodiments, recombinant refers to the manipulation of DNA or RNA in a cell or virus or expression vector by molecular biology/recombinant DNA technology methods, for example cloning and recombination. Recombinant can also refer to manipulation of DNA or RNA in a cell or virus by random or directed mutagenesis. A "recombinant" cell or nucleic acid can be described with reference to how it differs from a naturally occurring, wild-type counterpart. In this disclosure, reference to a cell or nucleic acid that has been "engineered" or "modified" and variations of those terms, refers to a recombinant cell or nucleic acid.

The terms "transduce", "transform", "transfect", and variations thereof refer to the introduction of one or more nucleic acids into a cell. In an embodiment, the nucleic acid is stably maintained or replicated by the cell for a sufficient period of time to enable the function(s) or product(s) it encodes to be expressed. Stable maintenance or replication of a nucleic acid may take place either by incorporation of the sequence of nucleic acids into the cellular chromosomal DNA, for example the genome as occurs by chromosomal integration, or by replication extrachromosomally, as occurs with a freely-replicating plasmid. A virus can be stably maintained or replicated when it is "infective": when it transduces a host microorganism, replicates, and spreads progeny expression vectors, for example, viruses, of the same type as the original transducing expression vector to other microorganisms.

"D-lactic acid" means the molecule having the chemical formula $C_3H_6O_3$ and a molecular mass of 90.078 g/mol (CAS No. 10326-41-7). The terms "D-lactic acid", "R-lactic acid", "(−)-lactic acid", "D-(−)-lactic acid", "(2R)-2-hydroxypropanoic acid", "(R)-(−)-lactic acid", "(R)-2-hydroxypropanoic acid", "(R)-2-hydroxypropionic acid", "(R)-lactic acid", "(R)-α-hydroxypropionic acid" all describe the same molecule and are used interchangeably in the present disclosure.

In conditions with pH values higher than the pKa of D-lactic acid (for example, about pH>3.86 when using a base, such as sodium hydroxide), D-lactic acid is deprotonated to the D-lactate anion $C_3H_5O_3$. In this disclosure, "D-lactate anion" is used interchangeably with "D-lactate", "R-lactate", "(−)-lactate", "D-(−)-lactate", "(2R)-2-hydroxypropanoate", "(R)-(−)-lactate", "(R)-2-hydroxypropanoate", "(R)-2-hydroxypropionate", "(R)-lactate" and "(R)-α-hydroxypropionate."

The D-lactate anion is capable of forming an ionic bond with a cation to produce a D-lactate salt. In this disclosure, the term "D-lactate" refers to a variety of D-lactate salt forms and is used interchangeably with "D-lactate salts". Non-limiting examples of D-lactates comprise sodium D-lactate (CAS No. 920-49-0), calcium D-lactate (CAS No. 16127-59-6), and lithium D-lactate (CAS No. 27848-81-3).

D-lactate salts can crystallize in various states of hydration. For example, magnesium D-lactate salt can form hydrated crystals, wherein a single molecule of magnesium D-lactate crystallizes with one, two, three, or more molecules of water. As used herein, "magnesium D-lactate dihydrate" means $Mg(C_3H_5O_3)_2 \cdot (H_2O)_2$ with a molecular mass of 238.47 g/mol, wherein a single molecule of magnesium D-lactate crystallizes with two molecules of water. As used herein, "magnesium D-lactate trihydrate" means $Mg(C_3H_5O_3)_2 \cdot (H_2O)_3$ with a molecular mass of 256.48 g/mol, wherein a single molecule of magnesium D-lactate crystallizes with three molecules of water. Magnesium D-lactate can also form anhydrous crystals; as used herein, "anhydrous magnesium D-lactate" means $Mg(C_3H_5O_3)_2$ with a molecular mass of 202.45 g/mol, which is synonymous with "magnesium D-lactate", and "magnesium D-2-hydroxypropanoate", "magnesium D-2-hydroxypropionate", "magnesium 2-hydroxypropanoate", and "magnesium 2-hydroxypropionate".

In conditions with pH values lower than the pKa of lactic acid (for example, pH<3.86), the lactate anion is protonated to form lactic acid. Herein, "D-lactate" is also used interchangeably with "D-lactic acid".

The D-lactic acid, D-lactate salts and D-lactate esters of the present disclosure are synthesized from biologically produced organic components by a fermenting microorganism. For example, D-lactic acid, D-lactate salts, or their precursor(s) are synthesized from the fermentation of sugars by recombinant host cells provided by the present disclosure.

The prefix "bio-" or the adjective "bio-based" may be used to distinguish these biologically-produced D-lactic acid and D-lactate salts from those that are derived from petroleum feedstocks. As used herein, "D-lactic acid" is defined as "bio-based D-lactic acid", and "D-lactate salt" is defined as "bio-based D-lactate salt". The terms "bio-based" or "non-petrochemically derived" or "renewable" as used herein refer to an organic compound that is synthesized from biologically produced organic components by fermenting a microorganism. For example, an acid which was itself synthesized from glucose (for example, derived from cornstarch) by a genetically engineered microorganism is bio-based or non-petrochemically derived. As used herein, a compound of renewable or non-petrochemical origin comprises carbon atoms that have a non-petrochemical origin. These compounds are distinguished from wholly petroleum-derived compounds or those entirely of fossil origin. Such compounds have a $^{14}C$ amount substantially higher than zero, such as about 1 parts per trillion or more, because they are derived from photosynthesis-based starting material, such as for example, glucose or another feedstock used in producing such a compound.

The redox cofactor nicotinamide adenine dinucleotide, NAD, comes in two forms—phosphorylated and un-phosphorylated. In this disclosure, the terms "NAD(P)" or "NADP" refer to both phosphorylated (NADP) and un-phosphorylated (NAD) forms and encompasses oxidized versions ($NAD^+$ and $NADP^+$) and reduced versions (NADH and NADPH) of both forms. The term "$NAD(P)^+$" refers to the oxidized versions of phosphorylated and un-phosphorylated NAD, i.e., $NAD^+$ and $NADP^+$. Similarly, the term "NAD(P)H" refers to the reduced versions of phosphorylated and un-phosphorylated NAD, i.e., NADH and NADPH. When NAD(P)H is used to describe the redox cofactor in an enzyme catalyzed reaction, it indicates that NADH and/or NADPH is used. Similarly, when $NAD(P)^+$ is the notation used, it indicates that $NAD^+$ and/or $NADP^+$ is used. While many proteins may bind either a phosphorylated or un-phosphorylated cofactor, there are redox cofactor promiscuous proteins, natural or engineered, that are indiscriminate; in these cases, the protein may use either NADH and/or NADPH. In some embodiments, enzymes that preferentially utilize either NAD(P) or NAD may carry out the same catalytic reaction when bound to either form.

Various values for temperatures, titers, yields, oxygen uptake rate (OUR), and pH are recited in the description and in the claims. In some embodiments, these values are not exact and can be approximated to the rightmost/last/least significant figure. For example, a temperature range of from about 30° C. to about 42° C. covers the range 25° C. to 44° C.

D-lactic acid and L-lactic acid are enantiomers (also known as optical isomers); they are molecules that share the same molecular weight of 90.078 g/mol and are non-superimposable mirror images of each other, analogous to one's left and right hands being the same and not superimposable by simple reorientation around an axis. The D- or (+)-enantiomer rotates polarized light clockwise (to the right) while the L- or (−)-enantiomer rotates polarized light counterclockwise (to the left). Solutions with a mixture of both enantiomers are racemic mixtures and are typically produced by microbes that naturally produce lactic acid. Lactic acid enantiomers are prohibitively expensive to separate out at commercial scale. High enantiomeric purity (i.e., 99.5% and above) enables one to titrate specific physical properties of PLA blends; enantiomer-exclusive precursors, catalysts and/or enzymes will typically be present for a biosynthetic pathway to give rise to an enantiomerically/optically pure product (i.e., a lactic acid solution that comprises only one of the two enantiomers at >99.5% purity).

In a first aspect, this disclosure provides recombinant host cells capable of producing D-lactic acid comprising one or more heterologous nucleic acids that encode the D-lactic acid biosynthetic pathway, wherein the pathway enzymes comprise a D-lactate dehydrogenase (DLDH). In some embodiments, the recombinant host cells comprise heterologous nucleic acids encoding a DLDH with at least 60% homology to SEQ ID NO: 1, SEQ ID NO: 2, SEQ ID NO: 3, SEQ ID NO: 4, SEQ ID NO: 5, SEQ ID NO: 6, SEQ ID NO: 17, SEQ ID NO: 18, SEQ ID NO: 19, SEQ ID NO: 20, SEQ ID NO: 21, SEQ ID NO: 22, and SEQ ID NO: 23.

In some embodiments, the DLDH comprises the residues GXGXXG, where X refers to any amino acid, and wherein 1-3 amino acid residues 18-20 residues downstream to the GXGXXG residue are mutated, in some embodiments to a neutral amino acid, as compared to a wild type sequence.

In some embodiments, the DLDH comprises the residues GXGXXG, where X refers to any amino acid, and wherein a negatively charged amino acid, such as D, 18-20 residues downstream to the GXGXXG residue is changed to a neutral amino acid, as compared to a wild type sequence.

In some embodiments, the recombinant host cell is a yeast cell. In certain embodiments, the yeast cell belongs to the *Issatchenkia orientalis/Pichia fermentans* clade. In some embodiments, the yeast cell belongs to the genus *Pichia*, *Issatchenkia* or *Candida*. In some embodiments, the yeast cell is *Pichia kudriavzevii*. In some embodiments, the yeast cell belongs to the *Saccharomyces* clade. In some embodiments, the yeast cell is *Saccharomyces cerevisiae*. In other embodiments, the recombinant host cell is a prokaryotic cell. In some embodiments, the prokaryotic cell belongs to the genus *Escherichia*, *Corynebacterium*, *Bacillus*, or *Lactococcus*. In some embodiments, the prokaryotic cell is *Escherichia coli*, *Corynebacterium glutamicum*, *Bacillus subtilis*, or *Lactococcus lactis*.

In a second aspect, this disclosure provides recombinant host cells that further comprise one or more heterologous nucleic acids encoding one or more proteins that function in redox cofactor biogenesis and/or organic acid transport. In some embodiments, the one or more proteins comprise a protein with at least 60% homology with SEQ ID NO: 7, SEQ ID NO: 8, SEQ ID NO: 9, SEQ ID NO: 10, or any combination thereof.

In a third aspect, this disclosure provides recombinant host cells that further comprise a genetic disruption of one or more genes wherein the one or more genes encodes pyruvate decarboxylase, a protein subunit of the pyruvate dehydrogenase complex, glycerol-3-phosphate dehydrogenase, NAD(P)H dehydrogenase, or any combination thereof. In some embodiments, the one or more genes has at least 60% homology to SEQ ID NO: 11, SEQ ID NO: 12, SEQ ID NO: 13, SEQ ID NO: 14, SEQ ID NO: 15, or SEQ ID NO: 16, or any combination thereof. In some of these embodiments, the recombinant host cells produce less than 5 g/L of ethanol, 5 g/L of pyruvate, 5 g/L of acetate, 5 g/L of glycerol, or any combination thereof, in the fermentation broth.

In another embodiment, the recombinant host cells provided herein overexpress an engineered PDC gene (for example, one or more of PDC1, PDC5, or PDC6) that contains a temperature-sensitive intein. At low temperature (for example, at about 30° C.) the PDC protein is active, whereas at higher temperatures (for example, at about 37-42° C.) the PDC protein is no longer functionally expressed and the host cells exhibit reduced pyruvate decarboxylase activity and increased lactic acid production.

In another embodiment, the recombinant host cells provided herein comprise a knockout of mitochondrial external NADH dehydrogenase (EC 1.6.99.3), which is NDE1. In another embodiment, the recombinant host cells provided herein comprise a knockout of mitochondrial external NADH dehydrogenase, which is NDE2. In another embodiment, the recombinant host cells provided herein comprise a knockout of NDE1, and NDE2. NADH dehydrogenase is responsible for a substantial majority of NADH re-oxidation activity in the cytosol under aerobic conditions. The knockout enables efficient lactic acid production under aerobic conditions by substantially eliminating a major source of native NADH re-oxidation activity in the cytosol. Thus, LDH activity becomes the major route via which the cell re-oxidizes NADH under aerobic conditions in the absence of growth.

In another embodiment, the recombinant host cells provided herein overexpress an engineered NADH dehydrogenase gene (for example, NED1 and/or NED2) that contains a temperature-sensitive intein. At low temperature (for example, at about 30° C.) the NADH dehydrogenase protein is active, whereas at higher temperatures (for example, at about 37-42° C.) the NADH dehydrogenase protein is no longer functionally expressed and the host cells exhibit reduced NADH dehydrogenase activity and increased lactic acid production.

In another embodiment, the recombinant host cells provided herein comprise a knockout of a PDA1 gene, which is a subunit of pyruvate dehydrogenase. Pyruvate dehydrogenase is responsible for converting pyruvate to acetyl-CoA in the mitochondria. The knockout reduces formation of acetyl-CoA derived products and increases lactic acid production by increasing pyruvate substrate availability for LDH in the cytosol.

In another embodiment, the recombinant host cells provided herein overexpress an engineered PDA1 gene that contains a temperature-sensitive intein. At low temperature (for example, at about 30° C.) the PDA1 protein is active and it enables good conversion of pyruvate to acetyl-CoA in the mitochondria. The acetyl-CoA is used for growth, ATP formation, and, more general cellular activities. At higher temperatures (for example, at about 37-42° C.) the PDA1 protein is no longer functionally expressed and the host cells exhibit reduced PDA1 activity. In this manner, a two-phase fermentation with respect to temperature is enabled. Low temperature is thus beneficial for growth and high temperature for lactic acid production. Therefore, in certain embodiments, temperature and uracil are used to efficiently switch from growth to lactic acid production phase.

In another embodiment, the recombinant host cells provided herein comprise a ZWF1 knockout. ZWF1 is a cytoplasmic glucose-6-phosphate dehydrogenase (EC 1.1.1.49). These knockouts decrease carbon flux through the pentose phosphate pathway, thereby decreasing NADPH production and increasing NADH production during the conversion of glucose to pyruvate via glycolytic enzymes. The increased amount of NADH increases lactic acid production (yield, titer, and/or productivity) and decrease pyruvate accumulation. In another embodiment, the recombinant host cells provided herein overexpress an engineered ZWF1 gene that contains a temperature-sensitive intein. At low temperature (for example, at about 30° C.) the ZWF1 protein is active and it enables pyruvate accumulation, and subsequently conversion of pyruvate to acetyl-CoA in the mitochondria. At higher temperatures (for example, at about 37-42° C.) the ZWF1 protein is no longer functionally expressed and the host cells exhibit reduced ZWF1 activity and increased lactic acid production.

In another embodiment, the recombinant host cells provided herein are glycerol-3-phosphate dehydrogenase (EC 1.1.1.8), GPD1 knockouts. These knockouts decrease glycerol formation. Glycerol is a major byproduct, which reduces lactic acid production; additionally, this knockout increases the amount of NADH available for lactic acid production, resulting in increased lactic acid production and decreased pyruvate accumulation. In another embodiment, the recombinant host cells provided herein overexpress an engineered GPD1 gene that contains a temperature-sensitive intein. At low temperature (for example, at about 30° C.) the GPD1 protein is active, whereas at higher temperatures (for example, at about 37-42° C.) the GPD1 protein is no longer functionally expressed and the host cells exhibit reduced GPD1 activity and increased lactic acid production.

In another embodiment, the recombinant host cells provided herein comprise an NAD kinase (NADK; EC 2.7.1.23) knockout. In one embodiment, the NADK knockout is a YEF1 knockout. In another embodiment, the NADK knockout is a POS5 knockout. These knockouts decrease oxidation of cytosolic NADH and NADPH, thereby increasing the cytosolic availability of NAD(P)H for re-oxidation by the LDH and decrease pyruvate accumulation and increase lactate production. In another embodiment, the recombinant host cells provided herein overexpress an engineered NADK gene (for example, a YEF1 and/or a POS5) that contains a temperature-sensitive intein. At low temperature (for example, at about 30° C.) the NADK protein is active, whereas at higher temperatures (for example, at about 37-42° C.) the NADK protein is no longer functionally expressed and the host cells exhibit reduced NADK activity and increased lactic acid production.

In another embodiment, the recombinant host cells provided herein comprise a dihydrolipoamide dehydrogenase, DLD1B, knockout. A DLD1B knockout decreases native lactic acid catabolism and may increase lactate production. In another embodiment, the recombinant host cells provided herein overexpress an engineered DLD1B gene that contains a temperature-sensitive intein. At low temperature (for example, at about 30° C.) the DLD1B protein is active, whereas at higher temperatures (for example, at about 37-42° C.) the DLD1B protein is no longer functionally expressed and the host cells exhibit reduced DLD1B activity and increased lactic acid production.

In a fourth aspect, this disclosure provides a method for the production of D-lactic acid that comprises culturing the recombinant host cells of this disclosure for a sufficient period of time to produce D-lactic acid. In some embodiments, the method further comprises an oxygen transfer rate greater than 5 mmol/L/hr. In some embodiments, the method further comprises an operational temperature of between about 25° C. and about 45° C. In some embodiments, the method further comprises a final fermentation broth pH of between pH 2-5. In some embodiments, the method further comprises providing at least 100 g/L glucose to the recombinant host cell and producing a D-lactic acid yield of at least 25%. In some embodiments, the method further comprises production of D-lactic acid with enantiomeric purity of at least 99.5%.

In a fifth aspect, this disclosure provides a method for the recovery of D-lactic acid and D-lactate salts from the fermentation broth.

In another aspect, provided herein is a method of recovering at least one of D-lactic acid, a salt thereof, or a derivative thereof, from fermentation broth.

In yet another aspect, provided herein is a method for producing a lactic acid polymer comprising: culturing the recombinant host cell as disclosed herein under fermentation conditions for a sufficient period of time to produce D-lactic acid, or a salt thereof, optionally converting the D-lactic acid or salt thereof to a D-lactic acid derivative; recovering at least one of D-lactic acid, a salt thereof, or a derivative thereof, from the fermentation broth; and producing a lactic acid polymer using the recovered D-lactic acid, a salt thereof, or a derivative thereof as at least one polymerization material.

Methods for converting L-lactic acid to poly(-L-lactide), and subsequently, PLLA, are known to practitioners in the art, and practitioners in the art are equipped to use and/or modify said methods to convert D-lactic acid to poly(-D-lactide), and subsequently, PDLA. Similarly, practitioners in the art are equipped to use and/or modify said methods to convert L-lactic and D-lactic acid to poly(-D,L-lactide), and subsequently, a blended PLA, with varying D- to L-lactic acid ratios towards desired chemical and physical properties.

In another aspect, the D-lactic acid provided herein has non-petrochemical based carbons or has a $^{14}C$ amount substantially higher than zero, such as about 1 parts per trillion or more. Such non-petrochemical based (or biobased or renewable) D-lactic acid has a $^{14}C$ amount substantially higher than zero, such as about 1 parts per trillion or more, because they are derived from photosynthesis based starting material.

Recombinant Host Cells for Production of D-Lactic Acid
Host Cells

The present disclosure provides recombinant host cells engineered to produce D-lactic acid, wherein the recombinant host cells comprise one or more heterologous nucleic acids encoding one or more D-lactic acid pathway enzymes. In particular embodiments, the recombinant host cells further comprise disruptions or deletions of endogenous nucleic acids that improve yields, titers and/or productivities of D-lactic acid. In some embodiments, the recombinant host cells are capable of producing D-lactic acid under aerobic conditions. In some embodiments, the recombinant host cells are capable of producing D-lactic acid under substantially anaerobic conditions. The recombinant host cells produce D-lactic acid at increased titers, yields and productivities as compared to a parental host cell that does not comprise said heterologous nucleic acids.

In some embodiments, the recombinant host cells further comprise one or more heterologous nucleic acids encoding one or more ancillary gene products (i.e., gene products other than the product pathway enzymes) that improve yields, titers and/or productivities of D-lactic acid. In particular embodiments, the recombinant host cells further comprise disruptions or deletions of endogenous nucleic acids that improve yields, titers and/or productivities of D-lactic acid. In some embodiments, the recombinant host cells are capable of producing D-lactic acid under aerobic conditions. In some embodiments, the recombinant host cells are capable of producing D-lactic acid under substantially anaerobic conditions. In one embodiment, the recombinant host cells produce one or more ancillary gene products at increased titers, yields and productivities as compared to a parental host cell that does not comprise said heterologous nucleic acids.

Any suitable host cell may be used in practice of the methods of the present disclosure, and in some examples, host cells useful in the compositions and methods provided herein comprise archaeal, prokaryotic, or eukaryotic cells. In an embodiment of the present disclosure, the recombinant host cell is a prokaryotic cell. In an embodiment of the present disclosure, the recombinant host cell is a eukaryotic cell. In an embodiment of the present disclosure, the recombinant host cell is a *Pichia kudriavzevii* (*P. kudriavrevii*) strain. Methods of construction and genotypes of these recombinant host cells are described herein.

Yeast Cells

In an embodiment of the present disclosure, the recombinant host cell is a yeast cell. Yeast cells are excellent host cells for construction of recombinant metabolic pathways comprising heterologous enzymes catalyzing production of small-molecule products. There are established molecular biology techniques and nucleic acids encoding genetic elements necessary for construction of yeast expression vectors, including, but not limited to, promoters, origins of replication, antibiotic resistance markers, auxotrophic markers, terminators, and the like. Second, techniques for integration/insertion of nucleic acids into the yeast chromosome by homologous recombination are well established. Yeast also offers a number of advantages as an industrial fermentation host. Yeast cells can generally tolerate high concentrations of organic acids and maintain cell viability at low pH and can grow under both aerobic and anaerobic culture conditions, and there are established fermentation broths and fermentation protocols. This characteristic results in efficient product biosynthesis when the host cell is supplied with a carbohydrate carbon source.

In various embodiments, yeast cells useful in the methods of the present disclosure comprise yeasts of the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella,*

*Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis,* and *Zygozyma,* among others.

In various embodiments, the yeast cell is of a species selected from the non-limiting group comprising *Candida albicans, Candida ethanolica, Candida guilliermondii, Candida krusei, Candida lipolytica, Candida methanosorbosa, Candida sonorensis, Candida tropicalis, Candida utiis, Cryptococcus curvatus, Hanseumla polymorpha, Issatchenkia orientalis, Kiyveromyces lactis, Kluyveromyces marxianus, Kluyveromyces thermotolerans, Komagataella pastoris, Lipomyces starkeyi, Pichia angusta, Pichia deserticola, Pichia galeiformis, Pichia kodamae, Pichia kudriavzevii* (*P. kudriavzevii*)*, Pichia membranaefaciens, Pichia methanolica, Pichia pastoris, Pichia salicaria, Pichia stipitis, Pichia thermotolerans, Pichia trehalophila, Rhodosporidium toruloides, Rhodotorula glutinis, Rhodotorula graminis, Saccharomyces bayanus, Saccharomyces boulardi, Saccharomyces cerevisiae* (*S. cerevisiae*)*, Saccharomyces kluyveri. Schizosaccharomyces pombe* (*S. pombe*) and *Yarrowia lipolytica.*

The Crabtree phenomenon refers to the capability of yeast cells to convert glucose to alcohol in the presence of high sugar concentrations and oxygen instead of producing biomass via the tricarboxylic acid (TCA) cycle. Yeast cells produce alcohol to prevent growth of competing microorganisms in high sugar environments, which yeast cells can utilize later on when the sugars are depleted Many yeast can typically use two pathways to produce ATP from sugars: the first involves the conversion of sugars (via pyruvate) to carbon dioxide via the TCA cycle, and the second involves the conversion of sugars (via pyruvate) to ethanol. Yeast cells that display a Crabtree effect (known as Crabtree-positive yeast cells) are able to simultaneously use both pathways. Yeast cells that do not display a Crabtree effect (known as Crabtree-negative yeast cells) only convert pyruvate to ethanol when oxygen is absent. In some embodiments of the present disclosure, the host cell is a Crabtree-positive yeast cell. In other embodiments, the host cell is a Crabtree-negative yeast cell. In certain embodiments, the host cell displays a phenotype along a continuum of traits between Crabtree-positive and Crabtree-negative and is thus neither exclusively a Crabtree-positive yeast cell nor Crabtree negative yeast cell. It is advantageous to use a Crabtree-negative yeast or a yeast with perceptible Crabtree-negative tendencies or traits to produce D-lactic acid because high glucose concentrations can be maintained during product biosynthesis without ethanol accumulation; ethanol is an undesired byproduct in D-lactic acid production. *P. kudriavzevii* does not produce appreciable amounts of ethanol from pyruvate at high glucose concentrations in the presence of oxygen, and as such is a Crabtree-negative yeast. In some embodiments, the host cell is *P. kudriavzevii.*

In certain embodiments, the recombinant yeast cells provided herein are engineered by the introduction of one or more genetic modifications (including, for example, heterologous nucleic acids encoding enzymes and/or the disruption of native nucleic acids encoding enzymes) into a Crabtree-negative yeast cell. In certain of these embodiments, the host cell belongs to the *Pichia/Issatchenkia/Saturnispora/Dekkera* clade. In certain of these embodiments, the host cell belongs to the genus selected from the group comprising *Pichia, Issatchenkia,* or *Candida.* In certain embodiments, the host cell belongs to the genus *Pichia,* and in some of these embodiments the host cell is *P. kudiavzevii.* Members of the *Pichia/Issatchenkia/Saturnispora/Dekkera* or the *Saccharomyces* clade are identified by analysis of their 26S ribosomal DNA using the methods described by Kurtzman C. P., and Robnett C. J., ("Identification and Phylogeny of Ascomycetous Yeasts from Analysis of Nuclear Large Subunit (26S) Ribosomal DNA Partial Sequences", Atonie van Leeuwenhoek 73(4):331-371; 1998). Kurtzman and Robnett report analysis of approximately 500 ascomycetous yeasts were analyzed for the extent of divergence in the variable D1/D2 domain of the large subunit (26S) ribosomal DNA. Host cells encompassed by a clade exhibit greater sequence identity in the D1/D2 domain of the 26S ribosomal subunit DNA to other host cells within the clade as compared to host cells outside the clade. Therefore, in an embodiment, host cells that are members of a clade (for example, the *Pichia/Issatchenkia/Saturnispora/Dekkera* or *Saccharomyces* clades) can be identified using the methods of Kurtzman and Robnett.

In certain embodiments of the present disclosure, the recombinant host cells are engineered by introduction of one or more genetic modifications into a Crabtree-positive yeast cell. In certain of these embodiments, the host cell belongs to the *Saccharomyces* clade. In certain of these embodiments, the host cell belongs to a genus selected from the group comprising *Saccharomyces, Schizosaccharomyces, Brettanomyces, Torulopsis, Nematospora* and *Nadsonia.* In certain embodiments, the host cell belongs to the genus *Saccharomyces,* and in one of these embodiments the host cell is *S. cerevisiae.*

In one embodiment, use of the term "DLDH" specifically excludes DLDH from the genus *Limulus,* in an embodiment from *Limulus polyphemus,* when the recombinant host utilized herein is yeast.

Eukaryotic Cells

In addition to yeast cells, other eukaryotic cells are also suitable for use in accordance with methods of the present disclosure, so long as the engineered host cell is capable of growth and/or product formation. Illustrative examples of eukaryotic host cells provided by the present disclosure include, but are not limited to cells belonging to the genera *Aspergillus, Crypthecodinium, Cunninghamella, Entomophthora, Mortierella, Mucor, Neurospora, Pythium, Schizochytriumm, Thraustochytrium, Trichoderma,* and *Xanthophyllomyces.* Examples of eukaryotic strains include, but are not limited to: *Aspergillus niger, Aspergillus oryzae, Crypthecodinium cohnii, Cunninghamella japonica, Emomophthora coronata, Mortierella alpina, Mucor circinelloides, Neurospora crassa, Pythium ultimum, Schizochytrium limacium, Thraustochytrium aureum, Trichoderma reesei* and *Xanthophyllomyces dendrorhous.*

Archaeal Cells

Archaeal cells are also suitable for use in accordance with methods of the present disclosure, and in an embodiment of the present disclosure, the recombinant host cell is an archaeal cell. Illustrative examples of recombinant archaea host cells provided by the present disclosure include, but are not limited to, cells belonging to the genera: *Aeropyrum, Archaeglobus, Halobacterium, Methanococcus. Methanobacterium, Pyrococcus. Sulfolobus,* and *Thermoplasma.* Examples of archaea strains include, but are not limited to *Archaeoglobus fulgidus, Halobacterium* sp.*, Methanococcus jannaschii, Methanobacterium thermoautotrophicum,*

*Thermoplasma acidophilum, Thermoplasma volcanium, Pyrococcus horikoshii, Pyrococcus abyssi*, and *Aeropyrum pernix*.

Prokaryotic Cells

In an embodiment of the present disclosure, the recombinant host cell is a prokaryotic cell. Prokaryotic cells are suitable host cells for construction of recombinant metabolic pathways comprising heterologous enzymes catalyzing production of small-molecule products. Illustrative examples of recombinant prokaryotic host cells include, but are not limited to, cells belonging to the genera *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Pantoea, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus*, and *Zymomonas*. Examples of prokaryotic strains include, but are not limited to, *Bacillus subtilis (B. subtilis), Brevibacterium ammoniagenes, Bacillus amyloliquefacines, Brevibacterium ammoniagenes, Brevibacterium immariophilum, Clostridium acetobutylicum, Clostridium beigerinckii, Corynebacterium glutamicum (C. glutamicum), Enterobacter sakazakii, Escherichia coli (E. coli), Lactobacillus acidophilus, Lactococcus lactis, Mesorhizobium loti, Pantoea ananatis (P. ananatis), Pseudomonas aeruginosa, Pseudomonas mevaloni, Pseudomonas pudita, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*.

Lactic Acid Pathway Enzymes

Provided herein in certain embodiments are recombinant host cells having at least one active lactic acid pathway from pyruvate to lactate. Recombinant host cells having an active lactic acid pathway as used herein produce one or more active enzymes capable of catalyzing the metabolic reaction in a lactic acid pathway, and therefore are capable of producing lactic acid in measurable yields and/or titers when cultured under suitable conditions. Recombinant host cells having a lactic acid pathway comprise one or more heterologous nucleic acids encoding lactic acid pathway enzyme(s) and are capable of producing lactic acid.

Eleven enzymatic steps are used to produce lactic acid from glucose. The first 10 steps are the endogenous glycolysis pathway that converts glucose to pyruvate. The last and 11$^{th}$ step uses a heterologous lactate dehydrogenase (LDH) enzyme to convert pyruvate to lactic acid. All eleven enzymatic steps take place in the cytosol. The lactic acid pathway described herein produces lactate from glucose with the following balanced, stoichiometric equation:

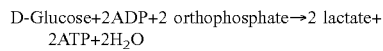

D-Glucose+2ADP+2 orthophosphate→2 lactate+ 2ATP+2H$_2$O

Recombinant host cells may employ combinations of metabolic reactions for biosynthetically producing the compounds of the present disclosure. The biosynthesized compounds produced by the recombinant host cells comprise lactate, lactic acid, and the intermediates, products and/or derivatives of the lactic acid pathway. The biosynthesized compounds can be produced intracellularly and/or secreted into the fermentation medium.

Lactate Dehydrogenase

The lactic acid pathway comprises a lactate dehydrogenase (LDH) that converts one molecule of pyruvate and one molecule of reduced cofactor to one molecule of lactate and one molecule of oxidized cofactor. In various embodiments of the present disclosure, recombinant host cells comprise one or more heterologous nucleic acids encoding a LDH, wherein said recombinant host cells are capable of producing lactic acid. In some embodiments, the recombinant host cells comprise one or more heterologous nucleic acids encoding one, more, or all of the aforementioned LDHs. In many embodiments, the LDH is derived from a prokaryotic source. In many embodiments, the LDH is derived from a eukaryotic source. Any enzyme is suitable for use in accordance with this disclosure so long as the enzyme is capable of catalyzing said LDH reaction.

D-lactate dehydrogenase (DLDH) and L-lactate dehydrogenase (LLDH) are two varieties of LDH that belong to evolutionarily unrelated enzyme families; LLDH belongs to the L-specific dehydrogenase enzyme family, while DLDH belongs to the D-specific dehydrogenase enzyme family.

D-Lactate Dehydrogenase

In the D-lactic acid pathway specifically, a NADH(P)H-dependent DLDH (EC #1.1.1.28) converts one molecule of pyruvate and one molecule of reduced cofactor (for example, NAD(P)H) to one molecule of D-lactate and one molecule of oxidized cofactor (for example, NAD(P)$^+$).

Most known DLDHs utilize NADH as the cofactor, and NADH-dependent DLDH will generally be used when NADH is produced during the recombinant host cell's glycolytic processes in converting glucose to pyruvate. In *P. kudiavzevii* and *S. cerevisiae*, for example, the glyceraldehyde 3-phosphate dehydrogenase (GAPDH) in glycolysis reduces NAD$^+$ to NADH; therefore, in embodiments wherein the GAPDH is NADH-producing, the DLDH is NADH-dependent. In some of these embodiments, the recombinant host cell is the yeast *P. kudriavzevii*.

Similarly, in embodiments wherein NADPH is the cofactor produced in glycolysis, the DLDH is NADPH-dependent. *Kluyveromyces lactis* and *Clostridium acetobutylicum*, for example, natively express NADP+ reducing GAPDH enzymes, thereby generating NADPH in glycolysis; thus, when engineering D-lactic acid production in these strain backgrounds, a NADPH-dependent DLDH used is NADPH-dependent. In other embodiments, the DLDH is engineered to preferentially utilize either NADH or NADPH as cofactors. In yet other embodiments, the DLDH is engineered to utilized both NADH and NADPH as cofactors.

A host cell can be engineered to produce a specific redox cofactor (NADH or NADPH) during glycolysis by changing the GAPDH enzyme expressed. Furthermore, both NADH and NADPH can be generated during glycolysis through concomitant expression of both NADH- and NADPH-dependent GAPDH enzymes. Lastly, NADPH and NADH can be interconverted through expression of a transhydrogenase that catalyzes the interconversion of NADPH and NADH.

In various embodiments of the present disclosure, recombinant host cells comprise one or more heterologous nucleic acids encoding a DLDH wherein said recombinant host cells are capable of producing D-lactic acid. In some embodiments, the recombinant host cells comprise one or more heterologous nucleic acids encoding one, more, or all of the aforementioned DLDHs in Table 1. In many embodiments, the DLDH is derived from a prokaryotic source. In many embodiments, the DLDH is derived from a eukaryotic source. Any enzyme is suitable for use in accordance with this disclosure so long as the enzyme is capable of catalyzing said DLDH reaction.

TABLE 1

Examples of D-lactate dehydrogenase (EC # 1.1.1.28)

| Source organism | UniProt ID |
| --- | --- |
| *Leuconostoc mesenteroides* subsp. *Cremoris* | P51011 |
| *Leuconostoc mesenteroides* subsp. *Mesenteroides* | Q03VC9 |
| *Lactobacillus delbrueckii* subsp. *Bulgaricus* | P26297 |
| *Lactobacillus helveticus* | P30901 |
| *Lactobacillus pentosus* | P26298 |

The aforementioned DLDH-catalyzed step is calculated to thermodynamically favor the conversion of pyruvate to D-lactate. The advantaged thermodynamics of the pathway will help to achieve high D-lactic acid yields, titers and/or productivities. The conversion of glucose to D-lactate using the D-lactic acid pathway described herein has a calculated change in Gibbs free energy of −112.6 kJ/mol (i.e., $\Delta_r G'''$ calculated at 1 mM metabolite concentrations, 25° C., pH 7.0, and 0.1 M ionic strength; conditions typically observed in yeast), a negative value indicative of a strong thermodynamic driving force that pushes the reaction to completion. The conversion of pyruvate to D-lactate using the D-lactic acid pathway described herein has a calculated change in Gibbs free energy of −24.4 kJ/mol, where again the negative value indicates the last reaction step's propensity to proceed in the forward direction.

In certain embodiments, recombinant host cells comprise one or more heterologous nucleic acids encoding one or more of the aforementioned D-lactic acid pathway, wherein the heterologous nucleic acids are expressed in sufficient amounts to produce D-lactate. In various embodiments, recombinant host cells may comprise multiple copies of a single heterologous nucleic acid and/or multiple copies of two or more heterologous nucleic acids. Recombinant host cells comprising multiple heterologous nucleic acids may comprise any number of heterologous nucleic acids.

The present disclosure also provides a consensus sequence (SEQ ID NO: 6) useful in identifying and/or constructing the D-lactic acid pathway suitable for use in accordance with the methods of the present disclosure. In various embodiments, this consensus sequence comprises active site amino acid residues which may contribute to substrate recognition and reaction catalysis, as described below. Thus, an enzyme encompassed by the consensus sequence provided herein has an enzymatic activity that is identical, essentially identical, or at least substantially similar with respect to ability to catalyze the reaction performed by one of the enzymes exemplified herein. For example, a DLDH encompassed by the DLDH consensus sequence provided herein has an enzymatic activity that is identical, or essentially identical, or at least substantially similar with respect to ability to convert one molecule of pyruvate and one molecule of reduced cofactor (for example, NAD(P)H) to one molecule of D-lactate and one molecule of oxidized cofactor (for example, NAD(P)⁺). Such a protein can be used in a host cell of the present disclosure.

In many embodiments, the DLDH is derived from a bacterial source. In many of these embodiments, the DLDH is derived from a host cell belonging to a genus selected from the group comprising *Aquifex, Bacillus, Enterococcus, Escherichia, Eubacterium, Fusobacterium, Klebsiella, Lactobacillus, Leuconostoc, Mycoplasma, Neisseria, Oenococcus, Pediococcus, Pseudomonas, Rhodopseudomonas, Selenomonas, Sporolactobacillus, Staphylococcus, Streptococcus, Thermodesulfatator*, and *Weisella*. Non-limiting examples of bacterial DLDH comprise *Aquifex aeolicus* UniProt ID: O66939, *Bacillus coagulans* UniProt ID: F8RPR8, *Fusobacterium nucleatum* subsp. *nucleatum* JCM14847 UniProt ID: Q8RG11, *Lactobacillus delbrueckii* subsp. *bulgaricus* DSM 20081 UniProt ID: P26297, *Lactobacillus plantarum* subsp. *plantarum* UniProt ID: C0LJH4, *Leuconostoc mesenteroides* subsp. *cremoris* UniProt ID: P51011, *Leuconostoc mesenteroides* subsp. *mesenteroides* UniProt ID: Q03VC9, *Lactobacillus delbrueckii* subsp. *bulgaricus* UniProt ID: P26297, *Lactobacillus* UniProt ID: P30901, *Lactobacillus pentosus* UniProt ID: P26298, *Pediococcus pentosaceus* UniProt ID: Q9AKS9, *Pseudomonas aeruginosa* UniProt ID: Q9I530, *Sporolactobacillus inulius* UniProt ID: A0A0M3KL04, and *Thermodesulfatator indicus* UniProt ID: F8AV.

In some embodiments, the DLDH is the *Leuconostoc mesenteroides* subsp. *cremoris* DLDH (abbv. LmDLDH1; UniProt ID: P51011; SEQ ID NO: 1). In some embodiments, DLDH is the *Leuconostoc mesenteroides* subsp. *mesenteroides* DLDH (abbv. LmDLDH2; UniProt ID: Q03VC9; SEQ ID NO: 2). In some embodiments, the DLDH is the *Lactobacillus delbrueckii* subsp. *bulgaricus* DLDH (abbv. LdDLDH or DLDH3; UniProt ID: P26297; SEQ ID NO: 3). In some embodiments, the DLDH is the *Lactobacillus helveticus* DLDH (abbv. LhDLDH or DLDH4; UniProt ID: P30901; SEQ ID NO: 4). In some embodiments, the DLDH is the *Lactobacillus pentosus* DLDH (abbv. LpDLDH or DLDH5; UniProt ID: P26298; SEQ ID NO: 5). In some embodiments, the DLDH is the *Lactobacillus plantarum* DLDH (abbv. DLDH7; UniProt ID: C0LJH4; SEQ ID NO: 18). In some embodiments, the DLDH is the *Pseudomonas aeruginosa* DLDH (abbv. DLDH8; UniProt ID: Q9I530; SEQ ID NO: 19). In some embodiments, the DLDH is the *Fusobacterium nucleatum* DLDH (abbv. DLDH9; UniProt ID: Q8RG11; SEQ ID NO: 20). In some embodiments, the DLDH is the *Pediococcus acidilactici* DLDH (abbv. DLDH10; UniProt ID: E0NDE9; SEQ ID NO: 21). In some embodiments, the DLDH is the *Lactobacillus plantarum* DLDH (abbv. DLDH12; UniProt ID: T5JY05; SEQ ID NO: 22). In some embodiments, the DLDH is the *Leuconostoc carnosum* DLDH (abbv. DLDH13; UniProt ID: K0DB84; SEQ ID NO: 23).

In some embodiments, the DLDH excludes DLDH from the genus *Limulus*, in particular embodiments from *Limulus polyphemus* when the recombinant host utilized herein is yeast.

In many embodiments, recombinant host cells comprise one or more heterologous nucleic acids encoding a DLDH wherein said recombinant host cells are capable of producing D-lactic acid. In various embodiments, proteins suitable for use in accordance with methods of the present disclosure have DLDH activity and comprise an amino acid sequence with at least 60%, 65%, 70%, 75%, 80%, 85%, 90%, or 95% sequence identity with SEQ ID NO: 1, SEQ ID NO: 2, SEQ ID NO: 3, SEQ ID NO: 4, or SEQ ID NO: 5, SEQ ID NO: 18, SEQ ID NO: 19, SEQ ID NO: 20, SEQ ID NO: 21, SEQ ID NO: 22, and SEQ ID NO: 23. In many embodiments, the recombinant host cell is a *P. kudriavzevii* strain.

In an embodiment, the DLDH is one disclosed in U.S. Pat. No. 7,964,382.

In some embodiments, the DLDH protein has an amino acid sequence derived from the amino acid sequence as shown in SEQ ID NO: 1 by substitution of one or more amino acid residues selected from the list of amino acid residue substitutions tabulated below and has DLDH activity.

TABLE 2

List of anti amino acid residue substitutions

| Substitution type | Position of substitution | Amino acid substituent |
|---|---|---|
| 1 | 40 | Valine (Val) |
| 2 | 112 | Isoleucine (Ile) |
| 3 | 131 | Histidine (His) |
| 4 | 139 | Isoleucine (Ile) |
| 5 | 181 | Glutamic acid (Glu) |
| 6 | 266 | Glycine (Gly) |
| 7 | 267 | Leucine (Leu) |
| 8 | 268 | Phenylalanine (Phe) |
| 9 | 269 | Asparagine (Asn) |
| 10 | 270 | Glutamic acid (Glu) |
| 11 | 271 | Aspartic acid (Asp) |
| 12 | 272 | Tryptophan (Trp) |
| 13 | 273 | Serine (Ser) |
| 14 | 274 | Glycine (Gly) |
| 15 | 276 | Glutamic acid (Glu) |
| 16 | 277 | Phenylalanine (Phe) |
| 17 | 287 | Sertine (Ser) |
| 18 | 292 | Leucine (Leu) |
| 19 | 293 | Valine (Val) |

The amino acid sequence as shown in SEQ ID NO: 17 is derived from the amino acid sequence as shown in SEQ ID NO: 1 via all substitutions indicated in the list of amino acid residue substitutions shown in Table 2. In some embodiments of the methods disclosed herein, the number of substitutions from Table 2 in SEQ ID NO: 1 is, for example, 2 or more, 11 or more, or 19 or more. In some embodiments, the amino acid sequence has amino acid substitutions indicated by substitution types 1 to 19, and in other embodiments, those indicated by substitution types 6 to 16, in the list of amino acid residue substitutions shown in Table 2.

According to another embodiment, the protein comprises an amino acid sequence containing at least amino acid residues 78 and 79, 152 to 175, 235, and 296 of the amino acid sequence as shown in SEQ ID NO: 17 and has DLDH activity. Amino acid residues 78 and 79, 152 to 175, 235, and 296 are considered to be characteristic of the amino acid sequence as shown in SEQ ID NO: 17. In some embodiments, a protein has a histidine residue at position 296 as an active center and the coenzyme NADH binding domain constituted by amino acid residues 152 to 175 of the amino acid sequence as shown in SEQ ID NO: 17. The DLDH protein utilized according to the present disclosure can be obtained by adequately introducing mutation such as substitution, deletion, insertion, and/or addition into the amino acid sequence as shown in SEQ ID NO: 17 or another amino acid sequence via, for example, site-directed mutagenesis, as is well known in the art (see for example, Current Protocols in Molecular Biology, edited by Ausubel et al., Sections 8.1-8.5, 1987, John Wily & Sons) and as disclosed herein. Such modification is not limited to artificial mutagenesis or synthesis. It also includes a product resulting from amino acid mutation in nature on the basis of artificial mutation, but it is not limited thereto.

In wild type DLDH, the residues GXGXXG are conserved, where X refers to any amino acid, followed by a negatively charged amino acid 18-20 residues downstream. A portion of the *Leuconostoc mesenteroides* DLDH sequence is schematically shown below, starting at residue 144, with the conserved residues shown by underlines:

144-
(SEQ ID NO: 17, aa 144-189)
RMQTVGVI<u>GTGHIG</u>RVAINILKGFGAKVIAY<u>D</u>KYPNAELQAEGLYV.

In some embodiments, provided and/or utilized herein are DLDH mutants containing mutations that change the conserved D175 and/or the following two residues at positions 176 and 177. Certain wild type DLDHs useful in accordance with the present disclosure comprise, without limitation, SEQ. ID. NOs: 18-SEQ ID NO: 23, as tabulated below in Table 3. In some embodiments, mutants of these DLDHs as provided herein, are useful in accordance with the present disclosure. Many of the DLDH proteins that may function efficiently in accordance with the present disclosure have a low level of alignment to the enzymes derived from *Leuconostoc mesenteroides*. For example, and without limitation, the DLDH from *Lactobacillus plantarum* (DLDH12, UniProt ID T5JY05) functions efficiently and has about 50-55% alignment to the *L. mesenteroides* proteins (DLDH1 and 2, SEQ ID NO: 1 and SEQ ID NO: 2).

TABLE 3

| Uniprot ID/ SEQ ID NO/ Abbv. | Organism | DLDH Protein Sequence |
|---|---|---|
| C0LJH4/ SEQ ID NO: 18/ DLDH7 | *Lactobacillus plantarum* | MKIIAYAVRDDERPFFDTWMKENPDVEVKLVPELLTEDNVDLAKG FDGADVYQQKDYTAEVLNKLADEGVKNISLRNVGVDNLDVPTVK ARGLNISNVPAYSPNAIAELSVTQLMQLLRQTPLFNKKLAKQDFRW APDIAKELNTMTVGVIGTGRIGRAAIDIFKGFGAKVIGYDVYRNAEL EKEGMYVDTLDELYAQADVITLHVPALKDNYHMLNADAFSKMKD GAYILNFARGTLIDSEDLIKALDSGKVAGAALDTYEYETKIFNKDLE GQTIDDKVFMNLFNRDNVLITPHTAFYTETAVHNMVHVSMNSNKQ FIETGKADTQVKFD |
| Q9I530/ SEQ ID NO: 19/ DLDH8 | *Pseudomonas aeruginosa* | MRILFFSSQAYDSESFQASNHRHGFELHFQQAHLQADTAVLAQGFE VVCAFVNDDLSRPVLERLAAGGTRLVALRSAGYNHVDLAAAEALG LPVVHVPAYSPHAVAEHAVGLILTLNRRLHRAYNRTREGDFSLHGL TGFDLHGKRVGVIGTGQIGETFARIMAGFGCELLAYDPYPNPRIQAL GGRYLALDALLAESDIVSLHCPLTADTRHLIDAQRLATMKPGAMLI NTGRGALVNAAALIEALKSGQLGYLGLDVYEEEADIFFEDRSDQPL QDDVLARLLSFPNVVVTAHQAFLTREALAAIADTTLDNIAAWQDG TPRNRVRA |
| Q8RG11/ SEQ ID NO: 20/ DLDH9 | *Fusobacterium nucleatum* | MQKTKIIFFDIKDYDKEFFKKYGADYNFEMTFLKVRLTEETANLTK GYDVVCGFANDNINKETIDIMAENGIKLLAMRCAGFNNVSLKDVN ERFKVVRVPAYSPHAIAEYTVGLILAVNRKINKAYVRTREGNFSING LMGIDLYEKTAGIIGTGKIGQILIKILRGFDMKVIAYDLFPNQKVADE |

TABLE 3-continued

| Uniprot ID/ SEQ ID NO/ Abbv. | Organism | DLDH Protein Sequence |
|---|---|---|
| | | LGFEYVSLDELYANSDIISLNCPLTKDTKYMINRRSMLKMKDGVIL VNTGRGMLIDSADLVEALKDKKIGAVALDVYEEEENYFFEDKSTQ VIEDDILGRLLSFYNVLITSHQAYFTKEAVGAITVTTLNNIKDFVEGR PLVNEVPQNQ |
| E0NDE9/ SEQ ID NO: 21/ DLDH10 | Pediococcus acidilactici | MKIIAYGIRDDEKPYLDEWVTKNHIEVKAVPDLLDSSNIDLAKDYD GVVAYQQKPYTADLFDKMHEFGIHAFSLRNVGVDNVPADALKKN DIKISNVPAYSPRAIAELSVTQLLALLRKIPEFEYKMAHGDYRWEPD IGLELNQMTVGVIGTGRIGRAAIDIFKGFGAKVIAYDVFRNPALEKE GMYVDTLEELYQQANVITLHVPALKDNYHMLDEKAFGQMQDGTF ILNFARGTLIDTPALLKALDSGKVAGAALDTYENEVGIFDVDHGDQ PIDDPVFNDLMSRRNVMITPHAAFYTRPAVKNMVQIALDNNRDLIE KNSSKNEVKFD |
| T5JY05/ SEQ ID NO: 22/ DLDH12 | Lactobacillus plantarum | MKIIAYAVRDDERPFFDTWMKENPDVEVKLVPELLTEDNVDLAKG FDGADVYQQKDYTAEVLNKLADEGVKNISLRNVGVDNLDVPTVK ARGLNISNVPAYSPNAIAELSVTQLMQLLRQTPMFNKKLAKQDFR WAPNIAKELNTMTVGVIGTGRIGRAAIDIFKGFGAKVIGYDVYRNA ELEKEGMYVDTLDELYAQADVITLHVPALKDNYHMLNADAFSKM KDGAYILNFARGTLIDSEDLIKALDSGKVAGAALDTYEYETKIFNKD LEGQTIDDKVFMNLFNRDNVLITPHTAFYTETAVHNMVHVSMNSN KQFIETGKADTQVKFD |
| K0DB84/ SEQ ID NO: 23/ DLDH13 | Leuconostoc carnosum | MKIFAYGIRDDEKPSLEDWKSTHPEVEVDYTQELLTPETAKLASGS DSAVVYQQLDYTRETLTALSEVGVTNLSLRNVGTDNIDFEAAKELN FNISNVPVYSPNAIAEHSMIQLSRLLRRTKALDAKIAKHDLRWAPTI GREVRMQTVGVIGTGNIGRVAIKILQGFGAKVVAYDKFPNAEIAAQ GLYVDSLDELYAQADAVALFVPGVPENHHMIDASAIAKMKDGVII MNASRGNLMAIDDIIDGLNSGKISDFGMDVYEEEVGLFNEDWSNKE FPDSKIADLISRENVLVTPHTAFYTTKAVLEMVHQSMDAAVAFANG ETPSIAVKY |

In some embodiments, for *Leuconostoc mesenteroides* DLDH, suitable mutations include but are not limited to replacement of D175 (or another negatively charged residue such as D, which is 18-20 residues downstream from the conserved GXGXXG residue of another DLDH)) with S, T, A, V, I, L, M or L. In some embodiments, for *Leuconosoc mesenteroides* DLDH, suitable mutations include but are not limited to replacement of K176 with R, H, S, T, A, V, I, L or M. In some embodiments, for *Leuconosoc mesenteroides* DLDH, suitable mutations include but are not limited to replacement of Y177 with S, T, K, R, H, A, V, I, L or M.

In some embodiments, the mutation comprises changing one or both of the two residues following the conserved negatively charged residue, such as D, which negatively charged sequence is 18-20 residues downstream from the conserved GXGXXG residue of a DLDH.

Mutants D175S, K176R, Y177T of the *Leuconostoc mesenteroides* DLDH, as constructed in accordance with the present disclosure, show increased DLDH activity in vivo, improving the yield of D-lactic acid from 46% to 77% (g-lactate/g-glucose). This result demonstrates the usefulness of the mutant DLDH proteins, and the host cells including them, as provided and/or utilized herein.

In many embodiments, the DLDH is derived from an archaeal source. In many of these embodiments, the DLDH is derived from a host cell belonging to a genus selected from the group comprising *Aeropyrum*. A non-limiting example of archaeal DLDH is the *Aeropyrum pemix* UniProt ID: Q9YEU4.

In many embodiments, the DLDH is derived from a eukaryotic source. In many of these embodiments, the DLDH is derived from a host cell belonging to a genus selected from the group comprising *Allomyces, Arabidopsis, Cardium, Haliotis, Helix, Limulus, Octopus, Phytophthora, Polysphondylium, Pythium, Rattus,* and *Saccharomyces*. A non-limiting example of eukaryotic DLDH is the *Rattus norvegicus* UniProt ID: A0A0G2K1W9.

The DLDH consensus sequence #1 (SEQ ID NO: 6) provides the sequence of amino acids in which each position identifies the amino acid (if a specific amino acid is identified) or a subset of amino acids (if a position is identified as variable) most likely to be found at a specific position in a DLDH. Many amino acids in SEQ ID NO: 6 are highly conserved and DLDHs suitable for use in accordance with the methods of the present disclosure will comprise a substantial number, and sometimes all, of these highly conserved amino acids at positions aligning with the location of the indicated amino acid in SEQ ID NO: 6. In various embodiments, proteins suitable for use in accordance with the methods of the present disclosure have DLDH activity and comprise an amino acid sequence with at least 60%, 65%, 70%, 75%, 80%, 85%, 90% or 95% sequence identity with SEQ ID NO: 6. For example, the LmDLDH2 sequence (SEQ ID NO: 2) is 75.1% identical to consensus sequence SEQ ID NO: 6, and is therefore encompassed by consensus sequence SEQ ID NO: 6. In another example, the LdDLDH sequence (SEQ ID NO: 3) is 85.2% identical to consensus sequence SEQ ID NO: 6, and is therefore also encompassed by consensus sequence SEQ ID NO: 6. The highly conserved amino acids in SEQ ID NO: 6 are K2, I3, A5, Y6, I8, R9, D11, E12, P14, L16, W19, V28, T31, L34, L35, E38, T39, A43, G45, D47, V51, Y52, Q53, Q54, L55, Y57, T61, L62, A64, L65, G69, S74, L75, R76, N77, V78, G79, D81, N82, I83, D84, A88, F93, N97, V98, Y101, S102, P103, A105, I106, A107, E108, H109, Q113, L118, K122, K127, D132, L133, R134, W135, P137, T138, R141, E142, R144, Q146, G149, G152, T153, G154, I156, G157, V159, I163, G166, F167, G168, A169, K170, A173, Y174, D175, N179, G186, Y188, V189, D190, L192, D193, L195, D200, S203, L204, P207, N212, I216, I221, A222, M224, K225, V229, N232, R235, G236, L238, D240, D242, A243, L248, S250, K252, D259, Y261, E262, E264, G266, F268, N269, D271, D279, D284, L285, I286, R288, N290, V291, T294, P295, H296, T297, A298, F299, Y300, T301, T302, A304, V305, M308, V309, G322, and V329.

In some embodiments, the DLDH is from genus *Lactobacillus*. In some embodiments, the DLDH is from *Lactobacillus helveticus*. In some embodiments, the DLDH is from *Lactobacillus pentosus*. In some embodiments, the DLDH is from *Lactobacillus delbrueckii*. In some embodiments, the DLDH is from *Lactobacillus delbrueckii* subsp. *bulgaricus*. In some embodiments, the DLDH from an organism is mutated as disclosed herein.

In some embodiments, the DLDH excludes DLDH from the genus *Leuconostoc*. In some embodiments, the DLDH excludes DLDH from *Leuconostoc mesenteroides*. In some embodiments, the DLDH excludes DLDH disclosed in U.S. Pat. No. 7,964,382.

In some embodiments, the DLDH from *Lactobacillus helveticus*, *Lactobacillus pentosus*, and *Lactobacillus delbrueckii* has less than 90%, such as less than 85%, or less than 80% homology with SEQ ID NO 17. In some embodiments, the DLDH from *Lactobacillus helveticus*, *Lactobacillus pentosus*, and *Lactobacillus delbrueckii* has less than 90%, such as less than 85%, or less than 80% homology with SEQ ID NO 18.

Methods to Identify and/or Improve Enzymes in the D-Lactic Acid Pathway

The following methods have been developed for mutagenesis and diversification of genes for engineering specific or enhanced properties of targeted enzymes. The methods disclosed may be adapted as needed depending on the target enzyme properties desired. In some instances, the disclosed methods are suitable for use in engineering enzymes towards improved DLDH activity of the D-lactic acid pathway. In some embodiments, the DLDH is derived from an enzyme with native activity towards a substrate that is structurally similar to pyruvate.

Methods described herein comprise protein mutagenesis, identification, expression, purification, and characterization. Further, identification of mutated proteins can include activity screens and phenotypic selections.

Generating Protein Libraries Via Mutagenesis

Enzymes that are identified as good mutagenesis starting points enter the protein engineering cycle, which comprises protein mutagenesis, protein identification, protein expression, protein characterization, recombinant host cell characterization, and any combination thereof. Iterative rounds of protein engineering are typically performed to produce an enzyme variant with properties that are different from the template/original protein. Examples of enzyme characteristics that are improved and/or altered by protein engineering comprise, for example, substrate binding ($K_m$; i.e., a measure of enzyme binding affinity for a particular substrate) that comprises non-natural substrate selectivity/specificity; enzymatic reaction rates ($k_{cat}$; the turnover rate of a particular enzyme-substrate complex into product and enzyme), to achieve desired pathway flux; temperature stability, for high temperature processing; pH stability, for processing in extreme pH ranges; substrate or product tolerance, to enable high product titers; removal of inhibition by products, substrates or intermediates; expression levels, to increase protein yields and overall pathway flux; oxygen stability, for operation of air sensitive enzymes under aerobic conditions; and anaerobic activity, for operation of an aerobic enzyme in the absence of oxygen. In some embodiments, the enzyme variant enables improved D-lactic acid pathway flux. In some embodiments, the enzyme variant enables increased D-lactate yield, titer and/or productivity. In some embodiments, the enzyme variant enables increased substrate specificity. In some embodiments, the enzyme variant displays improved kinetic properties, such as decreased $K_m$ and/or increased $k_{cat}$. In some embodiments, the enzyme variant has increased $K_m$ and/or decreased $k_{cat}$, for the substrate pyruvate. In some embodiments, the enzyme variant has $K_m \leq 3$ mM with pyruvate as substrate. In some embodiments, the enzyme variant has $k_{cat} \geq 10$ turnovers per second with pyruvate as substrate. In some embodiments, the enzyme variant is a product of one or more protein engineering cycles. In some embodiments, the enzyme variant comprises one or more point mutations.

In general, random and rational mutagenesis approaches are acceptable methods for generating DNA libraries of mutant proteins. Error-prone PCR is a random mutagenesis method widely used for generating diversity in protein engineering, and error-prone PCR is not only fast and easy, but it is also a method that has successfully produced mutated enzymes with altered activity from a wild type DNA template. (Wilson, D. S. & Keefe, A. D. Random mutagenesis by PCR. *Curr. Protoc. Mol. Biol.* Chapter 8, Unit 8.3 (2001).) To help increase the odds of identifying an enzyme with 3-PG/2-PG phosphatase activity, rational mutagenesis of a small number of active site mutations is also useful. Structural modeling allows one to identify amino acids in the active site involved with substrate recognition. Other mutagenesis approaches that could be used comprise DNA shuffling and combinatorial mutagenesis. In some embodiments, the mutagenesis step is carried out more than once, resulting in iterative rounds of engineering.

Generating Strain Libraries Via Directed Evolution

In another aspect of this disclosure, directed evolution methods can be used to identify enzymes with DLDH activity and/or improved kinetic parameters (for example, decreasing the enzyme $K_m$ and/or increasing the enzyme $k_{cat}$ when using pyruvate as the substrate) of enzymes exhibiting suboptimal activity toward pyruvate. Directed evolution approaches are useful in generating strain libraries with a wide diversity of mutations wherein the mutations are driven by the process of natural selection given the constraints provided to the organism in its growth environment. Evolution approaches provide an effective and impartial way of introducing sequence mutations that give rise to functional change at an organism scale, enabling practitioners to explore non-intuitive mutations in the universe of possibilities that lie beyond the confines of one's understanding about structure-function specificity.

In some embodiments, a screen is designed to monitor the progress of evolution over time. In some of these embodiments, it is useful to link desired mutagenesis with a measurable phenotype so that the rate of evolution can be monitored over an extended period of time. In some of these embodiments, the measurable phenotype comprises cell growth, glucose consumption, and metabolite production. In some embodiments, the measurable phenotype is favored by a selection. In some embodiments, the directed evolution experiment is designed so that mutations acquired in the target gene(s) is a measurable phenotype that is advantageous to the organism. In some of these embodiments, the advantageous measurable phenotype comprises cellular fitness, energy production, growth rate, tolerance to toxicity, and tolerance to extreme culture conditions (such as high or low pH, high or low temperature, high or low osmotic pressure, drought, and nutrient limitation). In various embodiments, one or more synthetic metabolic pathways are constructed by introducing exogenous nucleic acids to recombinant host cells. In these embodiments, the one or more synthetic metabolic pathways provide a method of applying selective pressure or a method of selecting strain variants that result from directed evolution.

Besides a well-crafted screen and/or selection, before the evolution experiment begins, starting nucleic acid templates for proteins of interest (i.e., target gene(s) or parent gene(s)) can also be identified. In embodiments of the present disclosure, enzymes that serve as a good starting point for DLDH engineering are identified. In these embodiments, DLDH-encoding nucleic acids are integrated into the genome of recombinant host cells. In some embodiments, the DLDH is derived from an enzyme with native activity towards a substrate that is structurally similar to pyruvate.

Once a screen and/or selection is established and target genes (i.e., for DLDH according to embodiments of the present disclosure) are identified and integrated into the genome of recombinant host cells, recombinant host cells enter the directed evolution cycle, wherein the directed evolution cycle comprises: (1) mutagenesis in response to selective pressure; (2) analysis of recombinant host cells in the generated library for measurable phenotypic differences that arise due to selective pressure; and (3) isolation and characterization of evolved variants.

In some embodiments, acquisition of a mutation in the target gene enables the recombinant host cell to overcome the selective pressure. In some embodiments, recombinant host cells are passaged throughout the course of mutagenesis with selective pressure. In various embodiments, the selective pressure comprises nutrient limitation, cellular toxicity, and extreme culture conditions that further comprise high or low pH, high or low temperature, and high or low osmotic pressure. In some embodiments, the recombinant host cells are initially propagated without selective pressure prior to mutagenesis.

After exposure to selective pressure for some period of time, the evolved or evolving strains are screened for a change in phenotype in response to selective pressure. Non-limiting examples of phenotypic change include faster glucose consumption, faster cell growth, higher flux through a metabolic pathway or pathways, improved product yield/titer/productivity, decreased byproduct yield/titer, increased tolerance to toxicity, or increased tolerance to extreme culture conditions.

Enzyme Characterization

Protein variants that result from strain library generation and screening are integrated into the genome of recombinant host cells and resulting strain variants are analyzed for DLDH activity. In some embodiments, iterative rounds of protein engineering are performed to produce enzyme variants with optimized properties, wherein the iterative rounds of protein engineering comprise rational mutagenesis, random mutagenesis, and directed evolution. In these embodiments, select variants from preceding rounds of protein engineering are identified for further protein engineering. Non-limiting examples of such properties comprise improved enzyme kinetics for specificity and/or turnover, improved pathway flux, increased metabolite yield, decreased byproduct yield. In some embodiments, culture medium or fermentation broth is analyzed for the presence of metabolites such as D-lactic acid and/or byproducts, wherein the method of analysis is HPLC (high-performance liquid chromatography).

Ancillary Proteins

In addition to the D-lactic acid pathway enzymes, ancillary proteins are other proteins that are overexpressed in recombinant host cells of the present disclosure whose overexpression results in an increase in D-lactic acid as compared to control, or host cells that do not overexpress said proteins. Ancillary proteins function outside the D-lactic acid pathway, wherein each ancillary protein plays a role that indirectly boosts the recombinant host cell's ability to produce D-lactic acid. Ancillary proteins comprise any protein (excluding D-lactic acid pathway enzymes) of any structure or function that can increase D-lactic acid yields, titers, or productivities when overexpressed. Non-limiting examples of classes of proteins include transcription factors, transporters, scaffold proteins, proteins that decrease byproduct accumulation, and proteins that regenerate or synthesize redox cofactors. The embodiments described herein for improvements in D-lactic acid yields, productivities, and/or titers can be adapted and/or modified in various ways and applied to L-lactic acid yields, productivities, and/or titers without departing from the spirit of this disclosure.

Provided herein in certain embodiments are recombinant host cells comprising one or more heterologous nucleic acids encoding one or more ancillary proteins wherein said recombinant host cell is capable of producing higher D-lactic acid yields, titers, or productivities as compared to control cells, or host cells that do not comprise said heterologous nucleic acid(s). In some embodiments, that host recombinant cell naturally produces D-lactic acid, and in these cases, the D-lactic acid yields, titers, and/or productivities are increased. In other embodiments, the recombinant host cell comprises one or more heterologous nucleic acids encoding one or more D-lactic acid pathway enzymes.

In certain embodiments of the present disclosure, the recombinant host cells comprise one or more heterologous nucleic acids encoding one or more D-lactic acid pathway enzymes and one or more heterologous nucleic acids encoding one or more ancillary proteins. In certain of these embodiments, the recombinant host cells may be engineered to express more of these ancillary proteins. In these particular embodiments, the ancillary proteins are expressed at a higher level (i.e., produced at a higher amount as compared to cells that do not express said ancillary proteins) and may be operatively linked to one or more exogenous promoters or other regulatory elements.

In certain embodiments, recombinant host cells comprise both endogenous and heterologous nucleic acids encoding one or more D-lactic acid pathway enzymes and one or more ancillary proteins. In certain embodiments, the recombinant host cells comprise one or more heterologous nucleic acids encoding one or more D-lactic acid pathway enzymes and/or one or more ancillary proteins, and one or more endogenous nucleic acids encoding one or more D-lactic acid pathway enzymes and/or one or more ancillary proteins. In some embodiments, that host recombinant cell naturally produces D-lactic acid, and in these cases, the D-lactic acid yields, titers, and/or productivities are increased. In other embodiments, the recombinant host cell does not naturally produce D-lactic acid and thus comprises one or more heterologous nucleic acids encoding one or more D-lactic acid pathway enzymes.

In certain embodiments, endogenous nucleic acids of ancillary proteins are modified in situ (i.e., on chromosome in the host cell genome) to alter levels of expression, activity, or specificity. In some embodiments, heterologous nucleic acids are inserted into endogenous nucleic acids of ancillary proteins.

Ancillary Proteins for Redox Cofactor Biogenesis

Ancillary proteins comprise proteins that recycle the redox cofactors that are produced during D-lactic acid pathway activity. Redox balance is fundamental to sustained metabolism and cellular growth in living organisms. Intracellular redox potential is determined by redox cofactors that facilitate the transfer of electrons from one molecule to another within a cell. Redox cofactors in yeast comprise the nicotinamide adenine dinucleotides, NAD and NADP, the flavin nucleotides, FAD and FMN, and iron sulfur clusters (Fe—S clusters).

Redox constraints play an important role in end-product formation. Additional reducing power will typically be provided to produce compounds whose degree of reduction is higher than that of the substrate. Conversely, producing compounds with a degree of reduction lower than that of the substrate will force the synthesis of byproducts with higher degrees of reduction to compensate for excess reducing power generated from substrate oxidation. Thus, it is advantageous to maintain redox neutrality to ensure high end-product yields. For example, the D-lactic acid pathway is redox balanced and there is no net formation of $NAD(P)^+$ or $NAD(P)H$ for each mol of glucose converted to D-lactic acid in the cytosol.

The NAD and NADP cofactors are involved in electron transfer and contribute to about 12% of all biochemical reactions in a cell (Osterman A., EcoSal Plus, 2009). NAD is assembled from L-aspartate, dihydroxyacetone phosphate (DHAP; glycerone), phosphoribosyl pyrophosphate (PRPP) and ATP. The NADP is assembled in the same manner and further phosphorylated. In some embodiments, recombinant host cells comprise heterologous and/or endogenous nucleic acids encoding one or more ancillary proteins that facilitate NAD and NADP cofactor assembly. In some embodiments, the ancillary proteins comprise one, more or all proteins suitable for use in accordance with methods of the present disclosure having NAD and/or NADP assembly capability, NAD and/or NADP transfer capability, NAD and/or NADP chaperone capability, or any combination thereof.

Similarly, Fe—S clusters facilitate various enzyme activities involved with electron transfer. Because both iron and sulfur atoms are highly reactive and toxic to cells, Fe—S cluster assembly uses carefully coordinated synthetic pathways in living cells. The three known pathways are the Isc (iron sulfur cluster) system, the Suf (sulfur formation) system, and the Nif (nitrogen fixation) system. Each of these systems has a physiological role, yet several functional components are shared between them. First, a cysteine desulfurase enzyme liberates sulfur atoms from free cysteine. Then, a scaffold protein receives the liberated sulfur for Fe—S cluster assembly. Finally, the Fe—S cluster is transferred to a target apoprotein. In some embodiments of the present disclosure, recombinant host cells comprise heterologous and/or endogenous nucleic acids encoding one or more ancillary proteins that facilitate Fe—S cluster assembly. In some embodiments, the ancillary proteins comprise one, more or all proteins of the Isc system, the Suf system, the Nif system, or any combination thereof. In some embodiments, recombinant host cells comprise one or more heterologous nucleic acids encoding one or more proteins suitable for use in accordance with methods of the present disclosure having cysteine desulfurase activity, Fe—S cluster assembly capability, Fe—S cluster transfer capability, iron chaperone capability, or any combination thereof.

Ancillary Proteins for D-Lactic Acid Transport

Another class of ancillary proteins useful for increasing D-lactic acid yields, titers, and/or productivities are organic acid transporter proteins. In some embodiments, recombinant host cells comprise one or more heterologous and/or endogenous nucleic acids encoding one or more organic acid transporter proteins. In many embodiments, the organic acid transporter is derived from a fungal source. In some embodiments, the organic acid transporter is selected from the group comprising *Saccharomyces cerevisiae* PDR12 (abbv. ScPDR12; UniProt ID: Q02785; SEQ ID NO: 7), *Saccharomyces cerevisiae* WAR1 (abbv. ScWAR1; UniProt ID: Q03631; SEQ ID NO: 8), *Schizosaccharomyces pombe* MAE1 (abbv. SpMAE1; UniProt ID: P50537; SEQ ID NO: 9), and *Kluyveromyces marxianus* PDC12 (abbv. KmPDC12; UniProt ID: W0T9C6; SEQ ID NO: 10). In some embodiments, recombinant host cells comprise one or more heterologous nucleic acids encoding one or more proteins suitable for use in accordance with methods of the present disclosure have D-lactic acid transporter activity. In some embodiments, recombinant host cells comprise one or more heterologous nucleic acids encoding one or more proteins that comprise an amino acid sequence with at least 60%, 65%, 70%, 75%, 80%, 85% 90% or 95% sequence identity with ScPDR12 (SEQ ID NO: 7), ScWAR1 (SEQ ID NO: 8), SpMAE1 (SEQ ID NO: 9), or KmPDC12 (SEQ ID NO: 10).

Decreasing or Eliminating Expression of Byproduct Pathway Enzymes

In an additional aspect of this disclosure, nucleic acids encoding byproduct pathway enzymes can be disrupted in recombinant host cells of the present disclosure to increase D-lactic acid yields, productivities, and/or titers; and/or to decrease byproduct titers and/or yields as compared to control cells, or host cells that express native/undisrupted levels of said byproduct pathway enzymes. Byproduct pathway enzymes comprise any protein (excluding D-lactic acid pathway enzymes) of any structure or function that can increase D-lactic acid product yields, titers, and/or productivities when disrupted because they utilize intermediates or products of the D-lactic acid pathway. In addition, byproduct pathway enzymes also comprise any protein (excluding D-lactic acid pathway enzymes) of any structure or function that can decrease undesired byproduct yields, titers, and/or productivities when disrupted because they utilize intermediates or products of the D-lactic acid pathway. The embodiments described herein for improvements in byproduct enzymes for the D-lactic acid pathway can be adapted and/or modified in various ways and applied to the byproduct enzymes for the L-lactic acid pathway without departing from the spirit of this disclosure.

Byproducts that accumulate during D-lactic acid production can lead to: (1) lower D-lactic acid titers, productivities, and/or yields; and/or (2) accumulation of byproducts in the fermentation broth that increase the difficulty of downstream purification processes. In some embodiments, recombinant host cells may comprise genetic disruptions that encompass alterations, deletions, knockouts, substitutions, promoter modifications, premature stop codons, or knock-downs that decrease byproduct accumulation. In some embodiments, recombinant host cells comprising a disruption of one or more genes encoding a byproduct pathway enzyme will have altered performance characteristics as compared to cells without said genetic disruption(s), such as decreased or eliminated byproduct pathway enzyme expression, decreased or eliminated byproduct accumulation, improved D-lactic acid activity, altered metabolite flux through the D-lactic acid pathway, higher D-lactic acid titers, productivities, yields, and/or altered cellular fitness.

Decreasing byproduct formation can increase D-lactic acid activity, resulting in an increased amount of D-lactic acid produced. In many embodiments, recombinant host cells of the present disclosure comprising one or more genetic disruptions of one or more genes encoding a byproduct pathway enzyme produce an increased D-lactic acid titer as compared to host cells that do not comprise said genetic disruption(s). In some of these embodiments, the D-lactic acid titer in the fermentation broth is increased by 0.5 g/L, 1 g/L, 2.5 g/L, 5 g/L, 7.5 g/L, 10 g/L, or more than 10 g/L.

In addition to increasing D-lactic acid titers, decreasing byproduct formation can also help increase D-lactic acid yields. Because yield is independent of the volume of the fermentation broth, which can change during the course of a fermentation, it is often advantageous to measure D-lactic acid yields. In many embodiments, recombinant host cells of the present disclosure comprising one or more genetic disruptions of one or more genes encoding byproduct pathway enzymes produce an increased D-lactic acid yield as compared to host cells that do not comprise said genetic disruption. In some of these embodiments, the D-lactic acid yield is increased by 0.5%, 1%, 2.5%, 5%, 7.5%, 10%, or more than 10% (g-D-lactic acid/g-substrate). The substrate in this yield calculation is the fermentation substrate, which is typically glucose, but may also be other, non-glucose substrates (for example, sucrose, glycerol, or pyruvate).

Increasing D-lactic acid can decrease manufacturing costs and can further work to disrupt genes encoding byproduct pathway enzymes in order to decrease byproduct formation. Byproducts are typically unwanted chemicals, are disposed of as waste, and their disposal can involve elaborate processing steps and containment requirements. Therefore, decreasing byproduct formation can also lower production costs. In many embodiments, recombinant host cells of the present disclosure comprising one or more genetic disruptions of one or more genes encoding a byproduct pathway enzyme produces a lower byproduct titer as compared to host cells that do not comprise said genetic disruption. In some of these embodiments, a recombinant host cell of the disclosure comprising genetic disruption of one or more byproduct pathway enzymes produces a byproduct titer that is 0.5 g/L, 1 g/L, 2.5 g/L, 5 g/L, 7.5 g/L, 10 g/L, or greater than 10 g/L less than host cells that do not comprise said genetic disruption.

In many embodiments, recombinant host cells of the present disclosure comprising one or more genetic disruptions of one or more genes encoding a byproduct pathway enzyme produces a lower byproduct yield as compared to host cells that do not comprise said genetic disruption(s). In some of these embodiments, recombinant host cells comprise genetic disruption of one or more genes encoding byproduct pathway enzymes produce a byproduct yield that is 0.5%, 1%, 2.5%, 5%, 7.5%, 10%, or greater than 10% (g-byproduct/g-substrate) less than host cells that do not comprise said genetic disruption. As with the D-lactic acid yield calculation, the substrate used in the byproduct yield calculation is the carbon source provided to the fermentation; this is typically glucose, sucrose, or glycerol, but may be any carbon substrate.

Non-limiting examples of byproducts that arise due to consumption of a D-lactic acid pathway or a downstream pathway substrate, intermediate or product include acetaldehyde, acetyl-CoA and oxaloacetate. In the event of a redox imbalance, an undesirable excess of reduced or oxidized cofactors may also accumulate; thus, the redox cofactors NADH, $NAD^+$, NADPH and $NADP^+$ can also be considered byproducts.

A non-limiting list of enzyme-catalyzed reactions that utilize the D-lactic acid pathway substrate (i.e., pyruvate) are found in Table 4. Decreasing or eliminating expression of one, some or all of the genes encoding the enzymes in Table 4 can increase D-lactic acid production and/or decrease byproduct production. In many cases, the product of the enzyme-catalyzed reactions provided in Table 4 can accumulate in the fermentation broth; in such cases, this indicates that expression of the native gene encoding the listed enzyme should be reduced or eliminated. For example, the occurrence of acetaldehyde in the fermentation broth indicates that expression of a native gene encoding pyruvate decarboxylase should be decreased or eliminated. In some cases, the product of the specific reaction listed in Table 4 is further converted, either spontaneously or through the action of other enzymes, into a byproduct that accumulates in the fermentation broth. In cases where byproduct accumulation is due to the activity of multiple enzymes, one or more of the genes encoding the one or more byproduct pathway enzymes can be deleted or disrupted to reduce byproduct formation.

In some embodiments of the present disclosure, recombinant host cells comprise microbial strains with decreased or eliminated expression of one, some or all of the genes encoding enzymes listed in Table 4. In some embodiments, recombinant host cells comprise microbial strains with decreased byproduct accumulation wherein the byproducts are formed through the activity of one, some or all of the enzymes listed in Table 4. In some embodiments, recombinant host cells comprise microbial strains with decreased expression of pyruvate-utilizing enzymes. In some embodiments, recombinant host cells comprise microbial strains with decreased expression of D-lactic acid-utilizing enzymes. In some embodiments, recombinant host cells comprise microbial strains with inability to catabolize or breakdown D-lactic acid and/or D-lactic acid. In some embodiments, recombinant host cells comprise genetic modifications that reduce the ability of the host cells to catabolize the D-lactic acid except via the D-lactic acid and/or D-lactic acid pathway. In some embodiments, recombinant host cells comprise genetic modifications that decrease the ability of the host cells to catabolize pyruvate except via the D-lactic acid pathway. In some embodiments, the host cells utilized herein have reduced or ablated acetyl coenzyme A synthetase (AcsA, EC 6.2.1.1) or an AcsA homolog activity. In some embodiments, yeast host cells utilized herein have normal acetyl coenzyme A synthetase (AcsA) or an AcsA homolog activity; in other words, the yeast host cells do not have reduced or ablated acetyl coenzyme A synthetase (AcsA) or an AcsA homolog activity.

TABLE 4

Enzyme-catalyzed reactions that consume a substrate, intermediate or product of glycolysis or the D-lactic acid pathway

| Substrate | EC # | Enzyme name | Reaction formula |
|---|---|---|---|
| Pyruvate | 4.1.1.1 | Pyruvate decarboxylase | Pyruvate + $H^+ \rightarrow$ Acetaldehyde + $CO_2$ |
| Pyruvate | n/a | Pyruvate dehydrogenase complex | Pyruvate + CoA + Oxidized cofactor $\rightarrow$ Acetyl-CoA + $CO_2$ + Reduced cofactor |
| Pyruvate | 6.4.1.1 | Pyruvate carboxylase | Pyruvate + $HCO_3^-$ + ATP $\rightarrow$ Oxaloacetate + ADP + Phosphate + $H^+$ |

Decreasing or Eliminating Expression of Pyruvate Decarboxylase

Pyruvate decarboxylase catalyzes the irreversible/unidirectional conversion of one molecule of pyruvate to one molecule of acetaldehyde and one molecule of $CO_2$. Pyruvate decarboxylase activity can lead to the formation of at least three undesirable pyruvate decarboxylase-based byproducts: acetaldehyde, acetate, and ethanol. There are at least 3 pyruvate decarboxylase homologs in *P. kudiavzevii*: PkPDC1 (SEQ ID NO: 11), PkPDC5 (SEQ ID NO: 12) and PkPDC6 (SEQ ID NO: 13); decreasing or eliminating expression of one or more of these homologs can be useful for increasing D-lactic acid production and/or decreasing accumulation of pyruvate decarboxylase-based byproducts. As described above, homologous proteins share substantial sequence identity with each other. Any protein that is homologous to one, more, or all of the pyruvate decarboxylases of the present disclosure (SEQ ID NOs. 11, 12 and 13) will share substantial sequence identity one or more of these proteins.

In some embodiments, recombinant host cells comprise genetic disruptions in one or more pyruvate decarboxylase homologs. As defined above, genetic disruptions encompass nucleic acid deletions, nucleic acid insertions, nucleic acid substitutions, nucleic acid mutations, premature stop codons and promoter modifications. In some embodiments, recombinant host cells of the present disclosure comprise a genetic disruption of a homologous pyruvate decarboxylase gene with at least 60%, 65%, 70%, 75%, 80%, 85%, 90%, 95%, or more than 95% homology when compared to PkPDC1 (SEQ ID NO: 11), PkPDC5 (SEQ ID NO: 12) or PkPDC6 (SEQ ID NO: 13). In some of these embodiments, the recombinant host cell is a *P. kudiavzevii* strain. In some embodiments, recombinant host cells comprise one or more gene disruptions that produce altered, decreased or eliminated activity in one, two or all three, pyruvate decarboxylase proteins. In some of these other embodiments, the recombinant host cell is a *P. kudriavzevii* strain.

In some embodiments, recombinant host cells comprise heterologous nucleic acids encoding D-lactic pathway enzymes, and further comprise one or more genetic disruptions of one, more, or all of the pyruvate decarboxylase homologs. In certain embodiments, acetaldehyde byproduct titer (i.e., g of byproduct/liter of fermentation volume) at the end of fermentation is 10 g/L or less, 5 g/L or less, or 2.5 g/L or less. In certain embodiments, acetaldehyde byproduct yield (i.e., percentage of g of byproduct/g of substrate) at the end of fermentation is 10% or less, 5% or less, 2.5% or less, or 1% or less. In certain embodiments, acetate byproduct titer at the end of fermentation is 10 g/L or less, 5 g/L or less, or 2.5 g/L or less. In certain embodiments, acetate byproduct yield at the end of fermentation is 10% or less, 5% or less, 2.5% or less, or 1% or less. In some embodiments, ethanol byproduct titer at the end of a fermentation is 10 g/L or less, 5 g/L or less, or 2.5 g/L or less. In certain embodiments, ethanol byproduct yield at the end of fermentation is 10% or less, 5% or less, 2.5% or less, or 1% or less.

Decreasing or Eliminating Expression of Pyruvate Dehydrogenase Complex

The pyruvate dehydrogenase complex catalyzes the conversion of one molecule of pyruvate, one molecule of coenzyme A and one molecule of $NAD^+$ to one molecule of acetyl-CoA, one molecule of $CO_2$ and one molecule of NADH; in wild type *P. kudriavzevii*, this enzyme is localized in the mitochondria. In most native microbes, the pyruvate dehydrogenase complex is used for aerobic metabolism of pyruvate to $CO_2$ through the activity of the tricarboxylic acid cycle enzymes. Genetic disruption of one or more genes encoding a protein subunit of the pyruvate dehydrogenase complex can decrease pyruvate dehydrogenase complex protein activity or expression, consequently increasing D-lactic acid production and/or decreasing $CO_2$ byproduct formation. In some embodiments of the present disclosure, recombinant host cells comprise decreased or eliminated expression and/or activity of one or more pyruvate dehydrogenase complex proteins. In some of these embodiments, recombinant host cells comprise decreased or eliminated expression and/or activity of the E1 α-subunit of the pyruvate dehydrogenase complex (abbv. PkPDA1; SEQ ID NO: 14). In some embodiments, recombinant host cells comprise one or more heterologous nucleic acids encoding one or more proteins that comprise an amino acid sequence with at least 60%, 65%, 70%, 75%, 80%, 85%, 90%, or 95% sequence identity with SEQ ID NO: 14. In some embodiments, the recombinant host cell is a *P. kuiavzevii* strain.

In one embodiment, wherein recombinant host cells comprise a D-lactic acid pathway and genetic disruption(s) that decrease or eliminate expression and/or activity of one or more pyruvate dehydrogenase complex proteins, the D-lactic acid titer and/or yield is higher as compared to recombinant host cells that do not comprise said genetic disruption(s). In some of these embodiments, said recombinant host cells produce less carbon dioxide as compared to recombinant host cells that do not comprise said genetic disruption(s). In some of these embodiments, the recombinant host cell's carbon dioxide yield (i.e., g-carbon dioxide/g-glucose consumed) is lower as compared to recombinant host cells that do not comprise said genetic disruption(s).

Decreasing or Eliminating Expression of Glycerol-3-Phosphate Dehydrogenase

Additional byproducts can arise from intermediates in glycolysis. Glycerol is a common byproduct that occurs under conditions of excess NADH. NAD-dependent glycerol-3-phosphate dehydrogenase (EC 1.1.1.8) catalyzes the conversion of one molecule of dihydroxyacetone phosphate (DHAP; glycerone phosphate) and one molecule of NAD(P)H to one molecule of glycerol 3-phosphate and one molecule of $NAD(P)^+$, leading to the formation of the undesired byproduct glycerol. In *P. kudriavzevii*, NAD-dependent glycerol-3-phosphate dehydrogenase activity is the Gpd1 protein (abbv. PkGPD1; SEQ ID NO: 15).

Decreasing or eliminating the expression of PkGPD1 or its homologs is useful for decreasing glycerol byproduct accumulation. In some embodiments of the present disclosure, recombinant host cells comprise one or more genetic disruptions in one or more nucleic acids encoding a glycerol-3-phosphate dehydrogenase that gives rise to decreased, altered or eliminated expression and/or protein activity. In embodiments where the recombinant host cell is a *P. kudiavzevii* strain, the glycerol-3-phosphate dehydrogenase is PkGPD1.

In some embodiments, recombinant host cells comprise heterologous nucleic acids encoding D-lactic acid pathway enzymes, and further comprise one or more genetic disruptions in PkGPD1 (SEQ ID NO: 15), or in one, more, or all PkGPD1 homologs wherein several amino acids in the PkGPD1 homologs are conserved. In certain embodiments, glycerol byproduct titer at the end of fermentation is 10 g/L or less, 5 g/L or less, or 2.5 g/L or less. In certain embodiments, glycerol byproduct yield at the end of fermentation is 10% or less, 5% or less, 2.5% or less, or 1% or less.

Decreasing or Eliminating Expression of NAD(P)H Dehydrogenase

The DLDH of the D-lactic acid pathway catalyzes the conversion of one molecule of pyruvate and one molecule of NAD(P)H to one molecule of D-lactic acid and one molecule of NAD(P)$^+$. In order to ensure NAD(P)H availability does not become a limiting factor in this reaction, host cell endogenous proteins with NAD(P)H dehydrogenase activity are decreased or eliminated in some embodiments of the present disclosure.

NAD(P)H dehydrogenases belong to the enzyme family of oxidoreductases that work with other electron acceptors to catalyze the transfer of electrons from one molecule to another. NAD(P)H dehydrogenases typically function in the shuttling of electrons from the cytosol to the electron transport chain where they are used to generate ATP and water from $O_2$. NADH dehydrogenases utilize the NADH cofactor while NADPH dehydrogenases utilize the NADPH cofactor. NAD(P)H dehydrogenases typically have specificity to either NADH or NADPH, although it is possible for some engineered as well as natural NAD(P)H dehydrogenases to be able to bind either cofactor with varying affinities and utilize either cofactor with varying catalytic efficiencies.

In accordance with the present disclosure, it may be desirable to decrease or eliminate host cell endogenous NAD(P)H dehydrogenase expression so that the D-lactic acid pathway is not limited by the availability of NAD(P)H cofactor. Decreasing or eliminating expression of one or more homologs of NAD(P)H dehydrogenase is useful for increasing D-lactic acid production. In embodiments where the DLDH utilizes the NADH cofactor, the expression of more host cell endogenous NADH dehydrogenase enzymes is decreased or eliminated. In embodiments where the DLDH utilizes the NADPH cofactor, the expression of one or more host cell endogenous NADPH dehydrogenase enzymes is decreased or eliminated. In some embodiments, the NAD(P)H dehydrogenase is the mitochondrial external NADH dehydrogenase. In some embodiments, the NAD(P)H dehydrogenase is the *P. kudriavzevii* Nde1 protein (abbv. PkNDE1; SEQ ID NO: 16). In some embodiments, recombinant host cells comprise one or more heterologous nucleic acids encoding one or more proteins that comprise an amino acid sequence with at least 60%, 65%, 70%, 75%, 80%, 85%, 90%, or 95% sequence identity with SEQ ID NO: 16. In embodiments wherein the recombinant host cells comprise a D-lactic acid pathway and a decrease or elimination of one or more copies of host cell endogenous NAD(P)H dehydrogenase, the recombinant host cells further comprise increased D-lactic acid titer, D-lactic acid yield, and/or D-lactic acid productivity.

The embodiments described herein for decreasing or eliminating NAD(P)H dehydrogenase expression in the D-lactic acid pathway can be adapted and/or modified in various ways and applied to L-lactic acid pathway without departing from the spirit of this disclosure.

Genetic Engineering

Expression of D-lactic acid pathway enzymes is achieved by transforming host cells with exogenous nucleic acids encoding D-lactic acid pathway enzymes, producing recombinant host cells of the present disclosure. The same is true for expression of ancillary proteins. Any method can be used to introduce exogenous nucleic acids into a host cell to produce a recombinant host cell of the present disclosure. Many such methods are known to practitioners in the art. Some examples comprise electroporation, chemical transformation, and conjugation. Some examples comprise electroporation, chemical transformation, and conjugation. After exogenous nucleic acids enter the host cell, nucleic acids may integrate in to the cell genome via homologous recombination. The embodiments described herein for improvements in the D-lactic acid pathway enzymes can be adapted and/or modified in various ways and applied to L-lactic acid pathway enzymes without departing from the spirit of this disclosure.

Recombinant host cells of the present disclosure may comprise one or more exogenous nucleic acid molecules/elements, as well as single or multiple copies of a particular exogenous nucleic acid molecule/element as described herein. These molecules/elements comprise transcriptional promoters, transcriptional terminators, protein coding regions, open reading frames, regulatory sites, flanking sequences for homologous recombination, and intergenic sequences.

Exogenous nucleic acids can be maintained by recombinant host cells in various ways. In some embodiments, exogenous nucleic acids are integrated into the host cell genome. In other embodiments, exogenous nucleic acids are maintained in an episomal state that can be propagated, either stably or transiently, to daughter cells. Exogenous nucleic acids may comprise selectable markers to ensure propagation. In some embodiments, the exogenous nucleic acids are maintained in recombinant host cells with selectable markers. In some embodiments, the selectable markers are removed and exogenous nucleic acids are maintained in a recombinant host cell strain without selection. In some embodiments, removal of selectable markers is advantageous for downstream processing and purification of the fermentation product.

In some embodiments, endogenous nucleic acids (i.e., genomic or chromosomal elements of a host cell), are genetically disrupted to alter, mutate, modify, modulate, disrupt, enhance, remove, or inactivate a gene product. In some embodiments, genetic disruptions alter expression or activity of proteins native to a host cell. In some embodiments, genetic disruptions circumvent unwanted byproduct formation or byproduct accumulation. Genetic disruptions occur according to the principle of homologous recombination via methods well known in the art. Disrupted endogenous nucleic acids can comprise open reading frames as well as genetic material that is not translated into protein. In some embodiments, one or more marker genes replace deleted genes by homologous recombination. In some of these embodiments, the one or more marker genes are later removed from the chromosome using techniques known to practitioners in the art.

Methods of Producing D-Lactic Acid, D-Lactate Salts with Recombinant Host Cells

Methods are provided herein for producing D-lactic acid or D-lactate salts from recombinant host cells of the present disclosure. In certain embodiments, the methods comprise the steps of: (1) culturing recombinant host cells as provided by the present disclosure in a fermentation broth containing at least one carbon source and one nitrogen source under conditions such that D-lactic acid or D-lactate is produced; and (2) recovering the D-lactate, D-lactic acid or D-lactate salt from the fermentation broth. In some embodiments, the D-lactic acid is first converted to a D-lactate salt before the D-lactate salt is recovered from the fermentation broth. In some embodiments, the D-lactate acid or D-lactate salt is first converted to a downstream product before the downstream product is recovered from the fermentation broth. The embodiments described herein for producing D-lactic acid, D-lactate salts, and/or downstream products of the D-lactic acid pathway can be adapted and/or modified in various ways and applied to L-lactic acid, L-lactate salts, and/or downstream products of the L-lactic acid pathway without departing from the spirit of this disclosure.

Fermentative Production of D-Lactic Acid, D-Lactate Salts by Recombinant Host Cells Any of the recombinant host cells of the present disclosure can be cultured to produce and/or secrete D-lactate (i.e., D-lactic acid and D-lactate salt). As disclosed herein, the D-lactate can then be esterified and distilled to generate a purified ester.

Materials and methods for the maintenance and growth of microbes, as well as fermentation conditions, are well known to practitioners of ordinary skill in the art. It is understood that consideration may be given to appropriate culture medium, pH, temperature, revival of frozen stocks, growth of seed cultures and seed trains, and requirements for aerobic, microaerobic, or anaerobic conditions, depending on the specific requirements of the host cells, the fermentation, and process flows.

The methods of producing D-lactate provided herein may be performed in a suitable fermentation broth in a suitable bioreactor such as a fermentation vessel, including but not limited to a culture plate, a flask, or a fermenter. Further, the methods can be performed at any scale of fermentation known to support microbial production of small-molecules on an industrial scale. Any suitable fermenter may be used including a stirred tank fermenter, an airlift fermenter, a bubble column fermenter, a fixed bed bioreactor, or any combination thereof.

In some embodiments of the present disclosure, the fermentation broth is any fermentation broth in which a recombinant host cell capable of producing D-lactate according to the present disclosure, and can subsist (i.e., maintain growth, viability, and/or catabolize glucose or other carbon source). In some embodiments, the fermentation broth is an aqueous medium comprising assimilable carbon, nitrogen, and phosphate sources. Such a medium can also comprise appropriate salts, minerals, metals, and other nutrients. In some embodiments, the carbon source and each of the essential cell nutrients are provided to the fermentation broth incrementally or continuously, and each essential cell nutrient is maintained at essentially the minimum level for efficient assimilation by growing cells. For example, cell growth procedures comprise batch fermentation, fed-batch fermentation with batch separation, fed-batch fermentation with continuous separation, and continuous fermentation with continuous separation. These procedures are well known to practitioners of ordinary skill in the art.

In some embodiments of the present disclosure, the handling and culturing of recombinant host cells to produce D-lactate may be divided up into phases, such as growth phase, production phase, and/or recovery phase. The following paragraphs provide examples of features or purposes that may relate to these different phases. These features or purposes may vary based on the recombinant host cells used, the desired D-lactate yield, titer, and/or productivity, or other factors. While it may be beneficial in some embodiments for the D-lactic acid pathway enzymes, ancillary proteins and/or endogenous host cell proteins to be constitutively expressed, other embodiments, may comprise selective expression or repression of any or all of the aforementioned proteins.

During growth phase, recombinant host cells may be cultured to focus on growing cell biomass by utilizing the carbon source provided. In some embodiments, expression of D-lactic acid pathway enzymes and/or ancillary proteins are repressed or uninduced. In some embodiments, no appreciable amount of D-lactate is made. In some embodiments, proteins that contribute to cell growth and/or cellular processes may be selectively expressed.

During production phase, however, recombinant host cells may be cultured to stop producing cell biomass and to focus on D-lactate biosynthesis by utilizing the carbon source provided. In some embodiments, D-lactic acid pathway enzymes, and/or ancillary proteins may be selectively expressed during production to generate high product titers, yields and productivities. The production phase is synonymous with fermentation, fermentation run or fermentation phase.

In some embodiments, the growth and production phases take place at the same time. In other embodiments, the growth and production phases are separate. While in some embodiments, product is made exclusively during production phase, in other embodiments some product is made during growth phase before production phase begins.

The recovery phase marks the end of the production phase, during which cellular biomass is separated from fermentation broth and D-lactate is purified from fermentation broth. In some fermentation process, for example, fill-draw and continuous fermentations, there may be multiple recovery phases where fermentation broth containing biomass and D-lactic acid are removed from the fermentation system. The draws of fermentation broth may be processed independently or may be stored, pooled, and processed together. In other fermentation processes, for example, batch and fed-batch fermentations, there may be a single recovery phase.

Fermentation procedures are particularly useful for the biosynthetic production of commercial D-lactate. Fermentation procedures can be scaled up for manufacturing D-lactate and fermentation procedures comprise, for example, fed-batch fermentation and batch product separation; fed-batch fermentation and continuous product separation; batch fermentation and batch product separation; and continuous fermentation and continuous product separation.

Carbon Source

The carbon source provided to the fermentation can be any carbon source that can be fermented by recombinant host cells. Suitable carbon sources include, but are not limited to, monosaccharides, disaccharides, polysaccharides, glycerol, acetate, ethanol, methanol, methane, or one or more combinations thereof. Monosaccharides suitable for use in accordance to the methods of the present disclosure include, but are not limited to, dextrose (glucose), fructose, galactose, xylose, arabinose, and any combination thereof. Disaccharides suitable for use in accordance to the methods of the present disclosure include, but are not limited to, sucrose, lactose, maltose, trehalose, cellobiose, and any combination thereof. Polysaccharides suitable for use in accordance to the methods of the present disclosure include, but are not limited to, starch, glycogen, cellulose, and combinations thereof. In some embodiments, the carbon source is dextrose. In other embodiments, the carbon source is sucrose. In some embodiments, mixtures of some or all the aforementioned carbon sources can be used in fermentation.

pH

The pH of the fermentation broth can be controlled by the addition of acid or base to the culture medium. In some embodiments, fermentation pH is controlled at the beginning of fermentation and then allowed to drop as D-lactic acid accumulates in the broth, minimizing the amount of base added to the fermentation (thereby improving process economics) as well as minimizing the amount of salt formed. Specifically, the pH during fermentation is maintained in the range of 2-8. At the end of fermentation, the final pH is in the range of 2-5. Non-limiting examples of suitable acids used to control fermentation pH include aspartic acid, acetic acid, hydrochloric acid, and sulfuric acid. Non-limiting examples of suitable bases used to control fermentation pH include sodium bicarbonate (NaHCO$_3$), sodium hydroxide (NaOH), potassium bicarbonate (KHCO$_3$), potassium hydroxide (KOH), calcium hydroxide (Ca(OH)$_2$), calcium carbonate (CaCO$_3$), ammonia, ammonium hydroxide, and diammonium phosphate. In some embodiments, a concentrated acid or concentrated base is used to limit dilution of the fermentation broth.

Base cations and D-lactate anions react to form ionic compounds in fermentation broths. For example, base Na+ cations and D-lactate anions react to form sodium D-lactate. In some embodiments, the ionic compounds formed by base cations and D-lactate anions are soluble in fermentation broth. In other embodiments, the ionic compounds formed by base cations and D-lactate anions are insoluble salts and may crystallize in the fermentation broth.

Temperature

The temperature of the fermentation broth can be any temperature suitable for growth of the recombinant host cells and/or production of D-lactic acid. In some embodiments, during D-lactic acid production, the fermentation broth is maintained within a temperature range of from about 20° C. to about 45° C., or in the range of from about 30° C. to about 42° C.

Oxygen/Aeration

The present disclosure provides methods to achieve high D-lactic acid yields, titers, and productivities under aerobic conditions. Typically, lactic acid (D- or L-) can only be efficiently produced under anaerobic or microaerobic fermentation conditions. Under aerobic conditions, microbes will commonly use molecular oxygen as an electron acceptor to reoxidize NAD(P)H cofactors in the electron transport chain of the mitochondria, generating ATP useful for growth and maintenance of cellular functions. In the absence of oxygen, microbes can only reoxidize the NAD(P)H resulting from glycolysis through the activity of product pathways that are redox balanced, one of which is production of D-lactic acid from glucose. There are several downsides to anaerobic (or oxygen limited) production of lactic acid. First, glucose consumption rates are lower, leading to lower fermentation productivities. Second, insufficient ATP is generated to concomitantly maintain cellular activities, export lactic acid, support high lactic acid titers, and support pathway activity under low pH fermentation conditions. Thus, it would be advantageous to produce lactic acid under aerobic conditions where the ATP generated from aerobic respiration can be used to increase fermentation metrics. For example, aerobically generated ATP can be used by the cell to tolerate higher D-lactic acid titers and lower fermentation pH ranges, which translate to achieving higher D-lactic acid yields, titers, and/or productivities as compared to anaerobic or oxygen-limited fermentations.

As described previously, the D-lactic acid pathway is redox balanced (i.e., conversion of glucose to D-lactic acid results in no net NAD(P)H). Thus, in recombinant host cells comprising deletion or disruption of the external NAD(P)H dehydrogenase responsible for passing electrons from cytosolic NAD(P)H into the electron transport chain, and expression of a DLDH in the cytosol, the primary route for the cell to reoxidize cytosolic NAD(P)H is through lactic acid production. Additional genetic modifications can be introduced into recombinant host cells to modulate the flux of TCA cycle substrates (typically pyruvate) into the mitochondria, where the TCA cycle substrates are aerobically respired to carbon dioxide along with concomitant generation of NADH (and potentially other redox cofactors) through the activity of the electron transport chain. Thus, by controlling the flux of TCA cycle substrates into the mitochondria, the amount of glucose aerobically respired to carbon dioxide can be controlled such that sufficient ATP is generated to support high lactic acid titers and/or productivities without detracting from lactic acid yields from glucose.

During cultivation, aeration and agitation conditions are selected to produce an oxygen transfer rate (OTR; rate of dissolution of dissolved oxygen in a fermentation medium) that results in high D-lactic acid titers at low final fermentation pH values. In various embodiments, fermentation conditions are selected to produce an OTR of greater than 5 mmol/L/hr. In some embodiment, fermentation conditions are selected to produce an OTR of greater than 10 mmol/L/hr, 20 mmol/L/hr, 30 mmol/L/hr, 40 mmol/L/hr, 50 mmol/L/hr, 75 mmol/L/hr, 100 mmol/L/hr, 125 mmol/L/hr, 150 mmol/L/hr, 175 mmol/L/hr, or 200 mmol/L/hr. OTR as used herein refers to the volumetric rate at which oxygen is consumed during the fermentation. Inlet and outlet oxygen concentrations can be measured by exhaust gas analysis, for example by mass spectrometers. OTR can be calculated using the Direct Method described in Bioreaction Engineering Principles 3$^{rd}$ Edition, 2011, Spring Science+Business Media, p. 449. The recombinant host cells of the present disclosure are able to produce D-lactic acid under a wide range of oxygen concentrations.

Yields and Titers

A high yield of D-lactate from the provided carbon source(s) is desirable to decrease the production cost. As used herein, yield is calculated as the percentage of the mass of carbon source catabolized by recombinant host cells of the present disclosure and used to produce D-lactate. In some cases, only a fraction of the carbon source provided to a fermentation is catabolized by the cells, and the remainder is found unconsumed in the fermentation broth or is consumed by contaminating microbes in the fermentation. Thus, it is important to ensure that fermentation is both substantially pure of contaminating microbes and that the concentration of unconsumed carbon source at the completion of the fermentation is measured. For example, if 100 grams of glucose is fed into the fermentation, and at the end of the fermentation 25 grams of D-lactic acid are produced and there remains 10 grams of glucose, the D-lactate yield is 27.7% (i.e., 25 grams D-lactate from 90 grams glucose). In certain embodiments of the methods provided herein, the final yield of D-lactic acid on the carbon source is at least 10%, at least 20%, at least 30%, at least 35%, at least 40%, at least 50%, at least 60%, at least 70%, at least 80%, or greater than 80%. In certain embodiments, the recombinant host cells provided herein are capable of producing at least 70%, at least 75%, or greater than 80% by weight of carbon source to D-lactate. When a D-lactate salt is found in the fermentation broth, the D-lactic acid yield can be determined by calculating the mols of D-lactate salt present and adjusting for the molecular weight difference between the D-lactate salt and D-lactic acid.

In addition to yield, the titer (or concentration), of D-lactate produced in the fermentation is another useful metric for production. Generally speaking, titer is provided as grams of product (for example, D-lactate) per liter of fermentation broth (i.e., g/L). In some embodiments, the lactic acid titer is at least 1 g/L, at least 5 g/L, at least 10 g/L, at least 15 g/L, at least 20 g/L, at least 25 g/L, at least 30 g/L, at least 40 g/L, at least 50 g/L, at least 60 g/L, at least 70 g/L, at least 80 g/L, at least 90 g/L, at least 100 g/L, at least 125 g/L, at least 150 g/L, or greater than 150 g/L at some point during the fermentation, or at the conclusion of the fermentation. In some embodiments, the D-lactic acid titer at the conclusion of the fermentation is greater than 100 g/L. In some embodiments, the D-lactic acid titer at the conclusion of the fermentation is greater than 125 g/L. In some embodiments, the D-lactic acid titer at the conclusion of the fermentation is greater than 150 g/L. As with yield calculations, a D-lactic acid titer can be calculated from the D-lactate salt titer by adjusting for molecular weight differences between the D-lactate salt and D-lactic acid.

Further, productivity, or the rate of product (i.e., D-lactate) formation, is useful for decreasing production cost. Generally speaking, productivity is provided as grams product produced per liter of fermentation broth per hour (i.e., g/L/hr). In some embodiments, D-lactic acid productivity is at least 0.1 g/L/hr, at least 0.25 g/L/hr, at least 0.5 g/L/hr, at least 0.75 g/L/hr, at least 1.0 g/L/hr, at least 1.25 g/L/hr, at least 1.25 g/L/hr, at least 1.5 g/L/hr, at least 2.0 g/L/hr, at least 3.0 g/L/hr, at least 4.0 g/L/hr, at least 5.0 g/L/hr, at least 6.0 g/L/hr or greater than 6.0 g/L/hr over some time period during the fermentation. In some embodiments, the D-lactic acid productivity is at least 3 g/L/hr. In some embodiments, the D-lactic acid productivity is at least 4 g/L/hr. In some embodiments, the D-lactic acid productivity is at least 5 g/L/hr.

HPLC is an appropriate method to determine the amount of D-lactate and/or produced, the amount of any byproducts produced (for example, organic acids and alcohols), the amount of any pathway metabolite or intermediate produced, and the amount of unconsumed glucose left in the fermentation broth. Aliquots of fermentation broth can be isolated for analysis at any time during fermentation, as well as at the end of fermentation. Briefly, molecules in the fermentation broth are first separated by liquid chromatography (LC); then, specific liquid fractions are selected for analysis using an appropriate method of detection (for example, UV-VIS, refractive index, and/or photodiode array detectors). In some embodiments of the present disclosure, an organic acid salt (for example, D-lactate) is the fermentative product present in the fermentation broth. The salt is acidified before or during HPLC analysis to produce D-lactic acid. Hence, the acid concentration calculated by HPLC analysis can be used to calculate the salt titer in the fermentation broth by adjusting for difference in molecular weight between the two compounds.

Gas chromatography-mass spectrometry (GC-MS) is also an appropriate method to determine the amount of target product and byproducts, particularly if they are volatile. Samples of fermentation can be isolated any time during and after fermentation and volatile compounds in the headspace can be extracted for analysis. Non-volatile compounds in the fermentation medium (for example, organic acids) can also be analyzed by GC-MS after derivatization (i.e., chemical alteration) for detection by GC-MS. Non-volatile compounds can also be extracted from fermentation medium by sufficiently increasing the temperature of the fermentation medium, causing non-volatile compounds to transition into gas phase for detection by GC-MS. Molecules are carried by an inert gas carries as they move through a column for separation and then arrive at a detector.

Purification of D-Lactic Acid and D-Lactate Salts

The present disclosure describes the methods for purifying and analyzing fermentation product synthesized by recombinant cells of the present disclosure, wherein the fermentation product comprises D-lactic acid and D-lactates. The methods comprise separating soluble fermentation product from fermentation broth, cells, cell debris and soluble impurities, and isolating the soluble fermentation product. The fermentation product is analyzed for relative amounts of D- and L-lactic acid enantiomers. In some examples, the methods may also comprise converting fermentation product from soluble form to insoluble, crystalline form, and isolating the crystalline fermentation product. The embodiments described herein for the purification of D-lactic acid and D-lactate salts can be adapted and/or modified in various ways and applied to L-lactic acid and L-lactate salts without departing from the spirit of this disclosure.

At the end of fermentation, the fermentation broth contains fermentation product, in soluble and/or insoluble forms, together with biomass and soluble impurities that comprise salts, proteins, unconverted sugars, and other impurities including color bodies. Biomass and soluble impurities are removed via a series of purification steps. In certain embodiments of the present disclosure, purification steps may comprise centrifugation, microfiltration, ultrafiltration, nanofiltration, diafiltration, ion exchange, crystallization, and any combination thereof. In some of these embodiments, ion exchange resins and nanofiltration membranes are used as polishing steps to remove trace amounts of soluble impurities, unconverted sugars and color bodies.

Removal of Cells and Cell Debris

In some embodiments, the process of purifying fermentation product (i.e., D-lactic acid and D-lactates) comprises a step of separating a liquid fraction containing fermentation product from a solid fraction that contains cells and cell debris. For this separation, any amount of fermentation broth can be processed, including the entirety of the fermentation broth. One skilled in the art will recognized the amount of fermentation broth processed can depend on the type of fermentation process used, such as batch or continuous fermentation processes. In various embodiments, removal of cells and cell debris can be accomplished, for example, via centrifugation using specific g-forces and residence times, and/or filtration using molecular weight cutoffs that are suitable for efficiently separating the liquid fraction containing fermentation product from the solid fraction that contains cells and cell debris. In some embodiments, removal of cells and cell debris is repeated at least once at one or in more than one step in the methods provided herein.

In some embodiments, centrifugation is used to provide a liquid fraction comprising fermentation product that is substantially free of cells. Many types of centrifuges useful for the removal of cells and solids from fermentation broth are known to those skilled in the art, including disc-stack and decanter centrifuges. Centrifuges are well suited for separating solids with a particle size of between 0.5 µm to 500 µm and density greater than that of the liquid phase (ca. 1.0 g/mL). Yeast cells, as a non-limiting example of a fermentation product-producing microbe, typically have a particle size between 4-6 µm and a density of around 1.1 g/mL; therefore, centrifugation is well suited for removing yeast cells from fermentation broth.

In some embodiments, a disc-stack centrifuge is used to provide a liquid fraction comprising fermentation product that substantially free of cells. A disc stack centrifuge separates solids, which are discharged intermittently during operation, from liquids, typically in a continuous process. A disc-stack centrifuge is well suited for separating soft, non-abrasive solids, including cells. In some embodiments, a decanter centrifuge is used to provide a liquid fraction comprising fermentation product that is substantially free of cells. A decanter centrifuge can typically process larger amounts of solids and is often used instead of a disc-stack centrifuge for processing fermentation broth when the cell mass and other solids exceeds about 3% w/w.

Other methods can be used in addition to, or alone, with the above centrifugation processes. For example, microfiltration is also an effective means to remove cells from fermentation broth. Microfiltration comprises filtering the fermentation broth through a membrane having pore sizes from about 0.5 µm to about 5 µm. In some embodiments, microfiltration is used to provide a liquid fraction comprising fermentation product that is substantially free of cells.

In some embodiments, cells removed by centrifugation and/or microfiltration are recycled back into the fermentation. One skilled in the art will recognize recycling cells back into the fermentation can increase fermentation product yield since less carbon source (for example, glucose) will typically be used to generate new cells. Additionally, recycling cells back into the fermentation can also increase fermentation product productivity since the concentration of cells producing D-lactic acid and/or D-lactate in the fermenter can be increased.

While suitable for removing cells, centrifugation and microfiltration are not generally effective at removing cells debris, proteins, DNA and other smaller molecular weight compounds from the fermentation broth. Ultrafiltration is a process similar to microfiltration, but the membrane has pore sizes ranging from about 0.005 µm to 0.1 µm. This pore size equates to a molecular weight cut-off (the size of macromolecule that will be ca. 90% retained by the membrane) from about 1,000 Daltons to about 200,000 Daltons. The ultrafiltration permeate will contain low-molecular weight compounds, including fermentation product and various other soluble salts while the ultrafiltration retentate will contain the majority of residual cell debris, DNA, and proteins. In some embodiments, ultrafiltration is used to provide a liquid fraction comprising D-lactate salts that is substantially free of cell debris and proteins.

Nanofiltration and Ion Exchange Polishing of Clarified Fermentation Broth Containing Fermentation Product In some embodiments, nanofiltration is used to separate out certain contaminating salts, sugars, color forming bodies, and other organic compounds present in clarified fermentation broth containing fermentation product (i.e., D-lactic acid and D-lactates). In nanofiltration, the clarified fermentation broth (i.e., the fermentation broth resulting from the combination of centrifugation, microfiltration, and/or ultrafiltration steps described above) is filtered through a membrane having pore sizes ranging from 0.0005 µm to 0.005 µm, equating to a molecular weight cut-off of about 100 Daltons to about 2,000 Daltons. Nanofiltration can be useful for removing divalent and multivalent ions, maltose and other disaccharides (for example, sucrose), polysaccharides, and other complex molecules with a molecular weight larger than fermentation product (for example, sodium D-lactate 112.06 g/mol, magnesium D-lactate 202.45 g/mol, calcium D-lactate 218.22 g/mol, potassium D-lactate 128.17 g/mol). Non-limiting examples of nanofiltration materials include ceramic membranes, metal membranes, polymer membranes, and composite membranes.

In some embodiments, ion exchange is used to remove specific contaminating salts present in clarified fermentation broth containing fermentation product. Ion exchange elements can take the form of resin beads as well as membranes. Frequently, the resins are cast in the form of porous beads. The resins can be cross-linked polymers having active groups in the form of electrically charged sites. At these sites, ions of opposite charge are attracted but may be replaced by other ions depending on their relative concentrations and affinities for the sites. Ion exchangers can be cationic or anionic. Factors that determine the efficiency of a given ion exchange resin comprise the favorability for a given ion, and the number of active sites available.

A combination of nanofiltration and ion exchange steps can be combined to produce a purified solution of fermentation product from clarified fermentation broth.

Analysis of Fermentation Product for Relative Amounts of D- and L-Lactic Acid Enantiomers The purified solution of fermentation product (i.e., D-lactic acid and D-lactates) as described thus far are analyzed for enantiomeric purity. In some embodiments, the purified fermentation product is evaluated using a chiral gas chromatography method. Briefly, the acid and an alcohol are added to the purified solution of fermentation to produce derivatized products of lactic acid. The derivatized products of lactic acid are then prepared for analysis by gas chromatography (GC) using a flame ionization detector (FID). Separation of derivatized enantiomers is achieved using Agilent CycloSil-B chiral capillary column and standard operating procedures, or other columns with equivalent capabilities and their respective standard operating procedures. Enantiomeric purity is defined as $100\% \times \{(D\text{-enantiomer})/(D\text{-enantiomer}+L\text{-enantiomer})\}$.

Crystallization of Fermentation Product

Fermentation products (i.e., D-lactic acid and D-lactates) purified as described thus far are crystallized to further remove water and any remaining trace, water-soluble impurities. The solution of purified fermentation product as produced by the aforementioned steps is then fed to the fermentation product crystallization step. In some embodiments of the present disclosure, it is desirable to recover the majority of the D-lactic acid in the insoluble, crystallized form with a minor fraction of D-lactic acid remaining in the mother liquor.

In some embodiments of the present disclosure, the temperature of the mother liquor is changed to facilitate fermentation product crystallization. In some embodiments, the mother liquor is cooled to a temperature below 20° C. to decrease fermentation product solubility. In some these embodiments, the mother liquor is heated to evaporate excess water. In some of these embodiments, evaporative crystallization is used, as it offers a high yield of fermentation product and prevents the formation of stable gels, which may occur if temperature is reduced below the gelling point of concentrated fermentation product solutions. In some of these embodiments, fermentation product crystallization is achieved by combining various heating and cooling steps. In some of these embodiments, supersaturation is achieved by evaporative crystallization wherein the solute is more concentrated in a bulk solvent that is normally possible under given conditions of temperature and pressure; increased supersaturation of fermentation product in the mother liquor causes the fermentation product to crystallize. Non-limiting examples of crystallizers include forced circulation crystallizers, turbulence/draft tube and baffle crystallizers, induced circulation crystallizers and Oslo-type crystallizers.

In some embodiments of the present disclosure, the aforementioned heating step, cooling step and change in pH are combined in various ways to crystallize fermentation product, and modified as needed.

Fermentation product crystals can be isolated from the mother liquor by any technique apparent to those of skill in the art. In some embodiments of the present disclosure, fermentation product crystals are isolated based on size, weight, density, or combinations thereof. Fermentation product crystal isolation based on size can be accomplished, for example, via filtration, using a filter with a specific particle size cutoff. Fermentation product crystal isolation based on weight or density can be accomplished, for example, via gravitational settling or centrifugation, using, for example, a settler, decanter centrifuge, disc-stack centrifuge, basket centrifuge, or hydrocyclone wherein suitable g-forces and settling or centrifugation times can be determined using methods known in the art. In some embodiments, fermentation product crystals are isolated from the mother liquor via settling for from 30 minutes to 2 hours at a g-force of 1. In other embodiments, D-lactate salt crystals are isolated from the fermentation broth via centrifugation for 20 seconds to 60 seconds at a g-force of from 275 x-g to 1,000 x-g.

Following isolation from the mother liquor, fermentation product crystals are wet with residual mother liquor that coats the crystals. Thus, it is useful to wash the fermentation product crystals with water to remove these trace impurities that may be in the mother liquor. When washing fermentation product crystals, it is sometimes desired to minimize the dissolution of isolated crystals in the wash water; for this reason, in some embodiments, cold wash (around 4C) water is generally used. Additionally, it can be desired to minimize the amount of wash water used to minimize crystal dissolution. In many embodiments, less than 10% w/w wash water is used to wash the fermentation product crystals.

In some embodiments, the methods further comprise the step of removing impurities from fermentation product crystals. Impurities may react with fermentation product crystals and reduce final yields, or contribute to fermentation product crystals of lesser purity that limits industrial utility. Non-limiting examples of impurities include acetic acid, succinic acid, malic acid, ethanol, glycerol, citric acid, and propionic acid. In some embodiments, removal of such impurities is accomplished by dissolving the isolated fermentation product crystals into an aqueous solution and recrystallizing the fermentation product. A non-limiting example of dissolving and recrystallizing fermentation product crystals can include dissolving the fermentation product in water and evaporating the resulting aqueous solution (as mentioned above), and finally re-isolating the fermentation product crystals by filtration and/or centrifugation. None, one, or more than one cycle of fermentation product recrystallization may be used so long as the resulting fermentation product are of suitable quality for subsequent esterification. In some embodiments, no fermentation product recrystallizations are performed. In other embodiments, one fermentation product recrystallization is performed. In still further embodiments, more than one fermentation product recrystallization is performed.

In some embodiments of the present disclosure, fermentation product crystals are dewatered using a combination of screening and drying methods. In some of these embodiments, crystal dewatering steps comprise centrifugation, belt drying, filtration, application of vacuum, or a combination thereof. In some of these embodiments, vacuum is applied at 20 mm of Hg below atmospheric pressure. Suitable devices for crystal dewatering may comprise a Horizontal Vacuum Belt Filter (HVBF) or a Rotary Drum Vacuum Filter (RDVF). Fermentation product crystal isolation based on size can be accomplished, for example, via filtration, using, for example, a filter press, candlestick filter, or other industrially used filtration system with appropriate molecular weight cutoff. Fermentation product crystal isolation based on weight or density can be accomplished, for example, via gravitational settling or centrifugation, using, for example, a settler, decanter centrifuge, disc-stack centrifuge, basket centrifuge, or hydrocyclone, wherein suitable g-forces and settling or centrifugation times can be determined using methods known in the art.

In some embodiments of the present disclosure, fermentation products are crystallized in the fermentation broth prior to removal of cells, cell debris, contaminating salts and various soluble impurities. In many of these embodiments, the fermentation product crystals are separated from fermentation broth, cells, cell debris, contaminating salts and various soluble impurities by sedimentation, centrifugation, ultrafiltration, nanofiltration, ion exchange, or any combination thereof.

Lactic Acid Polymers

In certain aspects, the D-lactic acid provided herein, or a salt or derivative thereof is employed as at least one type of polymerization material to produce a lactic acid polymer. Examples of polymerization material that is employed, includes, for example, D-lactic acid, or derivatives (such as lactides), and prepolymers and oligomers resulting from polymerizing such monomers to suitable lengths. In some embodiments, the polymerization further comprises L-lactic acid or derivatives (such as lactides) and prepolymers and oligomers thereof.

Non-limiting examples of lactic acid polymers include homopolymers of D-lactic acid, hetero-block polymers, and various types of heteropolymers of lactic acid and non-lactic based polymerization material.

The lactic acid polymerization materials, or lactic acid polymerization material and another non-lactic acid polymerization material, are reacted with a suitable polymerization initiator to produce lactic acid polymers. Various Lewis acid-metal catalysts such as dioctyl stannate and the likes, and non-nucleophilic Lewis bases, such as diazabicycloundecane and the likes may be utilized as a polymerization initiator or polymerization catalyst. The polymerization is performed in solution, in a melt, or in a suspension. See for example, Garlotta, "A Literature Review of Poly(lactic) acid," Journal of Polymers and the Environment, 2001, vol. 9, no. 2, pages 63-84.

EXAMPLES

Parent Strain Used in the Examples

The parent strain in Example 1 was a *P. kudriavzevii* strain auxotrophic for histidine and uracil due to genetic disruptions in URA2 and HIS3 (i.e., the strain cannot grow in media without histidine and uracil supplementation). Histidine auxotrophy in the parent strain enables selection of new, engineered strains that carry a HIS3 marker, enabling histidine prototrophy and indicating desired nucleic acid modification. Likewise, uracil auxotrophy in the parent strain enables selection of new, engineered strains that carry a URA2 marker, enabling uracil prototrophy and indicating desired nucleic acid modification. Thus, cells that were successfully modified with exogenous nucleic acids to comprise desired genetic modifications can grow in media without histidine and/or uracil supplementation, dependent on the selection marker included in the exogenous nucleic acid. Following confirmation of correct strain engineering, the selection marker(s) were removed by, for example, homologous recombination and marker loopout. Removing the marker enables subsequent rounds of strain engineering using the same selection markers.

Media Used in the Examples
Complete Supplement Mixture (CSM) Medium.
CSM medium comprised Adenine 10 mg/L; L-Arginine HCl 50 mg/L; L-Aspartic Acid 80 mg/L; L-Histidine HCl 20 mg/L; L-Isoleucine 50 mg/L; L-Leucine 100 mg/L; L-Lysine HCl 50 mg/L; L-Methionine 20 mg/L; L-Phenylalanine 50 mg/L; L-Threonine 100 mg/L; L-Tryptophan 50 mg/L; L-Tyrosine 50 mg/L; Uracil 20 mg/L; L-Valine 140 mg/L. The YNB used in the CSM comprised Ammonium sulfate 5.0 g/L, Biotin 2.0 µg/L, Calcium pantothenate 400 µg/L, Folic acid 2.0 µg/L, Inositol 2.0 mg/L, Nicotinic acid 0-400 µg/L, p-Aminobenzoic acid 200 µg/L, Pyridoxine HCl 400 µg/L, Riboflavin 200 µg/L, Thiamine HCl 400 µg/L, Boric acid 500 µg/L, Copper sulfate 40 µg/L, Potassium iodide 100 µg/L, Ferric chloride 200 µg/L, Manganese sulfate 400 µg/L, Sodium molybdate 200 µg/L, Zinc sulfate 400 µg/L, Potassium phosphate monobasic 1.0 g/L, Magnesium sulfate 0.5 g/L, Sodium chloride 0.1 g/L, and Calcium chloride 0.1 g/L.

Complete Supplement Mixture Minus Histidine (CSM-his) Medium.
CSM-His medium is identical to CSM medium with the exception that histidine was not included in the medium. Engineered strains auxotrophic for histidine are unable to grow on CSM-His medium while engineered strains containing exogenous nucleic acids comprising a histidine selectable marker (for example, HIS3) are capable of growth in CSM-His medium.

Complete supplement mixture minus uracil (CSM-Ura) medium. CSM-Ura medium is identical to CSM medium with the exception that uracil was not included in the medium. Engineered strains auxotrophic for uracil are unable to grow on CSM-Ura medium while engineered strains containing exogenous nucleic acids comprising a uracil selectable marker (for example, URA2) are capable of growth in CSM-Ura medium.

BM02 Medium.
BM02 medium is Glucose 125 g/L, $K_2SO_4$ 0.816 g/L, $Na_2SO_4$ 0.1236, $MgSO_4 \cdot 7H_2O$ 0.304 g/L, Urea 4.3 g/L, Myo-inositol 2 mg/L, Thiamin HCl 0.4 mg/L, Pyridoxal HCl 0.4 mg/L, Niacin 0.4 mg/L, Ca-Pantothenate 0.4 mg/L, Biotin µg/L, Folic acid 2 µg/L, PABA 200 µg/L, Riboflavin 200 µg/L, Boric acid 0.25 mg/L, Copper sulfate pentahydrate 393 µg/L, Iron sulfate 11.0 mg/L, Manganese chloride 1.6 mg/L, Sodium molybdate 100 µg/L, Zinc sulfate 4 mg/L, and EDTA 11 mg/L.

BM02-P Medium.
BM02-P medium is BM02 medium with 1 g/L potassium phosphate.

YPE Medium.
YPE medium is Bacto peptone 20 g/L, Yeast extract 10 g/L, and Ethanol 2% (v/v).

Example 1: Construction of Recombinant *P. kudriavzevii* Strain, LPK15779, with Eliminated Expression of Pyruvate Decarboxylase Example 1 describes the construction of a pyruvate decarboxylase (PDC) minus *P. kudriavzevii*, LPK15779, wherein all three PDC genes, i.e., Pdc1, Pdc5 and Pdc6, were genetically disrupted to eliminate expression of PkPDC1 (SEQ ID NO: 11), PkPDC5 (SEQ ID NO: 12), and PkPDC6 (SEQ ID NO: 13).

The parent *P. kudiavzevii* strain used in this example was auxotrophic for uracil and histidine. To eliminate PDC expression, the Pdc1, Pdc5 and Pdc6 genes in the *P. kuiavzevii* genome were disrupted sequentially. The *P. kudiavzevii* strain was diploid and two copies of each pyruvate decarboxylase gene were present at the indicated locus; therefore, disruption of each gene was achieved by deleting of both gene copies.

A URA3 selectable marker, amplified by PCR, was provided to the parent *P. kudiavzevii* strain to complement the uracil auxotrophic deficiency. The URA3 selectable marker comprised unique upstream and downstream homologous regions for homologous recombination at the *P. kudiavzevii* Pdc1 locus, a transcriptional promoter, a URA3 coding region, and a transcriptional terminator. The transcriptional promoter 5' of URA3 was the *P. kudiavzevii* TEF1 promoter (pPkTEF1) and the transcriptional terminator 3' of URA3 was the *S. cerevisiae* TDH3 terminator (tScTDH3). The PCR product of the URA3 selectable marker was gel-purified and provided as exogenous nucleic acids to *P. kudriavzevii*. Transformation was carried out in a single step and gene deletion was achieved by homologous recombination. Transformants were selected on CSM-Ura medium and successful deletion of both copies of the gene encoding PkPDC1 was confirmed by genetic sequencing of this locus and the flanking regions. After successful construction of a recombinant *P. kudiavzevii* comprising a Pdc1 genetic disruption, the URA3 selectable marker was removed from the recombinant strain genome by recombination and marker loopout.

The URA3 selectable marker and genetic disruption strategy described above were reused to next disrupt the Pdc5 and Pdc6 genes in succession. Deletion of the native genes encoding PkPDC5 and PkPDC6 was confirmed by genetic sequencing of this locus and the flanking regions. The *P. kudiavzevii* strain that results from Example 1, LPK15779, was without any URA3 selectable marker. The URA3 selectable marker was absent in the following examples that describe further strain engineering or strain performance testing. Thus, Example 1 produces a PDC minus (i.e., comprises deletion of native genes encoding PkPDC1, PkPDC5, and PkPDC6), uracil and histidine auxotrophic *P. kudiavzevii*, which was the background strain for Example 2 below.

Example 2: Construction of Recombinant *P. kudriavzevii* Background Strain, LPK15942, with Eliminated Expression of Pyruvate Decarboxylase and Pyruvate Dehydrogenase Complex Example 2 describes the construction of a pyruvate dehydrogenase complex (PDH) minus *P. kudiavzevii*, LPK15942, wherein expression of PDH was eliminated via genetic disruption of the Pda1 gene. Pda1 encodes for the E1 α-subunit (PkPDA1; SEQ ID NO: 14) of the PDH. When PkPDA1 expression is eliminated, PDH cannot assemble into a functional complex. Thus, PDH expression is also eliminated and the recombinant host cell is unable to catalyze the conversion of pyruvate, coenzyme A and $NAD^+$ to acetyl-CoA, $CO_2$ and NADH in the host cell mitochondria. This genetic disruption has the end result of decreasing respiration, thereby decreasing formation of byproduct $CO_2$ and increasing D-lactic acid production.

PkPDA1 was genetically disrupted using the same engineering strategy as described above in Example 1. LPK15779, a PDC minus, uracil and histidine auxotrophic *P. kuiavzevii* strain from Example 1 was the background strain used in Example 2.

A HIS3 selectable marker, amplified by PCR, was provided to the background strain (from Example 1) to complement the histidine auxotophic deficiency. The HIS3 selectable marker comprised unique upstream and downstream homologous regions for homologous recombination at the Pda1 locus of the background strain genome, a transcriptional promoter, a HIS3 coding region, and a transcriptional terminator. The transcriptional promoter 5' of HIS3 was the *P. kudiavzevii* TEF1 promoter (pPkTEF1) and the transcriptional terminator 3' of HIS3 was the *S. cerevisiae* TDH3 terminator (tScTDH3). The PCR product of the HIS3 selectable marker was gel-purified and provided as exogenous nucleic acids to the background strain. Transformation was carried out in a single step and gene deletion was achieved by homologous recombination. Transformants were selected on CSM-His medium and successful deletion of both copies of the genes encoding PkPDA1 was confirmed by genetic sequencing of this locus and the flanking regions. After successful construction of a recombinant *P. kudiavzevii* comprising a Pda1 genetic disruption, the HIS3 selectable marker was removed from the recombinant strain genome by recombination and marker loopout.

The *P. kudiavzevii* strain that resulted from Example 2, LPK15942, was without a HIS3 selectable marker. The HIS3 selectable marker was absent in the following examples that describe further strain engineering or strain performance testing. Example 2 produced a PDC minus, PDH minus, uracil and histidine auxotrophic *P. kudiavzevii* (i.e., the strain comprised deletion of native genes encoding PkPDC1, PkPDC5, PkPDC6, and PkPDA1), which was the background strain used in Example 3.

Example 3: Construction of Recombinant *P. kudiavzevii* Strain, LPK151316, with Eliminated Expression of the Mitochondrial External NADH Dehydrogenase Example 3 describes the construction of a mitochondrial external NADH dehydrogenase (NDE1) minus *P. kudiavzevii*, LPK151316, wherein expression of NDE1 was eliminated via genetic disruption of the Nde1 gene. When PkNDE1 (SEQ ID NO: 16) expression is eliminated, the recombinant host cell is unable to oxidize NAD(P)H to NAD(P)$^+$, thus not competing with the D-lactic acid pathway for NAD(P)H, which is utilized by the D-lactic acid pathway to make D-lactic acid. This genetic disruption has the end result of increased D-lactic acid product formation.

PkNDE1 was genetically disrupted using the same engineering strategy as described in Examples 1 and 2. LPK15942, a PDC minus, PDH minus, and uracil auxotrophic *P. kudiavzevii* from Example 2 was the background strain used in Example 3.

A HIS3 selectable marker, amplified by PCR, was provided to the background strain (from Example 2) to complement the histidine auxotrophic deficiency. The HIS3 selectable marker comprised unique upstream and downstream homologous regions for homologous recombination at the Pda1 locus of the background strain genome, a transcriptional promoter, a HIS3 coding region, and a transcriptional terminator. The transcriptional promoter 5' of HIS3 was the *P. kudiavzevii* TEF1 promoter (pPkTEF1) and the transcriptional terminator 3' of HIS3 was the *S. cerevisiae* TDH3 terminator (tScTDH3). The PCR product of the HIS3 selectable marker was gel-purified and provided as exogenous nucleic acids to the background strain. Transformation was carried out in a single step and gene deletion was achieved by homologous recombination. Transformants were selected on CSM-His medium and successful deletion of both copies of genes encoding PkNDE1 was confirmed by genetic sequencing of this locus and the flanking regions. After successful construction of a recombinant *P. kudiavzevii* comprising a Nde1 genetic disruption, the HIS3 selectable marker was removed from the recombinant strain genome by recombination and marker loopout.

The *P. kudiavzevii* strain that resulted from Example 3, LPK151316, was without a HIS3 selectable marker. The HIS selectable marker was absent in the following examples that describe further strain engineering or strain performance testing. Example 3 produced a PDC minus, PDH minus, NDE1 minus, uracil and histidine auxotrophic *P. kudiavzevii* (i.e., the strain comprised deletion of native genes encoding PkPDC1, PkPDC5, PkPDC6, PkPDA1, and PkNDE1), which was the background strain used in Example 5.

Example 4: Recombinant *P. kudriavzevii* Background Strain, LPK151316, does not Naturally Produce D-Lactic Acid Example 4 describes the culturing and analysis of LPK151316 (from Example 3) for D-lactic acid production before LPK151316 was used as the background strain for genomic integration of the D-lactic acid pathway (Example 5). LPK151316 colonies are used to inoculate replicate tubes of 15 mL of YPE medium and are incubated at 30° C. with 80% humidity and shaking at 250 rpm for 20 hours. These replicate tubes of pre-cultures are used to inoculate baffled flask replicates of 250 mL of BM02-*P. media* with 10% glucose, 1% ethanol and 40 g/L CaCO$_3$. Pre-cultures are diluted 50× with 1 M HCl for OD$_{600}$ measurements to inform appropriate dilution of pre-cultures to produce a starting culture biomass of 1 g/L dry cell weight (DCW). Baffled flask cultures are then incubated at 30° C. with 80% humidity and shaking at 250 rpm. After 48 hours, the cultures are diluted 10× with 12 M HCl, spin-filtered and frozen for storage. Samples are analyzed by HPLC within 48 hours of harvest.

For HPLC analysis, frozen samples are thawed analyzed by HPLC using a Bio-Rad Aminex 87H column (300×7.8 mm) and a Bio-Rad Fermentation Monitoring column (#1250115; 150×7.8 mm) installed in series, with an isocratic elution rate of 0.8 mL/min with water at pH 1.95 (with sulfuric acid) at 30° C. Refractive index and UV 210 nm measurements are acquired for 35 minutes.

The LPK151316 background strain does not produce detectable amounts of D-lactic acid. Thus, all engineered *P. kudiavzevii* strains built from this background strain are incapable of producing D-lactic acid without the heterologous nucleic acids that encode the D-lactic acid pathway (Example 5).

Example 5: Construction of Recombinant *P. kudriavzevii* Strains LPK152541 and LPK152542, Wherein Each Strain Comprised an Enzyme that Converts Pyruvate to D-Lactic Acid Example 5 describes the construction of recombinant *P. kudriavzevii* host cells of the present disclosure wherein each strain comprised heterologous nucleic acids encoding an enzyme of the D-lactic acid pathway capable of carrying out the activity of the DLDH; LPK152541 comprised the DLDH from *Leuconostoc mesenteroides* subsp. *mesenteroides* (abbv. LmLDH2; UniProt ID: Q03VC9; SEQ ID NO: 2) and LPK152542 comprised the DLDH from *Lactobacillus delbrueckii* subsp. *bulgaricus* (abbv. LhDLDH; UniProt ID: P30901; SEQ ID NO: 4). In each strain, insertion of the heterologous nucleic acids encoding the DLDH genetically disrupts both copies of PkADH6C, i.e., producing a ADH6C minus phenotype.

The PkPDC1, PkPDC5, PkPDC6, PkPDA1, PkNDE1, and uracil and histidine auxotrophic *P. kudriavzevii*, LPK151316 from Example 3 was the background strain used in this example.

The heterologous nucleic acids used in this example were codon-optimized for yeast and were synthesized and provided by Twist Bioscience; each gene was cloned into its own entry vector, pEV, along with an upstream transcriptional promoter and a downstream transcriptional terminator. The transcriptional terminators cloned in from (5') of each gene were constitutive and derived from *P. kudiavzevii*. The transcriptional terminators cloned behind (3') of each gene were derived from *S. cerevisiae*. For LmDLDH2 and LhDLDH, the promoter and terminator were the *P. kudia-* vzevii TDH1 promoter (pPkTDH1) and the *S. cerevisiae* TEF1 terminator (tScTEF1), respectively. Additionally, a HIS3 marker was included in the heterologous expression cassette to complement the histidine auxotrophic deficiency in the parent strain. This HIS3 marker comprised a transcriptional promoter, a HIS3 coding region, and a transcriptional terminator. The transcriptional promoter 5' of HIS3 was the *P. kudiavzevii* TEF1 promoter (pPkTEF1) and the transcriptional terminator 3' of HIS3 was the *S. cerevisiae* TDH3 terminator (tScTDH3).

All PCR products were purified and provided as exogenous nucleic acids to *P. kudriavzevii*. Transformation was carried out in a single step. Transformants were selected on CSM-His medium. Successful integration of all heterologous nucleic acids encoding the first two D-lactic acid pathway enzymes as well as deletion of both copies of the genes encoding PkADH6C were confirmed by genetic sequencing of this locus and the flanking regions.

Example 5 produced recombinant host cells that comprised heterologous nucleic acids encoding an enzyme of the D-lactic acid pathway, and further comprised genetic disruption of PkPDC1, PkPDC5, PkPDC6, PkPDA1, PkNDE1, and PkADH6C. The resulting strains were additionally auxotrophic for uracil and histidine. The recombinant host cells that result from Example 5 were designated LPK152541 and LPK152542.

Example 6: Recombinant *P. kudriavzevii* Strains LPK152541 and LPK152542 Produced Increased Amounts of D-Lactic Acid Example 6 describes the culturing and analysis of recombinant host cells LPK152541 and LPK152542 from Example 5. Both recombinant strains were cultured and analyzed by HPLC according to methods described above in Example 4.

All recombinant strains with a D-lactic acid pathway produced 20-30 g/L of D-lactic acid as compared to the background strain LPK151316 which does not produce D-lactic acid (see description in Example 4). This example demonstrates, in accordance with the present disclosure, the expression of heterologous nucleic acids encoding a D-lactic acid pathway in recombinant *P. kudriavzevii* with increased D-lactic acid yields as compared to a host cell lacking the heterologous D-lactic acid pathway but otherwise genetically identical. HPLC analysis also revealed that >92% of total lactic acid produced (i.e., both L- and D-enantiomers) were D-lactic acid. This example demonstrates, in accordance with the present disclosure, the expression of heterologous nucleic acids encoding a D-lactic acid pathway in recombinant *P. kudriavzevii* increased D-lactic acid yields as compared to a host cell lacking the heterologous D-lactic acid pathway but is otherwise genetically identical. Samples of culture broth from LhLDH (an L-lactic acid producing control), DLDH2 (strain LPK152541) and DLDH3 (strain LPK152542) were analyzed by chiral GC-MS to determine the enantiomeric purity of the lactic acid produced (see Table 5).

TABLE 5

Proportion of D- and L- Lactic Acid In Culture Broth

| LDH enzyme | L-Lactate (%) | D-Lactate (%) |
|---|---|---|
| LhLDH | 98.50 | 1.50 |
| DLDH2 | 7.30 | 92.70 |
| DLDH3 | 1.84 | 98.16 |

This data demonstrates that the DLDH2 and DLDH3 enzymes produce the D-isomer of lactic acid.

Example 7. Screening of Additional Wild-Type And Mutated DLDH Enzymes in Vivo

In experiments similar to those described above, more DLDH enzyme candidates as well as some mutants of DLDH2 and DLDH3 were assayed. As previously, codon-optimized synthetic genes encoding the enzymes were obtained from a commercial provider, or mutations were introduced in DLDH2 or DLDH3 by conventional techniques; the new DLDH candidates were introduced in strain LPK151316 as described above, and the resulting strains were tested for lactic acid production as above. A summary of the enzymes tested and the production results are tabulated in Table 6, below. An asterisk (*) following the UniProt ID indicates amino acid point mutations were introduced and are provided in the subsequent, Mutations, column.

TABLE 6

Lactic Acid Production With Wild-Type And Mutated D-LDH Candidates. Yield is calculated for the "production-only" phase. N/A, not applicable.

| Strain ID | LDH ID | UniProt ID | Mutations | Lactic Acid titer (g/L) | Lactic Acid Yield (g/g-glucose %) |
|---|---|---|---|---|---|
| LPK152541 | DLDH2 | Q03VC9 | N/A | 42.5 | 56 |
| LPK152542 | DLDH3 | P26297 | N/A | 39.7 | 55 |
| LPK154398 | DLDH4 | P30901 | N/A | 37.3 | 58 |
| LPK154400 | DLDH7 | C0LJH4 | N/A | 34.9 | 65 |
| LPK154402 | DLDH8 | Q9I530 | N/A | 29.6 | 69 |
| LPK154404 | DLDH9 | Q8RG11 | N/A | 35.9 | 65 |
| LPK154406 | DLDH10 | E0NDE9 | N/A | 38.0 | 61 |
| LPK154408 | DLDH12 | T5JY05 | N/A | 61.8 | 73 |
| LPK154410 | DLDH13 | K0DB84 | N/A | 50.1 | 68 |
| LPK153789 | DLDH2a | Q03VC9* | Y300L | 30.7 | 54 |
| LPK153785 | DLDH2b | Q03VC9* | D175S; K176R; Y177T | 77.2 | 74 |
| LPK153780 | DLDH2d | Q03VC9* | A2345 | 51.8 | 66 |
| LPK153779 | DLDH2e | Q03VC9* | Y205Q | 47.0 | 71 |
| LPK153787 | DLDH3a | P26297* | Y301L | 35.9 | 69 |
| LPK153783 | DLDH3c | P26297* | E265G | 40.1 | 67 |
| LPK153777 | DLDH3e | P26297* | H206Q | 48.3 | 67 |

All the tested strains exhibited substantial in vivo activity. A few of the strains (for example those including DLDH12 and DLDH13) performed efficiently.

Of the mutations tested in this experiment, mutation set "b" (as in DLDH2b) also performed efficiently. Mutation set "b" may relax the affinity of the enzyme for both NAD+ and NADH while allowing the enzyme to use NADPH as well, resulting in an increase of the kinetics of the enzyme (kcat/Km) with either co-factor.

Example 8. Inactivating a Glycerol-3-Phosphate Dehydrogenase (Gpd1) Gene Increases D-Lactic Acid Production Efficiency In Vivo In this Example, the gpd1 gene was inactivated in the strain expressing DLDH3 (i.e., both GPD1 alleles were deleted from the host cell genome), and both the wild type and engineered strains were tested in a production assay as described above. The results are tabulated in Table 7, below.

TABLE 7

Positive Effect of gpd1^^ Inactivation on D-Lactic acid production. (Yield is calculated for the "production-only" phase.)

| Strain ID | Modifications | Lactic Acid titer (g/L) | Lactic Acid Yield (g/g-glucose %) |
|---|---|---|---|
| LPK152542 | DLDH3 | 40 | 55 |
| LPK152931 | DLDH3 + gpd1^^ | 52 | 72 |

This data demonstrates that inactivating gpd1 increases lactic acid production.

It should be noted that there are alternative ways of implementing the embodiments disclosed herein. Accordingly, the present embodiments are to be considered as illustrative and not restrictive; various modifications can be made without departing from the spirit of this disclosure. Furthermore, the claims are not to be limited to the details given herein and are entitled their full scope and equivalents thereof.

```
Leuconostoc mesenteroides
                                                         SEQ ID NO: 1
MKIFAYGIRD DEKPSLEEWK AANPEIEVDY TQELLTPETA KLAEGSDSAV VYQQLDYTRE     60

TLTALANVGV TNLSLRNVGT DNIDFDAARE FNFNISNVPV YSPNAIAEHS MLQLSRLLRR    120

TKALDAKIAK RDLRWAPTTG REMRMQTVGV IGTGHIGRVA INILKGFGAK VIAYDKYPNA    180

ELQAEGLYVD TLDELYAQAD AISLYVPGVP ENHHLINADA IAKMKDGVVI MNAARGNLMD    240

IDAIIDGLNS GKISDFGMDV YENEVACSMK IGLVKNSPDA KIADLIAREN VMITPHTAFY    300

TTKAVLEMVH QSFDAAVAFA KGEKPAIAVE Y                                   331

Leuconostoc mesenteroides
                                                         SEQ ID NO: 2
MKIFAYGIRD DEKPSLEEWK AANPEIEVDY TQELLTPETA KLAEGSDSAV VYQQLDYTRE     60

TLTALANVGV TNLSLRNVGT DNIDFDAARE FNFNISNVPV YSPNAIAEHS MIQLSRLLRR    120

TKALDAKIAK HDLRWAPTIG REMRMQTVGV IGTGHIGRVA INILKGFGAK VIAYDKYPNA    180

ELQAEGLYVD TLDELYAQAD AISLYVPGVP ENHHLINADA IAKMKDGVVI MNAARGNLMD    240

IDAIIDGLNS GKISDFGMDV YENEVGLFNE DWSGKEFPDA KIADLIAREN VLVTPHTAFY    300

TTKAVLEMVH QSFDAAVAFA KGEKPAIAVE Y                                   331

Lactobacillus delbrueckii
                                                         SEQ ID NO: 3
MTKIFAYAIR EDEKPFLKEW EDAHKDVEVE YTDKLLTPET VALAKGADGV VVYQQLDYTA     60

ETLQALADNG ITKMSLRNVG VDNIDMAKAK ELGFQITNVP VYSPNAIAEH AAIQAARILR    120

QDKAMDEKVA RHDLRWAPTI GREVRDQVVG VIGTGHIGQV FMQIMEGFGA KVIAYDIFRN    180

PELEKKGYYV DSLDDLYKQA DVISLHVPDV PANVHMINDE SIAKMKQDVV IVNVSRGPLV    240

DTDAVIRGLD SGKIFGYAMD VYEGEVGIFN EDWEGKEFPD ARLADLIARP NVLVTPHTAF    300

YTTHAVRNMV VKAFDNNLEL VEGKEAETPV KVG                                 333

Lactobacillus helveticus
                                                         SEQ ID NO: 4
MTKVFAYAIR KDEEPFLNEW KEAHKDIDVD YTDKLLTPET AKLAKGADGV VVYQQLDYTA     60

DTLQALADAG VTKMSLRNVG VDNIDMDKAK ELGFQITNVP VYSPNAIAEH AAIQAARVLR    120

QDKRMDEKMA KRDLRWAPTI GREVRDQVVG VVGTGHIGQV FMRIMEGFGA KVIAYDIFKN    180

PELEKKGYYV DSLDDLYKQA DVISLHVPDV PANVHMINDK SIAEMKDGVV IVNCSRGRLV    240

DTDAVIRGLD SGKIFGFVMD TYEDEVGVFN KDWEGKEFPD KRLADLIDRP NVLVTPHTAF    300

YTTHAVRNMV VKAFNNNLKL INGEKPDSPV ALNKNKF                             337

Lactobacillus pentosus
                                                         SEQ ID NO: 5
MKIIAYAVRD DERPFFDTWM KENPDVEVKL VPELLTEDNV DLAKGFDGAD VYQQKDYTAE     60

VLNKLADEGV KNISLRNVGV DNLDVPTVKA RGLNISNVPA YSPNAIAELS VTQLMQLLRQ    120

TPMFNKKLAK QDFRWAPDIA KELNTMTVGV IGTGRIGRAA IDIFKGFGAK VIGYDVYRNA    180

ELEKEGMYVD TLDELYAQAD VITLHVPALK DNYHMLNADA FSKMKDGAYI LNFARGTLID    240
```

```
SEDLIKALDS GKVAGAALVT YEYETKIFNK DLEGQTIDDK VFMNLFNRDN VLITPHTAFY    300

TETAVHNMVH VSMNSNKQFI ETGKADTQVK FD                                 332

Artificial Sequence
                                                        SEQ ID NO: 6
MKIFAYGIRD DEKPSLEEWK AAHPEIEVDY TDELLTPETA KLAEGADGVV VYQQLDYTRE     60

TLQALADAGV TKMSLRNVGT DNIDFDAAKE FGFNISNVPV YSPNAIAEHA AIQASRLLRR   120

DKALDAKIAK RDLRWAPTIG REVRMQTVGV VGTGHIGRVA MNILEGFGAK VIAYDIFKNA   180

ELEKEGLYVD SLDELYAQAD VISLHVPGVP ANHHMINADS IAKMKDGVVI VNCSRGNLVD   240

TDAVIDGLDS GKISGFVMDV YEGEVGLFNE DWEGKEFPDA RLADLIDREN VLVTPHTAFY   300

TTKAVLEMVH QSFDAALAFI NGEKPAIAVE Y                                 331

Saccharomyces cerevisiae
                                                        SEQ ID NO: 7
MSSTDEHIEK DISSRSNHDD DYANSVQSYA ASEGQVDNED LAATSQLSRH LSNILSNEEG    60

IERLESMARV ISHKTKKEMD SFEINDLDFD LRSLLHYLRS RQLEQGIEPG DSGIAFKNLT   120

AVGVDASAAY GPSVEEMFRN IASIPAHLIS KFTKKSDVPL RNIIQNCTGV VESGEMLFVV   180

GRPGAGCSTF LKCLSGETSE LVDVQGEFSY DGLDQSEMMS KYKGYVIYCP ELDFHFPKIT   240

VKETIDFALK CKTPRVRIDK MTRKQYVDNI RDMWCTVFGL RHTYATKVGN DFVRGVSGGE   300

RKRVSLVEAQ AMNASIYSWD NATRGLDAST ALEFAQAIRT ATNMVNNSAI VAIYQAGENI   360

YELFDKTTVL YNGRQIYFGP ADKAVGYFQR MGWVKPNRMT SAEFLTSVTV DFENRTLDIK   420

PGYEDKVPKS SSEFEEYWLN SEDYQELLRT YDDYQSRHPV NETRDRLDVA KKQRLQQGQR   480

ENSQYVVNYW TQVYYCMIRG FQRVKGDSTY TKVYLSSFLI KALIIGSMFH KIDDKSQSTT   540

AGAYSRGGML FYVLLFASVT SLAEIGNSFS SRPVIVKHKS YSMYHLSAES LQEIITEFPT   600

KFVAIVILCL ITYWIPFMKY EAGAFFQYIL YLLTVQQCTS FIFKFVATMS KSGVDAHAVG   660

GLWVLMLCVY AGFVLPIGEM HHWIRWLHFI NPLTYAFESL VSTEFHHREM LCSALVPSGP   720

GYEGISIANQ VCDAAGAVKG NLYVSGDSYI LHQYHFAYKH AWRNWGVNIV WTFGYIVFNV   780

ILSEYLKPVE GGGDLLLYKR GHMPELGTEN ADARTASREE MMEALNGPNV DLEKVIAEKD   840

VFTWNHLDYT IPYDGATRKL LSDVFGYVKP GKMTALMGES GAGKTTLLNV LAQRINMGVI   900

TGDMLVNAKP LPASFNRSCG YVAQADNHMA ELSVRESLRF AAELRQQSSV PLEEKYEYVE   960

KIITLLGMQN YAEALVGKTG RGLNVEQRKK LSIGVELVAK PSLLLFLDEP TSGLDSQSAW  1020

SIVQFMRALA DSGQSILCTI HQPSATLFEQ FDRLLLLKKG GKMVYFGDIG PNSETLLKYF  1080

ERQSGMKCGV SENPAEYILN CIGAGATASV NSDWHDLWLA SPECAAARAE VEELHRTLPG  1140

RAVNDDPELA TRFAASYMTQ IKCVLRRTAL QFWRSPVYIR AKFFECVACA LFVGLSYVGV  1200

NHSVGGAIEA FSSIFMLLLI ALAMINQLHV FAYDSRELYE VREAASNTFH WSVLLLCHAA  1260

VENFWSTLCQ FMCFICYYWP AQFSGRASHA GFFFFFYVLI FPLYFVTYGL WILYMSPDVP  1320

SASMINSNLF AAMLLFCGIL QPREKMPAFW RRLMYNVSPF TYVVQALVTP LVHNKKVVCN  1380

PHEYNIMDPP SGKTCGEFLS TYMDNNTGYL VNPTATENCQ YCPYTVQDQV VAKYNVKWDH  1440

RWRNFGFMWA YICFNIAAML ICYYVVRVKV WSLKSVLNFK KWFNGPRKER HEKDTNIFQT  1500

VPGDENKITK K                                                      1511

Saccharomyces cerevisiae
                                                        SEQ ID NO: 8
MDTQIAITGV AVGKEINNDN SKTDQKVSLP KADVPCIDKA TQTIIEGCSK DDPRLSYPTK    60

LETTEKGKTK RNSFACVCCH SLKQKCEPSD VNDIYRKPCR RCLKHKKLCK FDLSKRTRKR   120

KPRSRSPTPF ESPMVNVSTK SKGPTDSEES SLKDGTSYLA SFPSDPNAKQ FPNSRTVLPG   180
```

```
LQQSLSDLWS TLSQPPSYGA REAETTSTGE ITTNNHTKSN GSVPTNPAVL ASNDEHTNIS    240

DAPVIYSTYN SPVPISSAPT SINSEALFKH RPKIVGDEET QNVKVKRQKK SYSRHMTRSF    300

RKQLQSLIIS QKGKIRDISM KLDTWSKQWN DLVEKSMFLP TIADPVSVGI ISHEEATLRL    360

HLYKTEISYL SKLPFIKVEE NVSVDELRKK KPILFSVIMS CVSIVLTPKQ TTRGTIMKLD    420

SFVLNLITNQ IFKANNKSIE IIESLSTLCL WYNFFEWSSK TRYHIFNYIC CCLTRDLGPT    480

YVNRSFGMFS DEDPKRFKSP LELYSNGASL TLLVYISALN ISIFLRQSIQ ARWSHVTEKA    540

CEDLVKETKK SRHYDNDKLL LDSADDPILV QFAKMNHVLE NIHTHLHERD LNDDEFDDPI    600

FTKKYLNKLM EKYHKQLQEI FTKLDRNRPR VIAFYYSVEA YLYQYKLAVF IGEMSHTINE    660

KVELPREIMD DFVKCYHCCK SALEEFSKLE PILITSLPLF HTSRIIYTVG MLLLKLRYSV    720

VAIPSFHDLM PLTDDAIALV IGVNNLLEKT SELYPFNNSL YKFRYVIALF CQTYANKVID    780

VADRYNAERE KLKEKQVIDE VSNGHDGTKP INAYVTESQK MPTEEDPIID NNTNQNITAV    840

PDEMLPVYSR VRDDTAAMNL NINSTSYMNE SPHEHRESMT GTTLLPPPFI SNDVTNSADS    900

TNIKPSPSSS VDNLNDYLTD INSLAWGVNS LNDEFWTDLF MNDI                    944
```

*Schizosaccharomyces pombe*

SEQ ID NO: 9
```
MGELKEILKQ RYHELLDWNV KAPHVPLSQR LKHFTWSWFA CTMATGGVGL IIGSFPFRFY     60

GLNTIGKIVY ILQIFLFSLF GSCMLFRFIK YPSTIKDSWN HHLEKLFIAT CLLSISTFID    120

MLAIYAYPDT GEWMVWVIRI LYYIYVAVSF IYCVMAFFTI FNNHVYTIET ASPAWILPIF    180

PPMICGVIAG AVNSTQPAHQ LKNMVIFGIL FQGLGFWVYL LLFAVNVLRF FTVGLAKPQD    240

RPGMFMFVGP PAFSGLALIN IARGAMGSRP YIFVGANSSE YLGFVSTFMA IFIWGLAAWC    300

YCLAMVSFLA GFFTRAPLKF ACGWFAFIFP NVGFVNCTIE IGKMIDSKAF QMFGHIIGVI    360

LCIQWILLMY LMVRAFLVND LCYPGKDEDA HPPPKPNTGV LNPTFPPEKA PASLEKVDTH    420

VTSTGGESDP PSSEHESV                                                 438
```

*Kluyveromyces marxianus*

SEQ ID NO: 10
```
MSNSSSSEGK TNEDGRNSVH SSDSFAQSVA SFHLDDNESQ NVTAQLSQQI TNVLSNSNGA     60

ERIESLARVI STKTKKQMES FEVNQLDFDL KALLNYLRSS QLEQGIEPGD SGIAFHDLTA    120

VGIDASAAFG PSVEEMVRSW IHFPVRLWKK ICRQKSETPL RNIIQHCTGV VESGEMLFVV    180

GRPGAGCSTL LKCLSGETGE LVEVTGDISY DGLSQEEMMQ KFKGYVIYCP ELDFHFPKIT    240

VKETIDFALK CKTPRSRIDH LTRAQYVDNM RDLWCTVFGL THTYATNVGN DVVRGVSGGE    300

RKRVSLVEAL AMNASIYSWD NATRGLDAST ALEFAQAIRT ATNMMNNSAI VAIYQAGENI    360

YQLFDKTTVL YNGKQVYFGP ADEAVGYFER MGYIKPNRMT SAEFLTSATV DFENRTLEVR    420

EGYEEKIPKS STEMEAYWHN SPEYAKATEL FNEYCQSHPE EETRQRLETA KKQRLQKGQR    480

EKSQFVVTFW AQVWYCMIRG FQRVKGDSTY TKVYLSSFLT KGLIVGSMFH KIDPKSQSTT    540

EGAYSRGGLL FYVLLFAALT SLAEISNSFQ NRAIIVKQKT YSMYHTSAES LQEIFTEIPT    600

KFVAILTLSL VSYWIPVLKY DAGSFFQYLL YLFTTQQCTS FIFKLVATLT KDGGTAHAIG    660

GLWVLMLTVY AGFVLPIGNM HHWIRWFHYL NPLTYAYESL MSTEFHGRKM LCSRLLPSGP    720

GYENVSIAHK ICDAAGAVAG QLYVSGDAYV LKKYHFRYKH AWRDWGINIV WTFGYIVMNV    780

VMSEYLKPLE GGGDLLLYKR GHMPELGSES VDSKVASREE MMESLNGPGV DLEKVIASKD    840

VFTWNHLNYT IPYDGATRQL LSDVFGYVKP GKMTALMGES GAGKTTLLNV LAQRINVGVI    900

TGDMLVNAKP LPPSFNRSCG YVAQADNHMG ELSVRESLRF AAELRQPKSV PLQEKYDYVE    960

KIISLLGMEK YAEAIIGKTG RGLNVEQRKK LSIGVELVAK PSLLLFLDEP TSGLDSQSAW   1020

SIVQFMRALA DSGQSILCTI HQPSATLFEQ FDRLLLLKKG GKMVYFGDIG ENSSTLLNYF   1080
```

```
ERQSGVKCGK SENPAEYMLN CIGAGATASA DADWHDLWLQ SPECAAAREE VEELHRTLAS    1140

RPVTDDKELA GRYAASYLTQ MKCVFRRTNI QFWRSPVYIR AKFLECVLCA LFVGLSYVGV    1200

DHSIAGASQS FSSIFMMLLI ALAMVNQLHV FALDSRELYE VREAASNTFH WSVLLLNHTF    1260

VEIIWSTLCE FICWICYYWP AQYSGRASHA GYFFLIYVIM FPAYFVSYGC WVFYMSPDVP    1320

SASMINSNLF AGMLLFCGIL QPKDKMPGFW KRFMYNVSPF TYVVQSLVTP LVQGKKVRCT    1380

KNEFAVVNPP EGQTCSQYFA RFIKDNTGYL KNPNDTESCH YCPYSYQQEV VEQYNVRWVY    1440

RWRNFGFLWA YIGFNFFAML ACYWVLRVKN YSITSIFGVF KIGNWKKAIH HDSRHEKDHT    1500

IFQEKPGDAA NVQKTKA                                                  1517

Pichia kudriavzevii
                                                        SEQ ID NO: 11
MTDKISLGTY LFEKLKEAGS YSIFGVPGDF NLALLDHVKE VEGIRWVGNA NELNAGYEAD     60

GYARINGFAS LITTFGVGEL SAVNAIAGSY AEHVPLIHIV GMPSLSAMKN NLLLHHTLGD    120

TRFDNFTEMS KKISAKVEIV YDLESAPKLI NNLIETAYHT KRPVYLGLPS NFADELVPAA    180

LVKENKLHLE EPLNNPVAEE EFIHNVVEMV KKAEKPIILV DACAARHNIS KEVRELAKLT    240

KFPVFTTPMG KSTVDEDDEE FFGLYLGSLS APDVKDIVGP TDCILSLGGL PSDFNTGSFS    300

YGYTTKNVVE FHSNYCKFKS ATYENLMMKG AVQRLISELK NIKYSNVSTL SPPKSKFAYE    360

SAKVAPEGII TQDYLWKRLS YFLKPRDIIV TETGTSSFGV LATHLPRDSK SISQVLWGSI    420

GFSLPAAVGA AFAAEDAHKQ TGEQERRTVL FIGDGSLQLT VQSISDAARW NIKPYIFILN    480

NRGYTIEKLI HGRHEDYNQI QPWDHQLLLK LFADKTQYEN HVVKSAKDLD ALMKDEAFNK    540

EDKIRVIELF LDEFDAPEIL VAQAKLSDEI NSKAA                              575

Pichia kudriavzevii
                                                        SEQ ID NO: 12
MLQTANSEVP NASQITIDAA SGLPADRVLP NITNTEITIS EYIFYRILQL GVRSVFGVPG     60

DFNLRFLEHI YDVHGLNWIG CCNELNAAYA ADAYAKASKK MGVLLTTYGV GELSALNGVA    120

GAYTEFAPVL HLVGTSALKF KRNPRTLNLH HLAGDKKTFK KSDHYKYERI ASEFSVDSAS    180

IEDDPIEACE MIDRVIYSTW RESRPGYIFL PCDLSEMKVD AQRLASPIEL TYRFNSPVSR    240

VEGVADQILQ LIYQNKNVSI IVDGFIRKFR MESEFYDIME KFGDKVNIFS TMYGKGLIGE    300

EHPRFVGTYF GKYEKAVGNL LEASDLIIHF GNFDHELNMG GFTFNIPQEK YIDLSAQYVD    360

ITGNLDESIT MMEVLPVLAS KLDSSRVNVA DKFEKFDKYY ETPDYQREAS LQETDIMQSL    420

NENLTGDDIL IVETCSFLFA VPDLKVKQHT NIILQAYWAS IGYALPATLG ASLAIRDFNL    480

SGKVYTIEGD GSAQMSLQEL SSMLRYNIDA TMILLNNSGY TIERVIVGPH SSYNDINTNW    540

QWTDLLRAFG DVANEKSVSY TIKEREQLLN ILSDPSFKHN GKFRLLECVL PMFDVPKKLG    600

QFTGKIPA                                                            608

Pichia kudriavzevii
                                                        SEQ ID NO: 13
MAPVSLETCT LEFSCKLPLS EYIFRRIASL GIHNIFGVPG DYNLSFLEHL YSVPELSWVG     60

CCNELNSAYA TDGYSRTIGH DKFGVLLTTQ GVGELSAANA IAGSFAEHVP ILHIVGTTPY    120

SLKHKGSHHH HLINGVSTRE PTNHYAYEEM SKNISCKILS LSDDLTNAAN EIDDLFRTIL    180

MLKKPGYLYI PCDLVNVEID ASNLQSVPAN KLRERVPSTD SQTIAKITST IVDKLLSSSN    240

PVVLCDILTD RYGMTAYAQD LVDSLKVPCC NSFMGKALLN ESKEHYIGDF NGEESNKMVH    300

SYISNTDCFL HIGDYYNEIN SGHWSLYNGI NKESIVILNP EYVKIGSQTY QNVSFEDILP    360

AILSSIKANP NLPCFHIPKI MSTIEQIPSN TPISQTLMLE KLQSFLKPND VLVTETCSLM    420

FGLPDIRMPE NSKVIGQHFY LSIGMALPCS FGVSVALNEL KKDSRLILIE GDGSAQMTVQ    480
```

```
ELSNFNRENV VKPLIILLNN SGYTVERVIK GPKREYNDIR PDWKWTQLLQ TFGMDDAKSM    540

KVTTPEELDD ALDEYGNNLS TPRLLEVVLD KLDVPWRFNK MVGN                   584
```

*Pichia kudriavzevii*

SEQ ID NO: 14
```
MLRLFSRRTP SVRALPKFTR SLATASPEAG AQEVSNLHDI VEIELPEYSF EGYKLDVPEL    60

NYSTEKGTLL QMYKDMVIIR RMEMAADALY KAKKIRGFCH LSVGQEAIAV GIENAITKQD   120

DIITSYRCHG TTYMRGASVQ EVLAELMGRR SGVSYGKGGS MHMYTKGFYG GNGIVGAQVP   180

LGTGLAFAHH YRDQKNMTWT MYGDGAANQG QVFESFNMAK LWNLPCVFTC ENNKYGMGTS   240

ASRSSAMTEY YKRGQYIPGL KVNGMDILAV YQAAKFAKEW TSNDNGPLVI EFETYRYGGH   300

SMSDPGTTYR TREEVQNMRS KKDPIAGLKA HLLEFNIATE EEIKAFDKSA RKYVDEQVKL   360

ADASPPPEAK MSILFEDVYV PGSEIPVLRG RIRDDSWSFE KGGFAYK                407
```

*Pichia kudriavzevii*

SEQ ID NO: 15
```
MVSPAERLST IASTIKPNRK DSTSLQPEDY PEHPFKVTVV GSGNWGCTIA KVIAENTVER    60

PRQFQRDVNM WVYEELIEGE KLTEIINTKH ENVKYLPGIK LPVNVVAVPD IVEACAGSDL   120

IVFNIPHQFL PRILSQLKGK VNPKARAISC LKGLDVNPNG CKLLSTVITE ELGIYCGALS   180

GANLAPEVAQ CKWSETTVAY TIPDDFRGKG KDIDHQILKS LFHRPYFHVR VISDVAGISI   240

AGALKNVVAM AAGFVEGLGW GDNAKAAVMR IGLVETIQFA KTFFDGCHAA TFTHESAGVA   300

DLITTCAGGR NVRVGRYMAQ HSVSATEAEE KLLNGQSCQG IHTTREVYEF LSNMGRTDEF   360

PLFTTTYRII YENFPIEKLP ECLEPVED                                     388
```

*Pichia kudriavzevii*

SEQ ID NO: 16
```
MIPRLNPLLN ISHLRGGPKF IGKAIKPSQF EFRKNNFRFN STSTKTGSAR TIKSGFLSWS    60

FRAATFTGIA GWLYLTYLVY KETNPGSQSP QTEFSEIGNK KKNIVILGSG WGAVSVLKTL   120

DTTKYNVTIV SPRNYFLFTP LLPSVPSGTI DIKSICDSIR TIARQTPGEV TYLEAAATDI   180

DPVKKTIKLE HKSQRFLIGD AFTSEGDVIE NELSYDYLVY AVGATVNTFG IPGIPEYASY   240

LKEANDATAV RQKLFNQIEA SRLLPKDSED RKRLLSFVVC GGGPTGVELA AEIKDYIDQD   300

LCKFIPGIEK EMQVTLIEAQ HNVLSMFHPK LIEYTKEVFK QQNLHLQVDT MVKKVDDKNV   360

YATYRHPDGK TEDMVIPYGT LVWAGGNAQR KLTRDLSSKI IEQKTARRGL LVDEYLKLDG   420

DDSIYAIGDC TFTPNPPTAQ VAHQQGEYLG EHFNKLAKID ELNYLITNST DDSTKYSKRL   480

ERAEKAIKPF EYDHQGALAY VGSERAVADL HWGSWSTVAL GGTMTFFFWR TAYVSMLLSI   540

RNKILVVTDW VKVAIFGRDC SQE                                          563
```

*Leuconostoc mesenteroides*

SEQ ID NO: 17
```
MKIFAYGIRD DEKPSLEEWK AANPEIEVDY TQELLTPETV KLAEGSDSAV VYQQLDYTRE    60

TLTALANVGV TNLSLRNVGT DNIDFDAARE FNFNISNVPV YSPNAIAEHS MIQLSRLLRR   120

TKALDAKIAK HDLRWAPTIG REMRMQTVGV IGTGHIGRVA INILKGFGAK VIAYDKYPNA   180

ELQAEGLYVD TLDELYAQAD AISLYVPGVP ENHHLINAEA IAKMKDGVVI MNAARGNLMD   240

IDAIIDGLNS GKISDFGMDV YENEVGLFNE DWSGKEFPDA KIADLISREN VLVTPHTAFY   300

TTKAVLEMVH QSFDAAVAFA KGEKPAIAVE Y                                 331
```

*Lactobacillus plantarum*

SEQ ID NO: 18
```
MKIIAYAVRD DERPFFDTWM KENPDVEVKL VPELLTEDNV DLAKGFDGAD VYQQKDYTAE    60

VLNKLADEGV KNISLRNVGV DNLDVPTVKA RGLNISNVPA YSPNAIAELS VTQLMQLLRQ   120

TPLFNKKLAK QDFRWAPDIA KELNTMTVGV IGTGRIGRAA IDIFKGFGAK VIGYDVYRNA   180

ELEKEGMYVD TLDELYAQAD VITLHVPALK DNYHMLNADA FSKMKDGAYI LNFARGTLID   240
```

```
SEDLIKALDS GKVAGAALDT YEYETKIFNK DLEGQTIDDK VFMNLFNRDN VLITPHTAFY      300

TETAVHNMVH VSMNSNKQFI ETGKADTQVK FD                                   332

Pseudomonas aeruginosa
                                                         SEQ ID NO: 19
MRILFFSSQA YDSESFQASN HRHGFELHFQ QAHLQADTAV LAQGFEVVCA FVNDDLSRPV       60

LERLAAGGTR LVALRSAGYN HVDLAAAEAL GLPVVHVPAY SPHAVAEHAV GLILTLNRRL      120

HRAYNRTREG DFSLHGLTGF DLHGKRVGVI GTGQIGETFA RIMAGFGCEL LAYDPYPNPR      180

IQALGGRYLA LDALLAESDI VSLHCPLTAD TRHLIDAQRL ATMKPGAMLI NTGRGALVNA      240

AALIEALKSG QLGYLGLDVY EEEADIFFED RSDQPLQDDV LARLLSFPNV VVTAHQAFLT      300

REALAAIADT TLDNIAAWQD GTPRNRVRA                                       329

Fusobacterium nucleatum
                                                         SEQ ID NO: 20
MQKTKIIFFD IKDYDKEFFK KYGADYNFEM TFLKVRLTEE TANLTKGYDV VCGFANDNIN       60

KETIDIMAEN GIKLLAMRCA GFNNVSLKDV NERFKVVRVP AYSPHAIAEY TVGLILAVNR      120

KINKAYVRTR EGNFSINGLM GIDLYEKTAG IIGTGKIGQI LIKILRGFDM KVIAYDLFPN      180

QKVADELGFE YVSLDELYAN SDIISLNCPL TKDTKYMINR RSMLKMKDGV ILVNTGRGML      240

IDSADLVEAL KDKKIGAVAL DVYEEEENYF FEDKSTQVIE DDILGRLLSF YNVLITSHQA      300

YFTKEAVGAI TVTTLNNIKD FVEGRPLVNE VPQNQ                                335

Pediococcus acidilactici
                                                         SEQ ID NO: 21
MKIIAYGIRD DEKPYLDEWV TKNHIEVKAV PDLLDSSNID LAKDYDGVVA YQQKPYTADL       60

FDKMHEFGIH AFSLRNVGVD NVPADALKKN DIKISNVPAY SPRAIAELSV TQLLALLRKI      120

PEFEYKMAHG DYRWEPDIGL ELNQMTVGVI GTGRIGRAAI DIFKGFGAKV IAYDVFRNPA      180

LEKEGMYVDT LEELYQQANV ITLHVPALKD NYHMLDEKAF GQMQDGTFIL NFARGTLIDT      240

PALLKALDSG KVAGAALDTY ENEVGIFDVD HGDQPIDDPV FNDLMSRRNV MITPHAAFYT      300

RPAVKNMVQI ALDNNRDLIE KNSSKNEVKF D                                    331

Lactobacillus plantarum
                                                         SEQ ID NO: 22
MKIIAYAVRD DERPFFDTWM KENPDVEVKL VPELLTEDNV DLAKGFDGAD VYQQKDYTAE       60

VLNKLADEGV KNISLRNVGV DNLDVPTVKA RGLNISNVPA YSPNAIAELS VTQLMQLLRQ      120

TPMFNKKLAK QDFRWAPNIA KELNTMTVGV IGTGRIGRAA IDIFKGFGAK VIGYDVYRNA      180

ELEKEGMYVD TLDELYAQAD VITLHVPALK DNYHMLNADA FSKMKDGAYI LNFARGTLID      240

SEDLIKALDS GKVAGAALDT YEYETKIFNK DLEGQTIDDK VFMNLFNRDN VLITPHTAFY      300

TETAVHNMVH VSMNSNKQFI ETGKADTQVK FD                                   332

Leuconostoc carnosum
                                                         SEQ ID NO: 23
MKIFAYGIRD DEKPSLEDWK STHPEVEVDY TQELLTPETA KLASGSDSAV VYQQLDYTRE       60

TLTALSEVGV TNLSLRNVGT DNIDFEAAKE LNFNISNVPV YSPNAIAEHS MIQLSRLLRR      120

TKALDAKIAK HDLRWAPTIG REVRMQTVGV IGTGNIGRVA IKILQGFGAK VVAYDKFPNA      180

EIAAQGLYVD SLDELYAQAD AVALFVPGVP ENHHMIDASA IAKMKDGVII MNASRGNLMA      240

IDDIIDGLNS GKISDFGMDV YEEEVGLFNE DWSNKEFPDS KIADLISREN VLVTPHTAFY      300

TTKAVLEMVH QSMDAAVAFA NGETPSIAVK Y                                    331
```

What is claimed is:

1. A recombinant cell, comprising:
a heterologous nucleic acid encoding a D-lactate dehydrogenase selected from SEQ ID NO: 1, SEQ ID NO: 2, SEQ ID NO: 3, SEQ ID NO: 4, SEQ ID NO: 5, SEQ ID NO: 6, SEQ ID NO: 17, SEQ ID NO: 18, SEQ ID NO: 19, SEQ ID NO: 20, SEQ ID NO: 21, SEQ ID NO: 22 or SEQ ID NO: 23, wherein:
the D-lactate dehydrogenase nucleic acid comprises the residues GXGXXG, wherein X refers to any amino acid;
a negatively charged amino acid located 18-20 residues downstream from the GXGXXG sequence is mutated to a neutral amino acid; and
wherein the heterologous nucleic acid is expressed in sufficient amount to produce D-lactic acid.

2. The recombinant cell of claim 1, wherein the recombinant cell is a yeast cell.

3. The recombinant cell of claim 2, wherein the yeast cell is *Pichia kudriavzevii* or *Saccharomyces cerevisiae*.

4. The recombinant cell of claim 1, wherein the recombinant cell is a prokaryotic cell.

5. The recombinant cell of claim 4, wherein the prokaryotic cell is *Escherichia coli, Corynebacterium glutamicum, Bacillus subtilis*, or *Lactococcus lactis*.

6. The recombinant cell of claim 1, further comprising one or more additional heterologous nucleic acids encoding one or more proteins selected from organic acid transporters and redox cofactor biogenesis proteins.

7. The recombinant cell of claim 6, wherein one of the additional heterologous nucleic acids encodes an organic acid transporter having at least 90% amino acid identity with a sequence selected from SEQ ID NO: 7, SEQ ID NO: 8, SEQ ID NO: 9, and SEQ ID NO: 10.

8. The recombinant cell of claim 7, further comprising a genetic disruption of one or more genes encoding pyruvate decarboxylase, a protein subunit of the pyruvate dehydrogenase complex, glycerol-3-phosphate dehydrogenase, NAD(P)H dehydrogenase, or combinations thereof.

9. The recombinant cell of claim 8, wherein the genetic disruption is in a pyruvate decarboxylase gene having at least 90% amino acid identity with a sequence selected from SEQ ID NO: 11, SEQ ID NO: 12, SEQ ID NO: 13, and SEQ ID NO: 14.

10. The recombinant cell of claim 9, wherein the genetic disruption is in a glycerol-3-phosphate dehydrogenase gene having at least 90% amino acid identity with SEQ ID NO: 15.

11. The recombinant cell of claim 9, wherein the genetic disruption is in an NAD(P)H dehydrogenase gene having at least 90% amino acid identity with SEQ ID NO: 16.

12. A recombinant *Pichia kudriavzevii* cell, comprising a heterologous nucleic acid encoding D-lactate dehydrogenase selected from SEQ ID NO: 3, SEQ ID NO: 4, SEQ ID NO: 5, SEQ ID NO: 6, SEQ ID NO: 18, SEQ ID NO: 19, SEQ ID NO: 20, SEQ ID NO: 21, SEQ ID NO: 22, and SEQ ID NO: 23, wherein:
the D-lactate dehydrogenase nucleic acid comprises the residues GXGXXG, wherein X refers to any amino acid; and
a negatively charged amino acid located 18-20 residues downstream from the GXGXXG sequence is mutated to a neutral amino acid.

13. The recombinant cell of claim 12, further comprising a heterologous nucleic acid encoding an organic acid transporter protein selected from SEQ ID NO: 7, SEQ ID NO: 8, SEQ ID NO: 9, and SEQ ID NO: 10.

14. The recombinant cell of claim 12, further comprising a genetic disruption of:
a pyruvate decarboxylase having at least 90% amino acid identity with SEQ ID NO: 11, SEQ ID NO: 12, SEQ ID NO: 13, or SEQ ID NO: 14;
a glycerol-3-phosphate dehydrogenase gene having at least 90% amino acid identity with SEQ ID NO: 15;
an NAD(P)H dehydrogenase gene having at least 90% amino acid identity with SEQ ID NO: 16; and combinations thereof.

15. A method for producing D-lactic acid comprising:
culturing the recombinant cell of claim 1 under fermentation conditions suitable to produce D-lactic acid, or a salt thereof.

* * * * *

SEQUENCE LISTING

<160> NUMBER OF SEQ ID NOS: 23

<210> SEQ ID NO 1
<211> LENGTH: 331
<212> TYPE: PRT
<213> ORGANISM: Leuconostoc mesenteroides

<400> SEQUENCE: 1

```
Met Lys Ile Phe Ala Tyr Gly Ile Arg Asp Asp Glu Lys Pro Ser Leu
1               5                   10                  15

Glu Glu Trp Lys Ala Ala Asn Pro Glu Ile Glu Val Asp Tyr Thr Gln
            20                  25                  30

Glu Leu Leu Thr Pro Glu Thr Ala Lys Leu Ala Glu Gly Ser Asp Ser
        35                  40                  45

Ala Val Val Tyr Gln Gln Leu Asp Tyr Thr Arg Glu Thr Leu Thr Ala
    50                  55                  60

Leu Ala Asn Val Gly Val Thr Asn Leu Ser Leu Arg Asn Val Gly Thr
65                  70                  75                  80

Asp Asn Ile Asp Phe Asp Ala Ala Arg Glu Phe Asn Phe Asn Ile Ser
                85                  90                  95

Asn Val Pro Val Tyr Ser Pro Asn Ala Ile Ala Glu His Ser Met Leu
            100                 105                 110

Gln Leu Ser Arg Leu Leu Arg Arg Thr Lys Ala Leu Asp Ala Lys Ile
        115                 120                 125

Ala Lys Arg Asp Leu Arg Trp Ala Pro Thr Thr Gly Arg Glu Met Arg
    130                 135                 140

Met Gln Thr Val Gly Val Ile Gly Thr Gly His Ile Gly Arg Val Ala
145                 150                 155                 160

Ile Asn Ile Leu Lys Gly Phe Gly Ala Lys Val Ile Ala Tyr Asp Lys
                165                 170                 175

Tyr Pro Asn Ala Glu Leu Gln Ala Glu Gly Leu Tyr Val Asp Thr Leu
            180                 185                 190

Asp Glu Leu Tyr Ala Gln Ala Asp Ala Ile Ser Leu Tyr Val Pro Gly
        195                 200                 205

Val Pro Glu Asn His His Leu Ile Asn Ala Asp Ala Ile Ala Lys Met
    210                 215                 220

Lys Asp Gly Val Val Ile Met Asn Ala Ala Arg Gly Asn Leu Met Asp
225                 230                 235                 240

Ile Asp Ala Ile Ile Asp Gly Leu Asn Ser Gly Lys Ile Ser Asp Phe
                245                 250                 255

Gly Met Asp Val Tyr Glu Asn Glu Val Ala Cys Ser Met Lys Ile Gly
            260                 265                 270

Leu Val Lys Asn Ser Pro Asp Ala Lys Ile Ala Asp Leu Ile Ala Arg
        275                 280                 285

Glu Asn Val Met Ile Thr Pro His Thr Ala Phe Tyr Thr Thr Lys Ala
    290                 295                 300

Val Leu Glu Met Val His Gln Ser Phe Asp Ala Ala Val Ala Phe Ala
305                 310                 315                 320

Lys Gly Glu Lys Pro Ala Ile Ala Val Glu Tyr
                325                 330
```

<210> SEQ ID NO 2
<211> LENGTH: 331
<212> TYPE: PRT
<213> ORGANISM: Leuconostoc mesenteroides

<400> SEQUENCE: 2

| | | | | | | | | | | | | | | |
|---|---|---|---|---|---|---|---|---|---|---|---|---|---|---|
|Met|Lys|Ile|Phe|Ala|Tyr|Gly|Ile|Arg|Asp|Asp|Glu|Lys|Pro|Ser|Leu|
|1| | | |5| | | | |10| | | | |15| |

Glu Glu Trp Lys Ala Ala Asn Pro Glu Ile Glu Val Asp Tyr Thr Gln
            20                  25                  30

Glu Leu Leu Thr Pro Glu Thr Ala Lys Leu Ala Glu Gly Ser Asp Ser
        35                  40                  45

Ala Val Val Tyr Gln Gln Leu Asp Tyr Thr Arg Glu Thr Leu Thr Ala
    50                  55                  60

Leu Ala Asn Val Gly Val Thr Asn Leu Ser Leu Arg Asn Val Gly Thr
65                  70                  75                  80

Asp Asn Ile Asp Phe Asp Ala Ala Arg Glu Phe Asn Phe Asn Ile Ser
                85                  90                  95

Asn Val Pro Val Tyr Ser Pro Asn Ala Ile Ala Glu His Ser Met Ile
            100                 105                 110

Gln Leu Ser Arg Leu Leu Arg Arg Thr Lys Ala Leu Asp Ala Lys Ile
        115                 120                 125

Ala Lys His Asp Leu Arg Trp Ala Pro Thr Ile Gly Arg Glu Met Arg
130                 135                 140

Met Gln Thr Val Gly Val Ile Gly Thr Gly His Ile Gly Arg Val Ala
145                 150                 155                 160

Ile Asn Ile Leu Lys Gly Phe Gly Ala Lys Val Ile Ala Tyr Asp Lys
                165                 170                 175

Tyr Pro Asn Ala Glu Leu Gln Ala Glu Gly Leu Tyr Val Asp Thr Leu
            180                 185                 190

Asp Glu Leu Tyr Ala Gln Ala Asp Ala Ile Ser Leu Tyr Val Pro Gly
        195                 200                 205

Val Pro Glu Asn His His Leu Ile Asn Ala Asp Ala Ile Ala Lys Met
210                 215                 220

Lys Asp Gly Val Val Ile Met Asn Ala Ala Arg Gly Asn Leu Met Asp
225                 230                 235                 240

Ile Asp Ala Ile Ile Asp Gly Leu Asn Ser Gly Lys Ile Ser Asp Phe
                245                 250                 255

Gly Met Asp Val Tyr Glu Asn Glu Val Gly Leu Phe Asn Glu Asp Trp
            260                 265                 270

Ser Gly Lys Glu Phe Pro Asp Ala Lys Ile Ala Asp Leu Ile Ala Arg
        275                 280                 285

Glu Asn Val Leu Val Thr Pro His Thr Ala Phe Tyr Thr Thr Lys Ala
290                 295                 300

Val Leu Glu Met Val His Gln Ser Phe Asp Ala Val Ala Phe Ala
305                 310                 315                 320

Lys Gly Glu Lys Pro Ala Ile Ala Val Glu Tyr
            325                 330

<210> SEQ ID NO 3
<211> LENGTH: 333
<212> TYPE: PRT
<213> ORGANISM: Lactobacillus delbrueckii

<400> SEQUENCE: 3

Met Thr Lys Ile Phe Ala Tyr Ala Ile Arg Glu Asp Glu Lys Pro Phe
1               5                   10                  15

Leu Lys Glu Trp Glu Asp Ala His Lys Asp Val Glu Val Glu Tyr Thr
            20                  25                  30

-continued

Asp Lys Leu Leu Thr Pro Glu Thr Ala Leu Ala Lys Gly Ala Asp
            35                  40                  45

Gly Val Val Val Tyr Gln Gln Leu Asp Tyr Thr Ala Glu Thr Leu Gln
 50                  55                  60

Ala Leu Ala Asp Asn Gly Ile Thr Lys Met Ser Leu Arg Asn Val Gly
 65                  70                  75                  80

Val Asp Asn Ile Asp Met Ala Lys Ala Lys Glu Leu Gly Phe Gln Ile
                85                  90                  95

Thr Asn Val Pro Val Tyr Ser Pro Asn Ala Ile Ala Glu His Ala Ala
                100                 105                 110

Ile Gln Ala Ala Arg Ile Leu Arg Gln Asp Lys Ala Met Asp Glu Lys
            115                 120                 125

Val Ala Arg His Asp Leu Arg Trp Ala Pro Thr Ile Gly Arg Glu Val
130                 135                 140

Arg Asp Gln Val Val Gly Val Ile Gly Thr Gly His Ile Gly Gln Val
145                 150                 155                 160

Phe Met Gln Ile Met Glu Gly Phe Gly Ala Lys Val Ile Ala Tyr Asp
                165                 170                 175

Ile Phe Arg Asn Pro Glu Leu Glu Lys Lys Gly Tyr Tyr Val Asp Ser
            180                 185                 190

Leu Asp Asp Leu Tyr Lys Gln Ala Asp Val Ile Ser Leu His Val Pro
        195                 200                 205

Asp Val Pro Ala Asn Val His Met Ile Asn Asp Glu Ser Ile Ala Lys
    210                 215                 220

Met Lys Gln Asp Val Val Ile Val Asn Val Ser Arg Gly Pro Leu Val
225                 230                 235                 240

Asp Thr Asp Ala Val Ile Arg Gly Leu Asp Ser Gly Lys Ile Phe Gly
                245                 250                 255

Tyr Ala Met Asp Val Tyr Glu Gly Glu Val Gly Ile Phe Asn Glu Asp
            260                 265                 270

Trp Glu Gly Lys Glu Phe Pro Asp Ala Arg Leu Ala Asp Leu Ile Ala
        275                 280                 285

Arg Pro Asn Val Leu Val Thr Pro His Thr Ala Phe Tyr Thr Thr His
    290                 295                 300

Ala Val Arg Asn Met Val Val Lys Ala Phe Asp Asn Asn Leu Glu Leu
305                 310                 315                 320

Val Glu Gly Lys Glu Ala Glu Thr Pro Val Lys Val Gly
                325                 330

<210> SEQ ID NO 4
<211> LENGTH: 337
<212> TYPE: PRT
<213> ORGANISM: Lactobacillus helveticus

<400> SEQUENCE: 4

Met Thr Lys Val Phe Ala Tyr Ala Ile Arg Lys Asp Glu Glu Pro Phe
1               5                   10                  15

Leu Asn Glu Trp Lys Glu Ala His Lys Asp Ile Asp Val Asp Tyr Thr
            20                  25                  30

Asp Lys Leu Leu Thr Pro Glu Thr Ala Lys Leu Ala Lys Gly Ala Asp
        35                  40                  45

Gly Val Val Val Tyr Gln Gln Leu Asp Tyr Thr Ala Asp Thr Leu Gln
 50                  55                  60

Ala Leu Ala Asp Ala Gly Val Thr Lys Met Ser Leu Arg Asn Val Gly
65                  70                  75                  80

Val Asp Asn Ile Asp Met Asp Lys Ala Lys Glu Leu Gly Phe Gln Ile
            85                  90                  95

Thr Asn Val Pro Val Tyr Ser Pro Asn Ala Ile Ala Glu His Ala Ala
        100                 105                 110

Ile Gln Ala Ala Arg Val Leu Arg Gln Asp Lys Arg Met Asp Glu Lys
    115                 120                 125

Met Ala Lys Arg Asp Leu Arg Trp Ala Pro Thr Ile Gly Arg Glu Val
130                 135                 140

Arg Asp Gln Val Val Gly Val Gly Thr Gly His Ile Gly Gln Val
145                 150                 155                 160

Phe Met Arg Ile Met Glu Gly Phe Gly Ala Lys Val Ile Ala Tyr Asp
                165                 170                 175

Ile Phe Lys Asn Pro Glu Leu Glu Lys Lys Gly Tyr Tyr Val Asp Ser
            180                 185                 190

Leu Asp Asp Leu Tyr Lys Gln Ala Asp Val Ile Ser Leu His Val Pro
        195                 200                 205

Asp Val Pro Ala Asn Val His Met Ile Asn Asp Lys Ser Ile Ala Glu
    210                 215                 220

Met Lys Asp Gly Val Val Ile Val Asn Cys Ser Arg Gly Arg Leu Val
225                 230                 235                 240

Asp Thr Asp Ala Val Ile Arg Gly Leu Asp Ser Gly Lys Ile Phe Gly
                245                 250                 255

Phe Val Met Asp Thr Tyr Glu Asp Glu Val Gly Val Phe Asn Lys Asp
            260                 265                 270

Trp Glu Gly Lys Glu Phe Pro Asp Lys Arg Leu Ala Asp Leu Ile Asp
        275                 280                 285

Arg Pro Asn Val Leu Val Thr Pro His Thr Ala Phe Tyr Thr Thr His
    290                 295                 300

Ala Val Arg Asn Met Val Val Lys Ala Phe Asn Asn Asn Leu Lys Leu
305                 310                 315                 320

Ile Asn Gly Glu Lys Pro Asp Ser Pro Val Ala Leu Asn Lys Asn Lys
                325                 330                 335

Phe

<210> SEQ ID NO 5
<211> LENGTH: 332
<212> TYPE: PRT
<213> ORGANISM: Lactobacillus pentosus

<400> SEQUENCE: 5

Met Lys Ile Ile Ala Tyr Ala Val Arg Asp Asp Glu Arg Pro Phe Phe
1               5                   10                  15

Asp Thr Trp Met Lys Glu Asn Pro Asp Val Glu Val Lys Leu Val Pro
            20                  25                  30

Glu Leu Leu Thr Glu Asp Asn Val Asp Leu Ala Lys Gly Phe Asp Gly
        35                  40                  45

Ala Asp Val Tyr Gln Gln Lys Asp Tyr Thr Ala Glu Val Leu Asn Lys
    50                  55                  60

Leu Ala Asp Glu Gly Val Lys Asn Ile Ser Leu Arg Asn Val Gly Val
65                  70                  75                  80

Asp Asn Leu Asp Val Pro Thr Val Lys Ala Arg Gly Leu Asn Ile Ser
                85                  90                  95

Asn Val Pro Ala Tyr Ser Pro Asn Ala Ile Ala Glu Leu Ser Val Thr
            100                 105                 110

Gln Leu Met Gln Leu Leu Arg Gln Thr Pro Met Phe Asn Lys Lys Leu
            115                 120                 125

Ala Lys Gln Asp Phe Arg Trp Ala Pro Asp Ile Ala Lys Glu Leu Asn
        130                 135                 140

Thr Met Thr Val Gly Val Ile Gly Thr Gly Arg Ile Gly Arg Ala Ala
145                 150                 155                 160

Ile Asp Ile Phe Lys Gly Phe Gly Ala Lys Val Ile Gly Tyr Asp Val
                165                 170                 175

Tyr Arg Asn Ala Glu Leu Glu Lys Glu Gly Met Tyr Val Asp Thr Leu
            180                 185                 190

Asp Glu Leu Tyr Ala Gln Ala Asp Val Ile Thr Leu His Val Pro Ala
        195                 200                 205

Leu Lys Asp Asn Tyr His Met Leu Asn Ala Asp Ala Phe Ser Lys Met
            210                 215                 220

Lys Asp Gly Ala Tyr Ile Leu Asn Phe Ala Arg Gly Thr Leu Ile Asp
225                 230                 235                 240

Ser Glu Asp Leu Ile Lys Ala Leu Asp Ser Gly Lys Val Ala Gly Ala
                245                 250                 255

Ala Leu Val Thr Tyr Glu Tyr Glu Thr Lys Ile Phe Asn Lys Asp Leu
            260                 265                 270

Glu Gly Gln Thr Ile Asp Asp Lys Val Phe Met Asn Leu Phe Asn Arg
        275                 280                 285

Asp Asn Val Leu Ile Thr Pro His Thr Ala Phe Tyr Thr Glu Thr Ala
        290                 295                 300

Val His Asn Met Val His Val Ser Met Asn Ser Asn Lys Gln Phe Ile
305                 310                 315                 320

Glu Thr Gly Lys Ala Asp Thr Gln Val Lys Phe Asp
                325                 330

<210> SEQ ID NO 6
<211> LENGTH: 331
<212> TYPE: PRT
<213> ORGANISM: Artificial Sequence
<220> FEATURE:
<223> OTHER INFORMATION: Synthetic Sequence

<400> SEQUENCE: 6

Met Lys Ile Phe Ala Tyr Gly Ile Arg Asp Asp Glu Lys Pro Ser Leu
1               5                   10                  15

Glu Glu Trp Lys Ala Ala His Pro Glu Ile Glu Val Asp Tyr Thr Asp
            20                  25                  30

Glu Leu Leu Thr Pro Glu Thr Ala Lys Leu Ala Glu Gly Ala Asp Gly
        35                  40                  45

Val Val Val Tyr Gln Gln Leu Asp Tyr Thr Arg Glu Thr Leu Gln Ala
    50                  55                  60

Leu Ala Asp Ala Gly Val Thr Lys Met Ser Leu Arg Asn Val Gly Thr
65                  70                  75                  80

Asp Asn Ile Asp Phe Asp Ala Ala Lys Glu Phe Gly Phe Asn Ile Ser
                85                  90                  95

Asn Val Pro Val Tyr Ser Pro Asn Ala Ile Ala Glu His Ala Ala Ile
            100                 105                 110

Gln Ala Ser Arg Leu Leu Arg Arg Asp Lys Ala Leu Asp Ala Lys Ile
        115                 120                 125

Ala Lys Arg Asp Leu Arg Trp Ala Pro Thr Ile Gly Arg Glu Val Arg
    130                 135                 140

Met Gln Thr Val Gly Val Gly Thr Gly His Ile Gly Arg Val Ala
145                 150                 155                 160

Met Asn Ile Leu Glu Gly Phe Gly Ala Lys Val Ile Ala Tyr Asp Ile
            165                 170                 175

Phe Lys Asn Ala Glu Leu Glu Lys Glu Gly Leu Tyr Val Asp Ser Leu
            180                 185                 190

Asp Glu Leu Tyr Ala Gln Ala Asp Val Ile Ser Leu His Val Pro Gly
            195                 200                 205

Val Pro Ala Asn His His Met Ile Asn Ala Asp Ser Ile Ala Lys Met
210                 215                 220

Lys Asp Gly Val Val Ile Val Asn Cys Ser Arg Gly Asn Leu Val Asp
225                 230                 235                 240

Thr Asp Ala Val Ile Asp Gly Leu Asp Ser Gly Lys Ile Ser Gly Phe
                245                 250                 255

Val Met Asp Val Tyr Glu Gly Glu Val Gly Leu Phe Asn Glu Asp Trp
            260                 265                 270

Glu Gly Lys Glu Phe Pro Asp Ala Arg Leu Ala Asp Leu Ile Asp Arg
            275                 280                 285

Glu Asn Val Leu Val Thr Pro His Thr Ala Phe Tyr Thr Thr Lys Ala
290                 295                 300

Val Leu Glu Met Val His Gln Ser Phe Asp Ala Ala Leu Ala Phe Ile
305                 310                 315                 320

Asn Gly Glu Lys Pro Ala Ile Ala Val Glu Tyr
                325                 330

<210> SEQ ID NO 7
<211> LENGTH: 1511
<212> TYPE: PRT
<213> ORGANISM: Saccharomyces cerevisiae

<400> SEQUENCE: 7

Met Ser Ser Thr Asp Glu His Ile Glu Lys Asp Ile Ser Ser Arg Ser
1               5                   10                  15

Asn His Asp Asp Asp Tyr Ala Asn Ser Val Gln Ser Tyr Ala Ala Ser
            20                  25                  30

Glu Gly Gln Val Asp Asn Glu Asp Leu Ala Ala Thr Ser Gln Leu Ser
        35                  40                  45

Arg His Leu Ser Asn Ile Leu Ser Asn Glu Glu Gly Ile Glu Arg Leu
    50                  55                  60

Glu Ser Met Ala Arg Val Ile Ser His Lys Thr Lys Lys Glu Met Asp
65                  70                  75                  80

Ser Phe Glu Ile Asn Asp Leu Asp Phe Asp Leu Arg Ser Leu Leu His
                85                  90                  95

Tyr Leu Arg Ser Arg Gln Leu Glu Gln Gly Ile Glu Pro Gly Asp Ser
            100                 105                 110

Gly Ile Ala Phe Lys Asn Leu Thr Ala Val Gly Val Asp Ala Ser Ala
        115                 120                 125

Ala Tyr Gly Pro Ser Val Glu Glu Met Phe Arg Asn Ile Ala Ser Ile
    130                 135                 140

Pro Ala His Leu Ile Ser Lys Phe Thr Lys Ser Asp Val Pro Leu
145                 150                 155                 160

Arg Asn Ile Ile Gln Asn Cys Thr Gly Val Val Glu Ser Gly Glu Met
                165                 170                 175

Leu Phe Val Val Gly Arg Pro Gly Ala Gly Cys Ser Thr Phe Leu Lys

```
                180             185             190
Cys Leu Ser Gly Glu Thr Ser Glu Leu Val Asp Val Gln Gly Glu Phe
    195             200             205

Ser Tyr Asp Gly Leu Asp Gln Ser Glu Met Met Ser Lys Tyr Lys Gly
    210             215             220

Tyr Val Ile Tyr Cys Pro Glu Leu Asp Phe His Phe Pro Lys Ile Thr
225             230             235             240

Val Lys Glu Thr Ile Asp Phe Ala Leu Lys Cys Lys Thr Pro Arg Val
                245             250             255

Arg Ile Asp Lys Met Thr Arg Lys Gln Tyr Val Asp Asn Ile Arg Asp
                260             265             270

Met Trp Cys Thr Val Phe Gly Leu Arg His Thr Tyr Ala Thr Lys Val
        275             280             285

Gly Asn Asp Phe Val Arg Gly Val Ser Gly Glu Arg Lys Arg Val
        290             295             300

Ser Leu Val Glu Ala Gln Ala Met Asn Ala Ser Ile Tyr Ser Trp Asp
305             310             315             320

Asn Ala Thr Arg Gly Leu Asp Ala Ser Thr Ala Leu Glu Phe Ala Gln
                325             330             335

Ala Ile Arg Thr Ala Thr Asn Met Val Asn Asn Ser Ala Ile Val Ala
                340             345             350

Ile Tyr Gln Ala Gly Glu Asn Ile Tyr Glu Leu Phe Asp Lys Thr Thr
                355             360             365

Val Leu Tyr Asn Gly Arg Gln Ile Tyr Phe Gly Pro Ala Asp Lys Ala
    370             375             380

Val Gly Tyr Phe Gln Arg Met Gly Trp Val Lys Pro Asn Arg Met Thr
385             390             395             400

Ser Ala Glu Phe Leu Thr Ser Val Thr Val Asp Phe Glu Asn Arg Thr
                405             410             415

Leu Asp Ile Lys Pro Gly Tyr Glu Asp Lys Val Pro Lys Ser Ser Ser
                420             425             430

Glu Phe Glu Glu Tyr Trp Leu Asn Ser Glu Asp Tyr Gln Glu Leu Leu
    435             440             445

Arg Thr Tyr Asp Asp Tyr Gln Ser Arg His Pro Val Asn Glu Thr Arg
    450             455             460

Asp Arg Leu Asp Val Ala Lys Lys Gln Arg Leu Gln Gln Gly Gln Arg
465             470             475             480

Glu Asn Ser Gln Tyr Val Val Asn Tyr Trp Thr Gln Val Tyr Tyr Cys
                485             490             495

Met Ile Arg Gly Phe Gln Arg Val Lys Gly Asp Ser Thr Tyr Thr Lys
                500             505             510

Val Tyr Leu Ser Ser Phe Leu Ile Lys Ala Leu Ile Ile Gly Ser Met
    515             520             525

Phe His Lys Ile Asp Asp Lys Ser Gln Ser Thr Thr Ala Gly Ala Tyr
    530             535             540

Ser Arg Gly Gly Met Leu Phe Tyr Val Leu Leu Phe Ala Ser Val Thr
545             550             555             560

Ser Leu Ala Glu Ile Gly Asn Ser Phe Ser Ser Arg Pro Val Ile Val
                565             570             575

Lys His Lys Ser Tyr Ser Met Tyr His Leu Ser Ala Glu Ser Leu Gln
                580             585             590

Glu Ile Ile Thr Glu Phe Pro Thr Lys Phe Val Ala Ile Val Ile Leu
                595             600             605
```

-continued

```
Cys Leu Ile Thr Tyr Trp Ile Pro Phe Met Lys Tyr Glu Ala Gly Ala
        610                 615                 620

Phe Phe Gln Tyr Ile Leu Tyr Leu Leu Thr Val Gln Gln Cys Thr Ser
625                 630                 635                 640

Phe Ile Phe Lys Phe Val Ala Thr Met Ser Lys Ser Gly Val Asp Ala
                645                 650                 655

His Ala Val Gly Gly Leu Trp Val Leu Met Leu Cys Val Tyr Ala Gly
            660                 665                 670

Phe Val Leu Pro Ile Gly Glu Met His His Trp Ile Arg Trp Leu His
            675                 680                 685

Phe Ile Asn Pro Leu Thr Tyr Ala Phe Glu Ser Leu Val Ser Thr Glu
        690                 695                 700

Phe His His Arg Glu Met Leu Cys Ser Ala Leu Val Pro Ser Gly Pro
705                 710                 715                 720

Gly Tyr Glu Gly Ile Ser Ile Ala Asn Gln Val Cys Asp Ala Ala Gly
                725                 730                 735

Ala Val Lys Gly Asn Leu Tyr Val Ser Gly Asp Ser Tyr Ile Leu His
            740                 745                 750

Gln Tyr His Phe Ala Tyr Lys His Ala Trp Arg Asn Trp Gly Val Asn
        755                 760                 765

Ile Val Trp Thr Phe Gly Tyr Ile Val Phe Asn Val Ile Leu Ser Glu
770                 775                 780

Tyr Leu Lys Pro Val Glu Gly Gly Asp Leu Leu Tyr Lys Arg
785                 790                 795                 800

Gly His Met Pro Glu Leu Gly Thr Glu Asn Ala Asp Ala Arg Thr Ala
                805                 810                 815

Ser Arg Glu Glu Met Met Glu Ala Leu Asn Gly Pro Asn Val Asp Leu
            820                 825                 830

Glu Lys Val Ile Ala Glu Lys Asp Val Phe Thr Trp Asn His Leu Asp
        835                 840                 845

Tyr Thr Ile Pro Tyr Asp Gly Ala Thr Arg Lys Leu Leu Ser Asp Val
850                 855                 860

Phe Gly Tyr Val Lys Pro Gly Lys Met Thr Ala Leu Met Gly Glu Ser
865                 870                 875                 880

Gly Ala Gly Lys Thr Thr Leu Leu Asn Val Leu Ala Gln Arg Ile Asn
                885                 890                 895

Met Gly Val Ile Thr Gly Asp Met Leu Val Asn Ala Lys Pro Leu Pro
            900                 905                 910

Ala Ser Phe Asn Arg Ser Cys Gly Tyr Val Ala Gln Ala Asp Asn His
        915                 920                 925

Met Ala Glu Leu Ser Val Arg Glu Ser Leu Arg Phe Ala Ala Glu Leu
930                 935                 940

Arg Gln Gln Ser Ser Val Pro Leu Glu Glu Lys Tyr Glu Tyr Val Glu
945                 950                 955                 960

Lys Ile Ile Thr Leu Leu Gly Met Gln Asn Tyr Ala Glu Ala Leu Val
                965                 970                 975

Gly Lys Thr Gly Arg Gly Leu Asn Val Glu Gln Arg Lys Lys Leu Ser
            980                 985                 990

Ile Gly Val Glu Leu Val Ala Lys  Pro Ser Leu Leu  Phe Leu Asp
        995                 1000                1005

Glu Pro Thr Ser Gly Leu Asp  Ser Gln Ser Ala Trp  Ser Ile Val
    1010                1015                1020
```

```
Gln Phe Met Arg Ala Leu Ala Asp Ser Gly Gln Ser Ile Leu Cys
1025                1030                1035

Thr Ile His Gln Pro Ser Ala Thr Leu Phe Glu Gln Phe Asp Arg
1040                1045                1050

Leu Leu Leu Leu Lys Lys Gly Gly Lys Met Val Tyr Phe Gly Asp
1055                1060                1065

Ile Gly Pro Asn Ser Glu Thr Leu Leu Lys Tyr Phe Glu Arg Gln
1070                1075                1080

Ser Gly Met Lys Cys Gly Val Ser Glu Asn Pro Ala Glu Tyr Ile
1085                1090                1095

Leu Asn Cys Ile Gly Ala Gly Ala Thr Ala Ser Val Asn Ser Asp
1100                1105                1110

Trp His Asp Leu Trp Leu Ala Ser Pro Glu Cys Ala Ala Ala Arg
1115                1120                1125

Ala Glu Val Glu Glu Leu His Arg Thr Leu Pro Gly Arg Ala Val
1130                1135                1140

Asn Asp Asp Pro Glu Leu Ala Thr Arg Phe Ala Ala Ser Tyr Met
1145                1150                1155

Thr Gln Ile Lys Cys Val Leu Arg Arg Thr Ala Leu Gln Phe Trp
1160                1165                1170

Arg Ser Pro Val Tyr Ile Arg Ala Lys Phe Phe Glu Cys Val Ala
1175                1180                1185

Cys Ala Leu Phe Val Gly Leu Ser Tyr Val Gly Val Asn His Ser
1190                1195                1200

Val Gly Gly Ala Ile Glu Ala Phe Ser Ser Ile Phe Met Leu Leu
1205                1210                1215

Leu Ile Ala Leu Ala Met Ile Asn Gln Leu His Val Phe Ala Tyr
1220                1225                1230

Asp Ser Arg Glu Leu Tyr Glu Val Arg Glu Ala Ala Ser Asn Thr
1235                1240                1245

Phe His Trp Ser Val Leu Leu Leu Cys His Ala Ala Val Glu Asn
1250                1255                1260

Phe Trp Ser Thr Leu Cys Gln Phe Met Cys Phe Ile Cys Tyr Tyr
1265                1270                1275

Trp Pro Ala Gln Phe Ser Gly Arg Ala Ser His Ala Gly Phe Phe
1280                1285                1290

Phe Phe Phe Tyr Val Leu Ile Phe Pro Leu Tyr Phe Val Thr Tyr
1295                1300                1305

Gly Leu Trp Ile Leu Tyr Met Ser Pro Asp Val Pro Ser Ala Ser
1310                1315                1320

Met Ile Asn Ser Asn Leu Phe Ala Ala Met Leu Leu Phe Cys Gly
1325                1330                1335

Ile Leu Gln Pro Arg Glu Lys Met Pro Ala Phe Trp Arg Arg Leu
1340                1345                1350

Met Tyr Asn Val Ser Pro Phe Thr Tyr Val Val Gln Ala Leu Val
1355                1360                1365

Thr Pro Leu Val His Asn Lys Lys Val Val Cys Asn Pro His Glu
1370                1375                1380

Tyr Asn Ile Met Asp Pro Pro Ser Gly Lys Thr Cys Gly Glu Phe
1385                1390                1395

Leu Ser Thr Tyr Met Asp Asn Asn Thr Gly Tyr Leu Val Asn Pro
1400                1405                1410

Thr Ala Thr Glu Asn Cys Gln Tyr Cys Pro Tyr Thr Val Gln Asp
```

```
                1415                1420                1425

Gln Val Val Ala Lys Tyr Asn Val Lys Trp Asp His Arg Trp Arg
    1430                1435                1440

Asn Phe Gly Phe Met Trp Ala Tyr Ile Cys Phe Asn Ile Ala Ala
    1445                1450                1455

Met Leu Ile Cys Tyr Tyr Val Val Arg Val Lys Val Trp Ser Leu
    1460                1465                1470

Lys Ser Val Leu Asn Phe Lys Lys Trp Phe Asn Gly Pro Arg Lys
    1475                1480                1485

Glu Arg His Glu Lys Asp Thr Asn Ile Phe Gln Thr Val Pro Gly
    1490                1495                1500

Asp Glu Asn Lys Ile Thr Lys Lys
    1505                1510

<210> SEQ ID NO 8
<211> LENGTH: 944
<212> TYPE: PRT
<213> ORGANISM: Saccharomyces cerevisiae

<400> SEQUENCE: 8

Met Asp Thr Gln Ile Ala Ile Thr Gly Val Ala Val Gly Lys Glu Ile
1               5                   10                  15

Asn Asn Asp Asn Ser Lys Thr Asp Gln Lys Val Ser Leu Pro Lys Ala
                20                  25                  30

Asp Val Pro Cys Ile Asp Lys Ala Thr Gln Thr Ile Ile Glu Gly Cys
            35                  40                  45

Ser Lys Asp Asp Pro Arg Leu Ser Tyr Pro Thr Lys Leu Glu Thr Thr
        50                  55                  60

Glu Lys Gly Lys Thr Lys Arg Asn Ser Phe Ala Cys Val Cys Cys His
65                  70                  75                  80

Ser Leu Lys Gln Lys Cys Glu Pro Ser Asp Val Asn Asp Ile Tyr Arg
                85                  90                  95

Lys Pro Cys Arg Arg Cys Leu Lys His Lys Lys Leu Cys Lys Phe Asp
            100                 105                 110

Leu Ser Lys Thr Arg Lys Arg Lys Pro Arg Ser Arg Ser Pro Thr
        115                 120                 125

Pro Phe Glu Ser Pro Met Val Asn Val Ser Thr Lys Ser Lys Gly Pro
    130                 135                 140

Thr Asp Ser Glu Glu Ser Ser Leu Lys Asp Gly Thr Ser Tyr Leu Ala
145                 150                 155                 160

Ser Phe Pro Ser Asp Pro Asn Ala Lys Gln Phe Pro Asn Ser Arg Thr
                165                 170                 175

Val Leu Pro Gly Leu Gln Gln Ser Leu Ser Asp Leu Trp Ser Thr Leu
            180                 185                 190

Ser Gln Pro Pro Ser Tyr Gly Ala Arg Glu Ala Glu Thr Thr Ser Thr
        195                 200                 205

Gly Glu Ile Thr Thr Asn Asn His Thr Lys Ser Asn Gly Ser Val Pro
    210                 215                 220

Thr Asn Pro Ala Val Leu Ala Ser Asn Asp Glu His Thr Asn Ile Ser
225                 230                 235                 240

Asp Ala Pro Val Ile Tyr Ser Thr Tyr Asn Ser Pro Val Pro Ile Ser
                245                 250                 255

Ser Ala Pro Thr Ser Ile Asn Ser Glu Ala Leu Phe Lys His Arg Pro
            260                 265                 270
```

```
Lys Ile Val Gly Asp Glu Glu Thr Gln Asn Val Lys Val Lys Arg Gln
            275                 280                 285

Lys Lys Ser Tyr Ser Arg His Met Thr Arg Ser Phe Arg Lys Gln Leu
            290                 295                 300

Gln Ser Leu Ile Ile Ser Gln Lys Gly Lys Ile Arg Asp Ile Ser Met
305                 310                 315                 320

Lys Leu Asp Thr Trp Ser Lys Gln Trp Asn Asp Leu Val Glu Lys Ser
                325                 330                 335

Met Phe Leu Pro Thr Ile Ala Asp Pro Val Ser Val Gly Ile Ile Ser
                340                 345                 350

His Glu Glu Ala Thr Leu Arg Leu His Leu Tyr Lys Thr Glu Ile Ser
            355                 360                 365

Tyr Leu Ser Lys Leu Pro Phe Ile Lys Val Glu Glu Asn Val Ser Val
            370                 375                 380

Asp Glu Leu Arg Lys Lys Pro Ile Leu Phe Ser Val Ile Met Ser
385                 390                 395                 400

Cys Val Ser Ile Val Leu Thr Pro Lys Gln Thr Thr Arg Gly Thr Ile
                405                 410                 415

Met Lys Leu Asp Ser Phe Val Leu Asn Leu Ile Thr Asn Gln Ile Phe
                420                 425                 430

Lys Ala Asn Asn Lys Ser Ile Glu Ile Ile Glu Ser Leu Ser Thr Leu
            435                 440                 445

Cys Leu Trp Tyr Asn Phe Phe Glu Trp Ser Ser Lys Thr Arg Tyr His
            450                 455                 460

Ile Phe Asn Tyr Ile Cys Cys Cys Leu Thr Arg Asp Leu Gly Pro Thr
465                 470                 475                 480

Tyr Val Asn Arg Ser Phe Gly Met Phe Ser Asp Glu Asp Pro Lys Arg
                485                 490                 495

Phe Lys Ser Pro Leu Glu Leu Tyr Ser Asn Gly Ala Ser Leu Thr Leu
                500                 505                 510

Leu Val Tyr Ile Ser Ala Leu Asn Ile Ser Ile Phe Leu Arg Gln Ser
            515                 520                 525

Ile Gln Ala Arg Trp Ser His Val Thr Glu Lys Ala Cys Glu Asp Leu
530                 535                 540

Val Lys Glu Thr Lys Lys Ser Arg His Tyr Asp Asn Asp Lys Leu Leu
545                 550                 555                 560

Leu Asp Ser Ala Asp Asp Pro Ile Leu Val Gln Phe Ala Lys Met Asn
                565                 570                 575

His Val Leu Glu Asn Ile His Thr His Leu His Glu Arg Asp Leu Asn
            580                 585                 590

Asp Asp Glu Phe Asp Asp Pro Ile Phe Thr Lys Lys Tyr Leu Asn Lys
            595                 600                 605

Leu Met Glu Lys Tyr His Lys Gln Leu Gln Glu Ile Phe Thr Lys Leu
610                 615                 620

Asp Arg Asn Arg Pro Arg Val Ile Ala Phe Tyr Tyr Ser Val Glu Ala
625                 630                 635                 640

Tyr Leu Tyr Gln Tyr Lys Leu Ala Val Phe Ile Gly Glu Met Ser His
                645                 650                 655

Thr Ile Asn Glu Lys Val Glu Leu Pro Arg Glu Ile Met Asp Asp Phe
            660                 665                 670

Val Lys Cys Tyr His Cys Cys Lys Ser Ala Leu Glu Glu Phe Ser Lys
            675                 680                 685

Leu Glu Pro Ile Leu Ile Thr Ser Leu Pro Leu Phe His Thr Ser Arg
```

```
            690                 695                 700
Ile Ile Tyr Thr Val Gly Met Leu Leu Lys Leu Arg Tyr Ser Val
705                 710                 715                 720

Val Ala Ile Pro Ser Phe His Asp Leu Met Pro Leu Thr Asp Asp Ala
                725                 730                 735

Ile Ala Leu Val Ile Gly Val Asn Asn Leu Leu Glu Lys Thr Ser Glu
                740                 745                 750

Leu Tyr Pro Phe Asn Asn Ser Leu Tyr Lys Phe Arg Tyr Val Ile Ala
                755                 760                 765

Leu Phe Cys Gln Thr Tyr Ala Asn Lys Val Ile Asp Val Ala Asp Arg
            770                 775                 780

Tyr Asn Ala Glu Arg Glu Lys Leu Lys Glu Lys Gln Val Ile Asp Glu
785                 790                 795                 800

Val Ser Asn Gly His Asp Gly Thr Lys Pro Ile Asn Ala Tyr Val Thr
                805                 810                 815

Glu Ser Gln Lys Met Pro Thr Glu Gly Asp Pro Ile Ile Asp Asn Asn
                820                 825                 830

Thr Asn Gln Asn Ile Thr Ala Val Pro Asp Glu Met Leu Pro Val Tyr
            835                 840                 845

Ser Arg Val Arg Asp Asp Thr Ala Ala Met Asn Leu Asn Ile Asn Ser
            850                 855                 860

Thr Ser Tyr Met Asn Glu Ser Pro His Glu His Arg Glu Ser Met Thr
865                 870                 875                 880

Gly Thr Thr Leu Leu Pro Pro Pro Phe Ile Ser Asn Asp Val Thr Asn
                885                 890                 895

Ser Ala Asp Ser Thr Asn Ile Lys Pro Ser Pro Ser Ser Ser Val Asp
                900                 905                 910

Asn Leu Asn Asp Tyr Leu Thr Asp Ile Asn Ser Leu Ala Trp Gly Val
            915                 920                 925

Asn Ser Leu Asn Asp Glu Phe Trp Thr Asp Leu Phe Met Asn Asp Ile
            930                 935                 940

<210> SEQ ID NO 9
<211> LENGTH: 438
<212> TYPE: PRT
<213> ORGANISM: Schizosaccharomyces pombe

<400> SEQUENCE: 9

Met Gly Glu Leu Lys Glu Ile Leu Lys Gln Arg Tyr His Glu Leu Leu
1               5                   10                  15

Asp Trp Asn Val Lys Ala Pro His Val Pro Leu Ser Gln Arg Leu Lys
                20                  25                  30

His Phe Thr Trp Ser Trp Phe Ala Cys Thr Met Ala Thr Gly Gly Val
            35                  40                  45

Gly Leu Ile Ile Gly Ser Phe Pro Phe Arg Phe Tyr Gly Leu Asn Thr
        50                  55                  60

Ile Gly Lys Ile Val Tyr Ile Leu Gln Ile Phe Leu Phe Ser Leu Phe
65              70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
                100                 105                 110

Leu Ser Ile Ser Thr Phe Ile Asp Met Leu Ala Ile Tyr Ala Tyr Pro
            115                 120                 125
```

Asp Thr Gly Glu Trp Met Val Trp Val Ile Arg Ile Leu Tyr Tyr Ile
    130                 135                 140

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175

Leu Pro Ile Phe Pro Pro Met Ile Cys Gly Val Ile Ala Gly Ala Val
            180                 185                 190

Asn Ser Thr Gln Pro Ala His Gln Leu Lys Asn Met Val Ile Phe Gly
        195                 200                 205

Ile Leu Phe Gln Gly Leu Gly Phe Trp Val Tyr Leu Leu Leu Phe Ala
    210                 215                 220

Val Asn Val Leu Arg Phe Phe Thr Val Gly Leu Ala Lys Pro Gln Asp
225                 230                 235                 240

Arg Pro Gly Met Phe Met Phe Val Gly Pro Pro Ala Phe Ser Gly Leu
                245                 250                 255

Ala Leu Ile Asn Ile Ala Arg Gly Ala Met Gly Ser Arg Pro Tyr Ile
            260                 265                 270

Phe Val Gly Ala Asn Ser Ser Glu Tyr Leu Gly Phe Val Ser Thr Phe
        275                 280                 285

Met Ala Ile Phe Ile Trp Gly Leu Ala Ala Trp Cys Tyr Cys Leu Ala
    290                 295                 300

Met Val Ser Phe Leu Ala Gly Phe Phe Thr Arg Ala Pro Leu Lys Phe
305                 310                 315                 320

Ala Cys Gly Trp Phe Ala Phe Ile Phe Pro Asn Val Gly Phe Val Asn
                325                 330                 335

Cys Thr Ile Glu Ile Gly Lys Met Ile Asp Ser Lys Ala Phe Gln Met
            340                 345                 350

Phe Gly His Ile Ile Gly Val Ile Leu Cys Ile Gln Trp Ile Leu Leu
        355                 360                 365

Met Tyr Leu Met Val Arg Ala Phe Leu Val Asn Asp Leu Cys Tyr Pro
    370                 375                 380

Gly Lys Asp Glu Asp Ala His Pro Pro Lys Pro Asn Thr Gly Val
385                 390                 395                 400

Leu Asn Pro Thr Phe Pro Pro Glu Lys Ala Pro Ala Ser Leu Glu Lys
                405                 410                 415

Val Asp Thr His Val Thr Ser Thr Gly Gly Glu Ser Asp Pro Pro Ser
            420                 425                 430

Ser Glu His Glu Ser Val
        435

<210> SEQ ID NO 10
<211> LENGTH: 1517
<212> TYPE: PRT
<213> ORGANISM: Kluyveromyces marxianus

<400> SEQUENCE: 10

Met Ser Asn Ser Ser Ser Ser Glu Gly Lys Thr Asn Glu Asp Gly Arg
1               5                   10                  15

Asn Ser Val His Ser Ser Asp Ser Phe Ala Gln Ser Val Ala Ser Phe
            20                  25                  30

His Leu Asp Asp Asn Glu Ser Gln Asn Val Thr Ala Gln Leu Ser Gln
        35                  40                  45

Gln Ile Thr Asn Val Leu Ser Asn Ser Asn Gly Ala Glu Arg Ile Glu
    50                  55                  60

```
Ser Leu Ala Arg Val Ile Ser Thr Lys Thr Lys Lys Gln Met Glu Ser
 65                  70                  75                  80

Phe Glu Val Asn Gln Leu Asp Phe Asp Leu Lys Ala Leu Leu Asn Tyr
                 85                  90                  95

Leu Arg Ser Ser Gln Leu Glu Gln Gly Ile Glu Pro Gly Asp Ser Gly
            100                 105                 110

Ile Ala Phe His Asp Leu Thr Ala Val Gly Ile Asp Ala Ser Ala Ala
            115                 120                 125

Phe Gly Pro Ser Val Glu Glu Met Val Arg Ser Trp Ile His Phe Pro
130                 135                 140

Val Arg Leu Trp Lys Lys Ile Cys Arg Gln Lys Ser Glu Thr Pro Leu
145                 150                 155                 160

Arg Asn Ile Ile Gln His Cys Thr Gly Val Val Glu Ser Gly Glu Met
                165                 170                 175

Leu Phe Val Val Gly Arg Pro Gly Ala Gly Cys Ser Thr Leu Leu Lys
            180                 185                 190

Cys Leu Ser Gly Glu Thr Gly Glu Leu Val Glu Val Thr Gly Asp Ile
            195                 200                 205

Ser Tyr Asp Gly Leu Ser Gln Glu Glu Met Met Gln Lys Phe Lys Gly
210                 215                 220

Tyr Val Ile Tyr Cys Pro Glu Leu Asp Phe His Phe Pro Lys Ile Thr
225                 230                 235                 240

Val Lys Glu Thr Ile Asp Phe Ala Leu Lys Cys Lys Thr Pro Arg Ser
                245                 250                 255

Arg Ile Asp His Leu Thr Arg Ala Gln Tyr Val Asp Asn Met Arg Asp
            260                 265                 270

Leu Trp Cys Thr Val Phe Gly Leu Thr His Thr Tyr Ala Thr Asn Val
            275                 280                 285

Gly Asn Asp Val Val Arg Gly Val Ser Gly Gly Glu Arg Lys Arg Val
            290                 295                 300

Ser Leu Val Glu Ala Leu Ala Met Asn Ala Ser Ile Tyr Ser Trp Asp
305                 310                 315                 320

Asn Ala Thr Arg Gly Leu Asp Ala Ser Thr Ala Leu Glu Phe Ala Gln
                325                 330                 335

Ala Ile Arg Thr Ala Thr Asn Met Met Asn Asn Ser Ala Ile Val Ala
            340                 345                 350

Ile Tyr Gln Ala Gly Glu Asn Ile Tyr Gln Leu Phe Asp Lys Thr Thr
            355                 360                 365

Val Leu Tyr Asn Gly Lys Gln Val Tyr Phe Gly Pro Ala Asp Glu Ala
            370                 375                 380

Val Gly Tyr Phe Glu Arg Met Gly Tyr Ile Lys Pro Asn Arg Met Thr
385                 390                 395                 400

Ser Ala Glu Phe Leu Thr Ser Ala Thr Val Asp Phe Glu Asn Arg Thr
                405                 410                 415

Leu Glu Val Arg Glu Gly Tyr Glu Glu Lys Ile Pro Lys Ser Ser Thr
            420                 425                 430

Glu Met Glu Ala Tyr Trp His Asn Ser Pro Glu Tyr Ala Lys Ala Thr
            435                 440                 445

Glu Leu Phe Asn Glu Tyr Cys Gln Ser His Pro Glu Glu Glu Thr Arg
            450                 455                 460

Gln Arg Leu Glu Thr Ala Lys Lys Gln Arg Leu Gln Lys Gly Gln Arg
465                 470                 475                 480
```

Glu Lys Ser Gln Phe Val Val Thr Phe Trp Ala Gln Val Trp Tyr Cys
            485                 490                 495

Met Ile Arg Gly Phe Gln Arg Val Lys Gly Asp Ser Thr Tyr Thr Lys
            500                 505                 510

Val Tyr Leu Ser Ser Phe Leu Thr Lys Gly Leu Ile Val Gly Ser Met
            515                 520                 525

Phe His Lys Ile Asp Pro Lys Ser Gln Ser Thr Thr Glu Gly Ala Tyr
            530                 535                 540

Ser Arg Gly Gly Leu Leu Phe Tyr Val Leu Leu Phe Ala Ala Leu Thr
545                 550                 555                 560

Ser Leu Ala Glu Ile Ser Asn Ser Phe Gln Asn Arg Ala Ile Ile Val
            565                 570                 575

Lys Gln Lys Thr Tyr Ser Met Tyr His Thr Ser Ala Glu Ser Leu Gln
            580                 585                 590

Glu Ile Phe Thr Glu Ile Pro Thr Lys Phe Val Ala Ile Leu Thr Leu
            595                 600                 605

Ser Leu Val Ser Tyr Trp Ile Pro Val Leu Lys Tyr Asp Ala Gly Ser
            610                 615                 620

Phe Phe Gln Tyr Leu Leu Tyr Leu Phe Thr Thr Gln Gln Cys Thr Ser
625                 630                 635                 640

Phe Ile Phe Lys Leu Val Ala Thr Leu Thr Lys Asp Gly Gly Thr Ala
            645                 650                 655

His Ala Ile Gly Gly Leu Trp Val Leu Met Leu Thr Val Tyr Ala Gly
            660                 665                 670

Phe Val Leu Pro Ile Gly Asn Met His His Trp Ile Arg Trp Phe His
            675                 680                 685

Tyr Leu Asn Pro Leu Thr Tyr Ala Tyr Glu Ser Leu Met Ser Thr Glu
            690                 695                 700

Phe His Gly Arg Lys Met Leu Cys Ser Arg Leu Leu Pro Ser Gly Pro
705                 710                 715                 720

Gly Tyr Glu Asn Val Ser Ile Ala His Lys Ile Cys Asp Ala Ala Gly
            725                 730                 735

Ala Val Ala Gly Gln Leu Tyr Val Ser Gly Asp Ala Tyr Val Leu Lys
            740                 745                 750

Lys Tyr His Phe Arg Tyr Lys His Ala Trp Arg Asp Trp Gly Ile Asn
            755                 760                 765

Ile Val Trp Thr Phe Gly Tyr Ile Val Met Asn Val Val Met Ser Glu
            770                 775                 780

Tyr Leu Lys Pro Leu Glu Gly Gly Asp Leu Leu Tyr Lys Arg
785                 790                 795                 800

Gly His Met Pro Glu Leu Gly Ser Glu Ser Val Asp Ser Lys Val Ala
            805                 810                 815

Ser Arg Glu Glu Met Met Glu Ser Leu Asn Gly Pro Gly Val Asp Leu
            820                 825                 830

Glu Lys Val Ile Ala Ser Lys Asp Val Phe Thr Trp Asn His Leu Asn
            835                 840                 845

Tyr Thr Ile Pro Tyr Asp Gly Ala Thr Arg Gln Leu Leu Ser Asp Val
            850                 855                 860

Phe Gly Tyr Val Lys Pro Gly Lys Met Thr Ala Leu Met Gly Glu Ser
865                 870                 875                 880

Gly Ala Gly Lys Thr Thr Leu Leu Asn Val Leu Ala Gln Arg Ile Asn
            885                 890                 895

Val Gly Val Ile Thr Gly Asp Met Leu Val Asn Ala Lys Pro Leu Pro

-continued

```
                900             905             910
Pro Ser Phe Asn Arg Ser Cys Gly Tyr Val Ala Gln Ala Asp Asn His
            915             920             925
Met Gly Glu Leu Ser Val Arg Glu Ser Leu Arg Phe Ala Ala Glu Leu
            930             935             940
Arg Gln Pro Lys Ser Val Pro Leu Gln Glu Lys Tyr Asp Tyr Val Glu
945             950             955             960
Lys Ile Ile Ser Leu Leu Gly Met Glu Lys Tyr Ala Glu Ala Ile Ile
            965             970             975
Gly Lys Thr Gly Arg Gly Leu Asn Val Glu Gln Arg Lys Lys Leu Ser
            980             985             990
Ile Gly Val Glu Leu Val Ala Lys  Pro Ser Leu Leu Leu  Phe Leu Asp
            995             1000            1005
Glu Pro  Thr Ser Gly Leu Asp  Ser Gln Ser Ala Trp  Ser Ile Val
    1010            1015            1020
Gln Phe  Met Arg Ala Leu Ala  Asp Ser Gly Gln Ser  Ile Leu Cys
    1025            1030            1035
Thr Ile  His Gln Pro Ser Ala  Thr Leu Phe Glu Gln  Phe Asp Arg
    1040            1045            1050
Leu Leu  Leu Leu Lys Lys Gly  Gly Lys Met Val Tyr  Phe Gly Asp
    1055            1060            1065
Ile Gly  Glu Asn Ser Ser Thr  Leu Leu Asn Tyr Phe  Glu Arg Gln
    1070            1075            1080
Ser Gly  Val Lys Cys Gly Lys  Ser Glu Asn Pro Ala  Glu Tyr Met
    1085            1090            1095
Leu Asn  Cys Ile Gly Ala Gly  Ala Thr Ala Ser Ala  Asp Ala Asp
    1100            1105            1110
Trp His  Asp Leu Trp Leu Gln  Ser Pro Glu Cys Ala  Ala Ala Arg
    1115            1120            1125
Glu Glu  Val Glu Glu Leu His  Arg Thr Leu Ala Ser  Arg Pro Val
    1130            1135            1140
Thr Asp  Asp Lys Glu Leu Ala  Gly Arg Tyr Ala Ala  Ser Tyr Leu
    1145            1150            1155
Thr Gln  Met Lys Cys Val Phe  Arg Arg Thr Asn Ile  Gln Phe Trp
    1160            1165            1170
Arg Ser  Pro Val Tyr Ile Arg  Ala Lys Phe Leu Glu  Cys Val Leu
    1175            1180            1185
Cys Ala  Leu Phe Val Gly Leu  Ser Tyr Val Gly Val  Asp His Ser
    1190            1195            1200
Ile Ala  Gly Ala Ser Gln Ser  Phe Ser Ser Ile Phe  Met Met Leu
    1205            1210            1215
Leu Ile  Ala Leu Ala Met Val  Asn Gln Leu His Val  Phe Ala Leu
    1220            1225            1230
Asp Ser  Arg Glu Leu Tyr Glu  Val Arg Glu Ala Ala  Ser Asn Thr
    1235            1240            1245
Phe His  Trp Ser Val Leu Leu  Leu Asn His Thr Phe  Val Glu Ile
    1250            1255            1260
Ile Trp  Ser Thr Leu Cys Glu  Phe Ile Cys Trp Ile  Cys Tyr Tyr
    1265            1270            1275
Trp Pro  Ala Gln Tyr Ser Gly  Arg Ala Ser His Ala  Gly Tyr Phe
    1280            1285            1290
Phe Leu  Ile Tyr Val Ile Met  Phe Pro Ala Tyr Phe  Val Ser Tyr
    1295            1300            1305
```

-continued

Gly Cys Trp Val Phe Tyr Met Ser Pro Asp Val Pro Ser Ala Ser
    1310                1315                1320

Met Ile Asn Ser Asn Leu Phe Ala Gly Met Leu Leu Phe Cys Gly
    1325                1330                1335

Ile Leu Gln Pro Lys Asp Lys Met Pro Gly Phe Trp Lys Arg Phe
    1340                1345                1350

Met Tyr Asn Val Ser Pro Phe Thr Tyr Val Val Gln Ser Leu Val
    1355                1360                1365

Thr Pro Leu Val Gln Gly Lys Lys Val Arg Cys Thr Lys Asn Glu
    1370                1375                1380

Phe Ala Val Val Asn Pro Pro Glu Gly Gln Thr Cys Ser Gln Tyr
    1385                1390                1395

Phe Ala Arg Phe Ile Lys Asp Asn Thr Gly Tyr Leu Lys Asn Pro
    1400                1405                1410

Asn Asp Thr Glu Ser Cys His Tyr Cys Pro Tyr Ser Tyr Gln Gln
    1415                1420                1425

Glu Val Val Glu Gln Tyr Asn Val Arg Trp Val Tyr Arg Trp Arg
    1430                1435                1440

Asn Phe Gly Phe Leu Trp Ala Tyr Ile Gly Phe Asn Phe Phe Ala
    1445                1450                1455

Met Leu Ala Cys Tyr Trp Val Leu Arg Val Lys Asn Tyr Ser Ile
    1460                1465                1470

Thr Ser Ile Phe Gly Val Phe Lys Ile Gly Asn Trp Lys Lys Ala
    1475                1480                1485

Ile His His Asp Ser Arg His Glu Lys Asp His Thr Ile Phe Gln
    1490                1495                1500

Glu Lys Pro Gly Asp Ala Ala Asn Val Gln Lys Thr Lys Ala
    1505                1510                1515

<210> SEQ ID NO 11
<211> LENGTH: 575
<212> TYPE: PRT
<213> ORGANISM: Pichia kudriavzevii

<400> SEQUENCE: 11

Met Thr Asp Lys Ile Ser Leu Gly Thr Tyr Leu Phe Glu Lys Leu Lys
1               5                   10                  15

Glu Ala Gly Ser Tyr Ser Ile Phe Gly Val Pro Gly Asp Phe Asn Leu
                20                  25                  30

Ala Leu Leu Asp His Val Lys Glu Val Glu Gly Ile Arg Trp Val Gly
            35                  40                  45

Asn Ala Asn Glu Leu Asn Ala Gly Tyr Glu Ala Asp Gly Tyr Ala Arg
        50                  55                  60

Ile Asn Gly Phe Ala Ser Leu Ile Thr Thr Phe Gly Val Gly Glu Leu
65                  70                  75                  80

Ser Ala Val Asn Ala Ile Ala Gly Ser Tyr Ala Glu His Val Pro Leu
                85                  90                  95

Ile His Ile Val Gly Met Pro Ser Leu Ser Ala Met Lys Asn Asn Leu
            100                 105                 110

Leu Leu His His Thr Leu Gly Asp Thr Arg Phe Asp Asn Phe Thr Glu
        115                 120                 125

Met Ser Lys Lys Ile Ser Ala Lys Val Glu Ile Val Tyr Asp Leu Glu
    130                 135                 140

Ser Ala Pro Lys Leu Ile Asn Asn Leu Ile Glu Thr Ala Tyr His Thr

```
            145                 150                 155                 160
Lys Arg Pro Val Tyr Leu Gly Leu Pro Ser Asn Phe Ala Asp Glu Leu
                    165                 170                 175

Val Pro Ala Ala Leu Val Lys Glu Asn Lys Leu His Leu Glu Glu Pro
                180                 185                 190

Leu Asn Asn Pro Val Ala Glu Glu Phe Ile His Asn Val Val Glu
            195                 200                 205

Met Val Lys Lys Ala Glu Lys Pro Ile Ile Leu Val Asp Ala Cys Ala
    210                 215                 220

Ala Arg His Asn Ile Ser Lys Glu Val Arg Glu Leu Ala Lys Leu Thr
225                 230                 235                 240

Lys Phe Pro Val Phe Thr Thr Pro Met Gly Lys Ser Thr Val Asp Glu
                245                 250                 255

Asp Asp Glu Glu Phe Phe Gly Leu Tyr Leu Gly Ser Leu Ser Ala Pro
            260                 265                 270

Asp Val Lys Asp Ile Val Gly Pro Thr Asp Cys Ile Leu Ser Leu Gly
            275                 280                 285

Gly Leu Pro Ser Asp Phe Asn Thr Gly Ser Phe Ser Tyr Gly Tyr Thr
    290                 295                 300

Thr Lys Asn Val Val Glu Phe His Ser Asn Tyr Cys Lys Phe Lys Ser
305                 310                 315                 320

Ala Thr Tyr Glu Asn Leu Met Met Lys Gly Ala Val Gln Arg Leu Ile
                325                 330                 335

Ser Glu Leu Lys Asn Ile Lys Tyr Ser Asn Val Ser Thr Leu Ser Pro
            340                 345                 350

Pro Lys Ser Lys Phe Ala Tyr Glu Ser Ala Lys Val Ala Pro Glu Gly
            355                 360                 365

Ile Ile Thr Gln Asp Tyr Leu Trp Lys Arg Leu Ser Tyr Phe Leu Lys
    370                 375                 380

Pro Arg Asp Ile Ile Val Thr Glu Thr Gly Thr Ser Ser Phe Gly Val
385                 390                 395                 400

Leu Ala Thr His Leu Pro Arg Asp Ser Lys Ser Ile Ser Gln Val Leu
                405                 410                 415

Trp Gly Ser Ile Gly Phe Ser Leu Pro Ala Ala Val Gly Ala Ala Phe
            420                 425                 430

Ala Ala Glu Asp Ala His Lys Gln Thr Gly Glu Gln Gly Arg Arg Thr
            435                 440                 445

Val Leu Phe Ile Gly Asp Gly Ser Leu Gln Leu Thr Val Gln Ser Ile
    450                 455                 460

Ser Asp Ala Ala Arg Trp Asn Ile Lys Pro Tyr Ile Phe Ile Leu Asn
465                 470                 475                 480

Asn Arg Gly Tyr Thr Ile Glu Lys Leu Ile His Gly Arg His Glu Asp
                485                 490                 495

Tyr Asn Gln Ile Gln Pro Trp Asp His Gln Leu Leu Leu Lys Leu Phe
            500                 505                 510

Ala Asp Lys Thr Gln Tyr Glu Asn His Val Val Lys Ser Ala Lys Asp
            515                 520                 525

Leu Asp Ala Leu Met Lys Asp Glu Ala Phe Asn Lys Glu Asp Lys Ile
    530                 535                 540

Arg Val Ile Glu Leu Phe Leu Asp Glu Phe Asp Ala Pro Glu Ile Leu
545                 550                 555                 560

Val Ala Gln Ala Lys Leu Ser Asp Glu Ile Asn Ser Lys Ala Ala
                565                 570                 575
```

<210> SEQ ID NO 12
<211> LENGTH: 608
<212> TYPE: PRT
<213> ORGANISM: Pichia kudriavzevii

<400> SEQUENCE: 12

Met Leu Gln Thr Ala Asn Ser Glu Val Pro Asn Ala Ser Gln Ile Thr
1               5                   10                  15

Ile Asp Ala Ala Ser Gly Leu Pro Ala Asp Arg Val Leu Pro Asn Ile
            20                  25                  30

Thr Asn Thr Glu Ile Thr Ile Ser Glu Tyr Ile Phe Tyr Arg Ile Leu
        35                  40                  45

Gln Leu Gly Val Arg Ser Val Phe Gly Val Pro Gly Asp Phe Asn Leu
    50                  55                  60

Arg Phe Leu Glu His Ile Tyr Asp Val His Gly Leu Asn Trp Ile Gly
65                  70                  75                  80

Cys Cys Asn Glu Leu Asn Ala Ala Tyr Ala Ala Asp Ala Tyr Ala Lys
                85                  90                  95

Ala Ser Lys Lys Met Gly Val Leu Leu Thr Thr Tyr Gly Val Gly Glu
            100                 105                 110

Leu Ser Ala Leu Asn Gly Val Ala Gly Ala Tyr Thr Glu Phe Ala Pro
        115                 120                 125

Val Leu His Leu Val Gly Thr Ser Ala Leu Lys Phe Lys Arg Asn Pro
    130                 135                 140

Arg Thr Leu Asn Leu His His Leu Ala Gly Asp Lys Lys Thr Phe Lys
145                 150                 155                 160

Lys Ser Asp His Tyr Lys Tyr Glu Arg Ile Ala Ser Glu Phe Ser Val
                165                 170                 175

Asp Ser Ala Ser Ile Glu Asp Pro Ile Glu Ala Cys Glu Met Ile
            180                 185                 190

Asp Arg Val Ile Tyr Ser Thr Trp Arg Glu Ser Arg Pro Gly Tyr Ile
        195                 200                 205

Phe Leu Pro Cys Asp Leu Ser Glu Met Lys Val Asp Ala Gln Arg Leu
    210                 215                 220

Ala Ser Pro Ile Glu Leu Thr Tyr Arg Phe Asn Ser Pro Val Ser Arg
225                 230                 235                 240

Val Glu Gly Val Ala Asp Gln Ile Leu Gln Leu Ile Tyr Gln Asn Lys
                245                 250                 255

Asn Val Ser Ile Ile Val Asp Gly Phe Ile Arg Lys Phe Arg Met Glu
            260                 265                 270

Ser Glu Phe Tyr Asp Ile Met Glu Lys Phe Gly Asp Lys Val Asn Ile
        275                 280                 285

Phe Ser Thr Met Tyr Gly Lys Gly Leu Ile Gly Glu Glu His Pro Arg
    290                 295                 300

Phe Val Gly Thr Tyr Phe Gly Lys Tyr Glu Lys Ala Val Gly Asn Leu
305                 310                 315                 320

Leu Glu Ala Ser Asp Leu Ile Ile His Phe Gly Asn Phe Asp His Glu
                325                 330                 335

Leu Asn Met Gly Gly Phe Thr Phe Asn Ile Pro Gln Glu Lys Tyr Ile
            340                 345                 350

Asp Leu Ser Ala Gln Tyr Val Asp Ile Thr Gly Asn Leu Asp Glu Ser
        355                 360                 365

Ile Thr Met Met Glu Val Leu Pro Val Leu Ala Ser Lys Leu Asp Ser

```
            370                 375                 380
Ser Arg Val Asn Val Ala Asp Lys Phe Glu Lys Phe Asp Lys Tyr Tyr
385                 390                 395                 400

Glu Thr Pro Asp Tyr Gln Arg Glu Ala Ser Leu Gln Glu Thr Asp Ile
            405                 410                 415

Met Gln Ser Leu Asn Glu Asn Leu Thr Gly Asp Asp Ile Leu Ile Val
            420                 425                 430

Glu Thr Cys Ser Phe Leu Phe Ala Val Pro Asp Leu Lys Val Lys Gln
            435                 440                 445

His Thr Asn Ile Ile Leu Gln Ala Tyr Trp Ala Ser Ile Gly Tyr Ala
            450                 455                 460

Leu Pro Ala Thr Leu Gly Ala Ser Leu Ala Ile Arg Asp Phe Asn Leu
465                 470                 475                 480

Ser Gly Lys Val Tyr Thr Ile Glu Gly Asp Gly Ser Ala Gln Met Ser
            485                 490                 495

Leu Gln Glu Leu Ser Ser Met Leu Arg Tyr Asn Ile Asp Ala Thr Met
            500                 505                 510

Ile Leu Leu Asn Asn Ser Gly Tyr Thr Ile Glu Arg Val Ile Val Gly
            515                 520                 525

Pro His Ser Ser Tyr Asn Asp Ile Asn Thr Asn Trp Gln Trp Thr Asp
            530                 535                 540

Leu Leu Arg Ala Phe Gly Asp Val Ala Asn Glu Lys Ser Val Ser Tyr
545                 550                 555                 560

Thr Ile Lys Glu Arg Glu Gln Leu Leu Asn Ile Leu Ser Asp Pro Ser
            565                 570                 575

Phe Lys His Asn Gly Lys Phe Arg Leu Leu Glu Cys Val Leu Pro Met
            580                 585                 590

Phe Asp Val Pro Lys Lys Leu Gly Gln Phe Thr Gly Lys Ile Pro Ala
            595                 600                 605

<210> SEQ ID NO 13
<211> LENGTH: 584
<212> TYPE: PRT
<213> ORGANISM: Pichia kudriavzevii

<400> SEQUENCE: 13

Met Ala Pro Val Ser Leu Glu Thr Cys Thr Leu Glu Phe Ser Cys Lys
1               5                   10                  15

Leu Pro Leu Ser Glu Tyr Ile Phe Arg Arg Ile Ala Ser Leu Gly Ile
            20                  25                  30

His Asn Ile Phe Gly Val Pro Gly Asp Tyr Asn Leu Ser Phe Leu Glu
            35                  40                  45

His Leu Tyr Ser Val Pro Glu Leu Ser Trp Val Gly Cys Cys Asn Glu
            50                  55                  60

Leu Asn Ser Ala Tyr Ala Thr Asp Gly Tyr Ser Arg Thr Ile Gly His
65                  70                  75                  80

Asp Lys Phe Gly Val Leu Leu Thr Thr Gln Gly Val Gly Glu Leu Ser
            85                  90                  95

Ala Ala Asn Ala Ile Ala Gly Ser Phe Ala Glu His Val Pro Ile Leu
            100                 105                 110

His Ile Val Gly Thr Thr Pro Tyr Ser Leu Lys His Lys Gly Ser His
            115                 120                 125

His His His Leu Ile Asn Gly Val Ser Thr Arg Glu Pro Thr Asn His
            130                 135                 140
```

```
Tyr Ala Tyr Glu Glu Met Ser Lys Asn Ile Ser Cys Lys Ile Leu Ser
145                 150                 155                 160

Leu Ser Asp Asp Leu Thr Asn Ala Ala Asn Glu Ile Asp Asp Leu Phe
            165                 170                 175

Arg Thr Ile Leu Met Leu Lys Lys Pro Gly Tyr Leu Tyr Ile Pro Cys
        180                 185                 190

Asp Leu Val Asn Val Glu Ile Asp Ala Ser Asn Leu Gln Ser Val Pro
    195                 200                 205

Ala Asn Lys Leu Arg Glu Arg Val Pro Ser Thr Asp Ser Gln Thr Ile
210                 215                 220

Ala Lys Ile Thr Ser Thr Ile Val Asp Lys Leu Leu Ser Ser Ser Asn
225                 230                 235                 240

Pro Val Val Leu Cys Asp Ile Leu Thr Asp Arg Tyr Gly Met Thr Ala
                245                 250                 255

Tyr Ala Gln Asp Leu Val Asp Ser Leu Lys Val Pro Cys Cys Asn Ser
            260                 265                 270

Phe Met Gly Lys Ala Leu Leu Asn Glu Ser Lys Glu His Tyr Ile Gly
        275                 280                 285

Asp Phe Asn Gly Glu Glu Ser Asn Lys Met Val His Ser Tyr Ile Ser
    290                 295                 300

Asn Thr Asp Cys Phe Leu His Ile Gly Asp Tyr Tyr Asn Glu Ile Asn
305                 310                 315                 320

Ser Gly His Trp Ser Leu Tyr Asn Gly Ile Asn Lys Glu Ser Ile Val
                325                 330                 335

Ile Leu Asn Pro Glu Tyr Val Lys Ile Gly Ser Gln Thr Tyr Gln Asn
            340                 345                 350

Val Ser Phe Glu Asp Ile Leu Pro Ala Ile Leu Ser Ser Ile Lys Ala
        355                 360                 365

Asn Pro Asn Leu Pro Cys Phe His Ile Pro Lys Ile Met Ser Thr Ile
    370                 375                 380

Glu Gln Ile Pro Ser Asn Thr Pro Ile Ser Gln Thr Leu Met Leu Glu
385                 390                 395                 400

Lys Leu Gln Ser Phe Leu Lys Pro Asn Asp Val Leu Val Thr Glu Thr
                405                 410                 415

Cys Ser Leu Met Phe Gly Leu Pro Asp Ile Arg Met Pro Glu Asn Ser
            420                 425                 430

Lys Val Ile Gly Gln His Phe Tyr Leu Ser Ile Gly Met Ala Leu Pro
        435                 440                 445

Cys Ser Phe Gly Val Ser Val Ala Leu Asn Glu Leu Lys Lys Asp Ser
    450                 455                 460

Arg Leu Ile Leu Ile Glu Gly Asp Gly Ser Ala Gln Met Thr Val Gln
465                 470                 475                 480

Glu Leu Ser Asn Phe Asn Arg Glu Asn Val Val Lys Pro Leu Ile Ile
                485                 490                 495

Leu Leu Asn Asn Ser Gly Tyr Thr Val Glu Arg Val Ile Lys Gly Pro
            500                 505                 510

Lys Arg Glu Tyr Asn Asp Ile Arg Pro Asp Trp Lys Trp Thr Gln Leu
        515                 520                 525

Leu Gln Thr Phe Gly Met Asp Asp Ala Lys Ser Met Lys Val Thr Thr
    530                 535                 540

Pro Glu Glu Leu Asp Asp Ala Leu Asp Glu Tyr Gly Asn Asn Leu Ser
545                 550                 555                 560

Thr Pro Arg Leu Leu Glu Val Val Leu Asp Lys Leu Asp Val Pro Trp
```

Arg Phe Asn Lys Met Val Gly Asn
                580

<210> SEQ ID NO 14
<211> LENGTH: 407
<212> TYPE: PRT
<213> ORGANISM: Pichia kudriavzevii

<400> SEQUENCE: 14

Met Leu Arg Leu Phe Ser Arg Arg Thr Pro Ser Val Arg Ala Leu Pro
1               5                   10                  15

Lys Phe Thr Arg Ser Leu Ala Thr Ala Ser Pro Glu Ala Gly Ala Gln
                20                  25                  30

Glu Val Ser Asn Leu His Asp Ile Val Glu Ile Glu Leu Pro Glu Tyr
            35                  40                  45

Ser Phe Glu Gly Tyr Lys Leu Asp Val Pro Glu Leu Asn Tyr Ser Thr
        50                  55                  60

Glu Lys Gly Thr Leu Leu Gln Met Tyr Lys Asp Met Val Ile Ile Arg
65                  70                  75                  80

Arg Met Glu Met Ala Ala Asp Ala Leu Tyr Lys Ala Lys Lys Ile Arg
                85                  90                  95

Gly Phe Cys His Leu Ser Val Gly Gln Glu Ala Ile Ala Val Gly Ile
            100                 105                 110

Glu Asn Ala Ile Thr Lys Gln Asp Asp Ile Ile Thr Ser Tyr Arg Cys
        115                 120                 125

His Gly Thr Thr Tyr Met Arg Gly Ala Ser Val Gln Glu Val Leu Ala
130                 135                 140

Glu Leu Met Gly Arg Arg Ser Gly Val Ser Tyr Gly Lys Gly Gly Ser
145                 150                 155                 160

Met His Met Tyr Thr Lys Gly Phe Tyr Gly Gly Asn Gly Ile Val Gly
                165                 170                 175

Ala Gln Val Pro Leu Gly Thr Gly Leu Ala Phe Ala His His Tyr Arg
            180                 185                 190

Asp Gln Lys Asn Met Thr Trp Thr Met Tyr Gly Asp Gly Ala Ala Asn
        195                 200                 205

Gln Gly Gln Val Phe Glu Ser Phe Asn Met Ala Lys Leu Trp Asn Leu
210                 215                 220

Pro Cys Val Phe Thr Cys Glu Asn Asn Lys Tyr Gly Met Gly Thr Ser
225                 230                 235                 240

Ala Ser Arg Ser Ser Ala Met Thr Glu Tyr Tyr Lys Arg Gly Gln Tyr
                245                 250                 255

Ile Pro Gly Leu Lys Val Asn Gly Met Asp Ile Leu Ala Val Tyr Gln
            260                 265                 270

Ala Ala Lys Phe Ala Lys Glu Trp Thr Ser Asn Asp Asn Gly Pro Leu
        275                 280                 285

Val Ile Glu Phe Glu Thr Tyr Arg Tyr Gly Gly His Ser Met Ser Asp
290                 295                 300

Pro Gly Thr Thr Tyr Arg Thr Arg Glu Glu Val Gln Asn Met Arg Ser
305                 310                 315                 320

Lys Lys Asp Pro Ile Ala Gly Leu Lys Ala His Leu Leu Glu Phe Asn
                325                 330                 335

Ile Ala Thr Glu Glu Ile Lys Ala Phe Asp Lys Ser Ala Arg Lys
            340                 345                 350

```
Tyr Val Asp Glu Gln Val Lys Leu Ala Asp Ala Ser Pro Pro Glu
            355                 360                 365
Ala Lys Met Ser Ile Leu Phe Glu Asp Val Tyr Val Pro Gly Ser Glu
    370                 375                 380
Ile Pro Val Leu Arg Gly Arg Ile Arg Asp Asp Ser Trp Ser Phe Glu
385                 390                 395                 400
Lys Gly Gly Phe Ala Tyr Lys
                405

<210> SEQ ID NO 15
<211> LENGTH: 388
<212> TYPE: PRT
<213> ORGANISM: Pichia kudriavzevii

<400> SEQUENCE: 15

Met Val Ser Pro Ala Glu Arg Leu Ser Thr Ile Ala Ser Thr Ile Lys
1               5                   10                  15
Pro Asn Arg Lys Asp Ser Thr Ser Leu Gln Pro Glu Asp Tyr Pro Glu
                20                  25                  30
His Pro Phe Lys Val Thr Val Val Gly Ser Gly Asn Trp Gly Cys Thr
            35                  40                  45
Ile Ala Lys Val Ile Ala Glu Asn Thr Val Glu Arg Pro Arg Gln Phe
    50                  55                  60
Gln Arg Asp Val Asn Met Trp Val Tyr Glu Glu Leu Ile Glu Gly Glu
65                  70                  75                  80
Lys Leu Thr Glu Ile Ile Asn Thr Lys His Glu Asn Val Lys Tyr Leu
                85                  90                  95
Pro Gly Ile Lys Leu Pro Val Asn Val Ala Val Pro Asp Ile Val
                100                 105                 110
Glu Ala Cys Ala Gly Ser Asp Leu Ile Val Phe Asn Ile Pro His Gln
            115                 120                 125
Phe Leu Pro Arg Ile Leu Ser Gln Leu Lys Gly Lys Val Asn Pro Lys
    130                 135                 140
Ala Arg Ala Ile Ser Cys Leu Lys Gly Leu Asp Val Asn Pro Asn Gly
145                 150                 155                 160
Cys Lys Leu Leu Ser Thr Val Ile Thr Glu Glu Leu Gly Ile Tyr Cys
                165                 170                 175
Gly Ala Leu Ser Gly Ala Asn Leu Ala Pro Glu Val Ala Gln Cys Lys
            180                 185                 190
Trp Ser Glu Thr Thr Val Ala Tyr Thr Ile Pro Asp Asp Phe Arg Gly
    195                 200                 205
Lys Gly Lys Asp Ile Asp His Gln Ile Leu Lys Ser Leu Phe His Arg
210                 215                 220
Pro Tyr Phe His Val Arg Val Ile Ser Asp Val Ala Gly Ile Ser Ile
225                 230                 235                 240
Ala Gly Ala Leu Lys Asn Val Val Ala Met Ala Ala Gly Phe Val Glu
                245                 250                 255
Gly Leu Gly Trp Gly Asp Asn Ala Lys Ala Ala Val Met Arg Ile Gly
            260                 265                 270
Leu Val Glu Thr Ile Gln Phe Ala Lys Thr Phe Phe Asp Gly Cys His
    275                 280                 285
Ala Ala Thr Phe Thr His Glu Ser Ala Gly Val Ala Asp Leu Ile Thr
    290                 295                 300
Thr Cys Ala Gly Gly Arg Asn Val Arg Val Gly Arg Tyr Met Ala Gln
305                 310                 315                 320
```

His Ser Val Ser Ala Thr Glu Ala Glu Lys Leu Leu Asn Gly Gln
              325                 330                 335

Ser Cys Gln Gly Ile His Thr Thr Arg Glu Val Tyr Glu Phe Leu Ser
            340                 345                 350

Asn Met Gly Arg Thr Asp Glu Phe Pro Leu Phe Thr Thr Thr Tyr Arg
        355                 360                 365

Ile Ile Tyr Glu Asn Phe Pro Ile Glu Lys Leu Pro Glu Cys Leu Glu
    370                 375                 380

Pro Val Glu Asp
385

<210> SEQ ID NO 16
<211> LENGTH: 563
<212> TYPE: PRT
<213> ORGANISM: Pichia kudriavzevii

<400> SEQUENCE: 16

Met Ile Pro Arg Leu Asn Pro Leu Asn Ile Ser His Leu Arg Gly
1               5                   10                  15

Gly Pro Lys Phe Ile Gly Lys Ala Ile Lys Pro Ser Gln Phe Glu Phe
            20                  25                  30

Arg Lys Asn Asn Phe Arg Phe Asn Ser Thr Ser Thr Lys Thr Gly Ser
            35                  40                  45

Ala Arg Thr Ile Lys Ser Gly Phe Leu Ser Trp Ser Phe Arg Ala Ala
    50                  55                  60

Thr Phe Thr Gly Ile Ala Gly Trp Leu Tyr Leu Thr Tyr Leu Val Tyr
65                  70                  75                  80

Lys Glu Thr Asn Pro Gly Ser Gln Ser Pro Gln Thr Glu Phe Ser Glu
                85                  90                  95

Ile Gly Asn Lys Lys Asn Ile Val Ile Leu Gly Ser Gly Trp Gly
            100                 105                 110

Ala Val Ser Val Leu Lys Thr Leu Asp Thr Thr Lys Tyr Asn Val Thr
            115                 120                 125

Ile Val Ser Pro Arg Asn Tyr Phe Leu Phe Thr Pro Leu Leu Pro Ser
    130                 135                 140

Val Pro Ser Gly Thr Ile Asp Ile Lys Ser Ile Cys Asp Ser Ile Arg
145                 150                 155                 160

Thr Ile Ala Arg Gln Thr Pro Gly Glu Val Thr Tyr Leu Glu Ala Ala
                165                 170                 175

Ala Thr Asp Ile Asp Pro Val Lys Lys Thr Ile Lys Leu Glu His Lys
            180                 185                 190

Ser Gln Arg Phe Leu Ile Gly Asp Ala Phe Thr Ser Glu Gly Asp Val
            195                 200                 205

Ile Glu Asn Glu Leu Ser Tyr Asp Tyr Leu Val Tyr Ala Val Gly Ala
    210                 215                 220

Thr Val Asn Thr Phe Gly Ile Pro Gly Ile Pro Glu Tyr Ala Ser Tyr
225                 230                 235                 240

Leu Lys Glu Ala Asn Asp Ala Thr Ala Val Arg Gln Lys Leu Phe Asn
                245                 250                 255

Gln Ile Glu Ala Ser Arg Leu Leu Pro Lys Asp Ser Glu Asp Arg Lys
            260                 265                 270

Arg Leu Leu Ser Phe Val Val Cys Gly Gly Pro Thr Gly Val Glu
            275                 280                 285

Leu Ala Ala Glu Ile Lys Asp Tyr Ile Asp Gln Asp Leu Cys Lys Phe

```
             290                 295                 300
Ile Pro Gly Ile Glu Lys Glu Met Gln Val Thr Leu Ile Glu Ala Gln
305                 310                 315                 320

His Asn Val Leu Ser Met Phe His Pro Lys Leu Ile Glu Tyr Thr Lys
                325                 330                 335

Glu Val Phe Lys Gln Gln Asn Leu His Leu Gln Val Asp Thr Met Val
                340                 345                 350

Lys Lys Val Asp Asp Lys Asn Val Tyr Ala Thr Tyr Arg His Pro Asp
                355                 360                 365

Gly Lys Thr Glu Asp Met Val Ile Pro Tyr Gly Thr Leu Val Trp Ala
            370                 375                 380

Gly Gly Asn Ala Gln Arg Lys Leu Thr Arg Asp Leu Ser Ser Lys Ile
385                 390                 395                 400

Ile Glu Gln Lys Thr Ala Arg Arg Gly Leu Leu Val Asp Glu Tyr Leu
                405                 410                 415

Lys Leu Asp Gly Asp Asp Ser Ile Tyr Ala Ile Gly Asp Cys Thr Phe
                420                 425                 430

Thr Pro Asn Pro Pro Thr Ala Gln Val Ala His Gln Gln Gly Glu Tyr
            435                 440                 445

Leu Gly Glu His Phe Asn Lys Leu Ala Lys Ile Asp Glu Leu Asn Tyr
            450                 455                 460

Leu Ile Thr Asn Ser Thr Asp Asp Ser Thr Lys Tyr Ser Lys Arg Leu
465                 470                 475                 480

Glu Arg Ala Glu Lys Ala Ile Lys Pro Phe Glu Tyr Asp His Gln Gly
                485                 490                 495

Ala Leu Ala Tyr Val Gly Ser Glu Arg Ala Val Ala Asp Leu His Trp
            500                 505                 510

Gly Ser Trp Ser Thr Val Ala Leu Gly Gly Thr Met Thr Phe Phe Phe
            515                 520                 525

Trp Arg Thr Ala Tyr Val Ser Met Leu Leu Ser Ile Arg Asn Lys Ile
            530                 535                 540

Leu Val Val Thr Asp Trp Val Lys Val Ala Ile Phe Gly Arg Asp Cys
545                 550                 555                 560

Ser Gln Glu

<210> SEQ ID NO 17
<211> LENGTH: 331
<212> TYPE: PRT
<213> ORGANISM: Leuconostoc mesenteroides

<400> SEQUENCE: 17

Met Lys Ile Phe Ala Tyr Gly Ile Arg Asp Asp Glu Lys Pro Ser Leu
1               5                   10                  15

Glu Glu Trp Lys Ala Ala Asn Pro Glu Ile Glu Val Asp Tyr Thr Gln
            20                  25                  30

Glu Leu Leu Thr Pro Glu Thr Val Lys Leu Ala Glu Gly Ser Asp Ser
        35                  40                  45

Ala Val Val Tyr Gln Gln Leu Asp Tyr Thr Arg Glu Thr Leu Thr Ala
    50                  55                  60

Leu Ala Asn Val Gly Val Thr Asn Leu Ser Leu Arg Asn Val Gly Thr
65                  70                  75                  80

Asp Asn Ile Asp Phe Asp Ala Ala Arg Glu Phe Asn Phe Asn Ile Ser
                85                  90                  95

Asn Val Pro Val Tyr Ser Pro Asn Ala Ile Ala Glu His Ser Met Ile
```

```
                    100                 105                 110
        Gln Leu Ser Arg Leu Leu Arg Arg Thr Lys Ala Leu Asp Ala Lys Ile
                        115                 120                 125

Ala Lys His Asp Leu Arg Trp Ala Pro Thr Ile Gly Arg Glu Met Arg
            130                 135                 140

Met Gln Thr Val Gly Val Ile Gly Thr Gly His Ile Gly Arg Val Ala
        145                 150                 155                 160

Ile Asn Ile Leu Lys Gly Phe Gly Ala Lys Val Ile Ala Tyr Asp Lys
                        165                 170                 175

Tyr Pro Asn Ala Glu Leu Gln Ala Glu Gly Leu Tyr Val Asp Thr Leu
                    180                 185                 190

Asp Glu Leu Tyr Ala Gln Ala Asp Ala Ile Ser Leu Tyr Val Pro Gly
                    195                 200                 205

Val Pro Glu Asn His His Leu Ile Asn Ala Glu Ala Ile Ala Lys Met
                    210                 215                 220

Lys Asp Gly Val Val Ile Met Asn Ala Ala Arg Gly Asn Leu Met Asp
        225                 230                 235                 240

Ile Asp Ala Ile Ile Asp Gly Leu Asn Ser Gly Lys Ile Ser Asp Phe
                        245                 250                 255

Gly Met Asp Val Tyr Glu Asn Glu Val Gly Leu Phe Asn Glu Asp Trp
                    260                 265                 270

Ser Gly Lys Glu Phe Pro Asp Ala Lys Ile Ala Asp Leu Ile Ser Arg
                    275                 280                 285

Glu Asn Val Leu Val Thr Pro His Thr Ala Phe Tyr Thr Thr Lys Ala
                    290                 295                 300

Val Leu Glu Met Val His Gln Ser Phe Asp Ala Ala Val Ala Phe Ala
        305                 310                 315                 320

Lys Gly Glu Lys Pro Ala Ile Ala Val Glu Tyr
                        325                 330

<210> SEQ ID NO 18
<211> LENGTH: 332
<212> TYPE: PRT
<213> ORGANISM: Lactobacillus plantarum

<400> SEQUENCE: 18

Met Lys Ile Ile Ala Tyr Ala Val Arg Asp Asp Glu Arg Pro Phe Phe
        1               5                   10                  15

Asp Thr Trp Met Lys Glu Asn Pro Asp Val Glu Val Lys Leu Val Pro
                    20                  25                  30

Glu Leu Leu Thr Glu Asp Asn Val Asp Leu Ala Lys Gly Phe Asp Gly
                    35                  40                  45

Ala Asp Val Tyr Gln Gln Lys Asp Tyr Thr Ala Glu Val Leu Asn Lys
            50                  55                  60

Leu Ala Asp Glu Gly Val Lys Asn Ile Ser Leu Arg Asn Val Gly Val
        65                  70                  75                  80

Asp Asn Leu Asp Val Pro Thr Val Lys Ala Arg Gly Leu Asn Ile Ser
                        85                  90                  95

Asn Val Pro Ala Tyr Ser Pro Asn Ala Ile Ala Glu Leu Ser Val Thr
                    100                 105                 110

Gln Leu Met Gln Leu Leu Arg Gln Thr Pro Leu Phe Asn Lys Lys Leu
                    115                 120                 125

Ala Lys Gln Asp Phe Arg Trp Ala Pro Asp Ile Ala Lys Glu Leu Asn
            130                 135                 140
```

```
Thr Met Thr Val Gly Val Ile Gly Thr Gly Arg Ile Gly Arg Ala Ala
145                 150                 155                 160

Ile Asp Ile Phe Lys Gly Phe Gly Ala Lys Val Ile Gly Tyr Asp Val
                165                 170                 175

Tyr Arg Asn Ala Glu Leu Glu Lys Glu Gly Met Tyr Val Asp Thr Leu
            180                 185                 190

Asp Glu Leu Tyr Ala Gln Ala Asp Val Ile Thr Leu His Val Pro Ala
        195                 200                 205

Leu Lys Asp Asn Tyr His Met Leu Asn Ala Asp Ala Phe Ser Lys Met
    210                 215                 220

Lys Asp Gly Ala Tyr Ile Leu Asn Phe Ala Arg Gly Thr Leu Ile Asp
225                 230                 235                 240

Ser Glu Asp Leu Ile Lys Ala Leu Asp Ser Gly Lys Val Ala Gly Ala
                245                 250                 255

Ala Leu Asp Thr Tyr Glu Tyr Glu Thr Lys Ile Phe Asn Lys Asp Leu
                260                 265                 270

Glu Gly Gln Thr Ile Asp Asp Lys Val Phe Met Asn Leu Phe Asn Arg
            275                 280                 285

Asp Asn Val Leu Ile Thr Pro His Thr Ala Phe Tyr Thr Glu Thr Ala
        290                 295                 300

Val His Asn Met Val His Val Ser Met Asn Ser Asn Lys Gln Phe Ile
305                 310                 315                 320

Glu Thr Gly Lys Ala Asp Thr Gln Val Lys Phe Asp
                325                 330

<210> SEQ ID NO 19
<211> LENGTH: 329
<212> TYPE: PRT
<213> ORGANISM: Pseudomonas aeruginosa

<400> SEQUENCE: 19

Met Arg Ile Leu Phe Ser Ser Gln Ala Tyr Asp Ser Glu Ser Phe
1               5                   10                  15

Gln Ala Ser Asn His Arg His Gly Phe Glu Leu His Phe Gln Gln Ala
                20                  25                  30

His Leu Gln Ala Asp Thr Ala Val Leu Ala Gln Gly Phe Glu Val Val
            35                  40                  45

Cys Ala Phe Val Asn Asp Asp Leu Ser Arg Pro Val Leu Glu Arg Leu
        50                  55                  60

Ala Ala Gly Gly Thr Arg Leu Val Ala Leu Arg Ser Ala Gly Tyr Asn
65                  70                  75                  80

His Val Asp Leu Ala Ala Ala Glu Ala Leu Gly Leu Pro Val Val His
                85                  90                  95

Val Pro Ala Tyr Ser Pro His Ala Val Ala Glu His Ala Val Gly Leu
                100                 105                 110

Ile Leu Thr Leu Asn Arg Arg Leu His Arg Ala Tyr Asn Arg Thr Arg
                115                 120                 125

Glu Gly Asp Phe Ser Leu His Gly Leu Thr Gly Phe Asp Leu His Gly
            130                 135                 140

Lys Arg Val Gly Val Ile Gly Thr Gly Gln Ile Gly Glu Thr Phe Ala
145                 150                 155                 160

Arg Ile Met Ala Gly Phe Gly Cys Glu Leu Leu Ala Tyr Asp Pro Tyr
                165                 170                 175

Pro Asn Pro Arg Ile Gln Ala Leu Gly Gly Arg Tyr Leu Ala Leu Asp
            180                 185                 190
```

```
Ala Leu Leu Ala Glu Ser Asp Ile Val Ser Leu His Cys Pro Leu Thr
            195                 200                 205

Ala Asp Thr Arg His Leu Ile Asp Ala Gln Arg Leu Ala Thr Met Lys
210                 215                 220

Pro Gly Ala Met Leu Ile Asn Thr Gly Arg Gly Ala Leu Val Asn Ala
225                 230                 235                 240

Ala Ala Leu Ile Glu Ala Leu Lys Ser Gly Gln Leu Gly Tyr Leu Gly
            245                 250                 255

Leu Asp Val Tyr Glu Glu Ala Asp Ile Phe Phe Glu Asp Arg Ser
            260                 265                 270

Asp Gln Pro Leu Gln Asp Val Leu Ala Arg Leu Leu Ser Phe Pro
            275                 280                 285

Asn Val Val Thr Ala His Gln Ala Phe Leu Thr Arg Glu Ala Leu
290                 295                 300

Ala Ala Ile Ala Asp Thr Thr Leu Asp Asn Ile Ala Ala Trp Gln Asp
305                 310                 315                 320

Gly Thr Pro Arg Asn Arg Val Arg Ala
                325

<210> SEQ ID NO 20
<211> LENGTH: 335
<212> TYPE: PRT
<213> ORGANISM: Fusobacterium nucleatum

<400> SEQUENCE: 20

Met Gln Lys Thr Lys Ile Ile Phe Phe Asp Ile Lys Asp Tyr Asp Lys
1               5                   10                  15

Glu Phe Phe Lys Lys Tyr Gly Ala Asp Tyr Asn Phe Glu Met Thr Phe
            20                  25                  30

Leu Lys Val Arg Leu Thr Glu Thr Ala Asn Leu Thr Lys Gly Tyr
        35                  40                  45

Asp Val Val Cys Gly Phe Ala Asn Asp Asn Ile Asn Lys Glu Thr Ile
50                  55                  60

Asp Ile Met Ala Glu Asn Gly Ile Lys Leu Leu Ala Met Arg Cys Ala
65                  70                  75                  80

Gly Phe Asn Asn Val Ser Leu Lys Asp Val Asn Glu Arg Phe Lys Val
                85                  90                  95

Val Arg Val Pro Ala Tyr Ser Pro His Ala Ile Ala Glu Tyr Thr Val
            100                 105                 110

Gly Leu Ile Leu Ala Val Asn Arg Lys Ile Asn Lys Ala Tyr Val Arg
        115                 120                 125

Thr Arg Glu Gly Asn Phe Ser Ile Asn Gly Leu Met Gly Ile Asp Leu
130                 135                 140

Tyr Glu Lys Thr Ala Gly Ile Ile Gly Thr Gly Lys Ile Gly Gln Ile
145                 150                 155                 160

Leu Ile Lys Ile Leu Arg Gly Phe Asp Met Lys Val Ile Ala Tyr Asp
                165                 170                 175

Leu Phe Pro Asn Gln Lys Val Ala Asp Glu Leu Gly Phe Glu Tyr Val
            180                 185                 190

Ser Leu Asp Glu Leu Tyr Ala Asn Ser Asp Ile Ile Ser Leu Asn Cys
        195                 200                 205

Pro Leu Thr Lys Asp Thr Lys Tyr Met Ile Asn Arg Arg Ser Met Leu
210                 215                 220

Lys Met Lys Asp Gly Val Ile Leu Val Asn Thr Gly Arg Gly Met Leu
```

```
225                 230                 235                 240

Ile Asp Ser Ala Asp Leu Val Glu Ala Leu Lys Asp Lys Ile Gly
                245                 250                 255

Ala Val Ala Leu Asp Val Tyr Glu Glu Glu Asn Tyr Phe Phe Glu
                260                 265                 270

Asp Lys Ser Thr Gln Val Ile Glu Asp Ile Leu Gly Arg Leu Leu
                275                 280                 285

Ser Phe Tyr Asn Val Leu Ile Thr Ser His Gln Ala Tyr Phe Thr Lys
            290                 295                 300

Glu Ala Val Gly Ala Ile Thr Val Thr Thr Leu Asn Asn Ile Lys Asp
305                 310                 315                 320

Phe Val Glu Gly Arg Pro Leu Val Asn Glu Val Pro Gln Asn Gln
                325                 330                 335
```

<210> SEQ ID NO 21
<211> LENGTH: 331
<212> TYPE: PRT
<213> ORGANISM: Pediococcus acidilactici

<400> SEQUENCE: 21

```
Met Lys Ile Ile Ala Tyr Gly Ile Arg Asp Asp Glu Lys Pro Tyr Leu
1               5                   10                  15

Asp Glu Trp Val Thr Lys Asn His Ile Glu Val Lys Ala Val Pro Asp
                20                  25                  30

Leu Leu Asp Ser Ser Asn Ile Asp Leu Ala Lys Asp Tyr Asp Gly Val
            35                  40                  45

Val Ala Tyr Gln Gln Lys Pro Tyr Thr Ala Asp Leu Phe Asp Lys Met
50                  55                  60

His Glu Phe Gly Ile His Ala Phe Ser Leu Arg Asn Val Gly Val Asp
65                  70                  75                  80

Asn Val Pro Ala Asp Ala Leu Lys Lys Asn Asp Ile Lys Ile Ser Asn
                85                  90                  95

Val Pro Ala Tyr Ser Pro Arg Ala Ile Ala Glu Leu Ser Val Thr Gln
            100                 105                 110

Leu Leu Ala Leu Leu Arg Lys Ile Pro Glu Phe Glu Tyr Lys Met Ala
            115                 120                 125

His Gly Asp Tyr Arg Trp Glu Pro Asp Ile Gly Leu Glu Leu Asn Gln
        130                 135                 140

Met Thr Val Gly Val Ile Gly Thr Gly Arg Ile Gly Arg Ala Ala Ile
145                 150                 155                 160

Asp Ile Phe Lys Gly Phe Gly Ala Lys Val Ile Ala Tyr Asp Val Phe
                165                 170                 175

Arg Asn Pro Ala Leu Glu Lys Glu Gly Met Tyr Val Asp Thr Leu Glu
            180                 185                 190

Glu Leu Tyr Gln Gln Ala Asn Val Ile Thr Leu His Val Pro Ala Leu
        195                 200                 205

Lys Asp Asn Tyr His Met Leu Asp Glu Lys Ala Phe Gly Gln Met Gln
210                 215                 220

Asp Gly Thr Phe Ile Leu Asn Phe Ala Arg Gly Thr Leu Ile Asp Thr
225                 230                 235                 240

Pro Ala Leu Leu Lys Ala Leu Asp Ser Gly Lys Val Ala Gly Ala Ala
                245                 250                 255

Leu Asp Thr Tyr Glu Asn Glu Val Gly Ile Phe Asp Val Asp His Gly
            260                 265                 270
```

```
Asp Gln Pro Ile Asp Asp Pro Val Phe Asn Asp Leu Met Ser Arg Arg
            275                 280                 285

Asn Val Met Ile Thr Pro His Ala Ala Phe Tyr Thr Arg Pro Ala Val
    290                 295                 300

Lys Asn Met Val Gln Ile Ala Leu Asp Asn Asn Arg Asp Leu Ile Glu
305                 310                 315                 320

Lys Asn Ser Ser Lys Asn Glu Val Lys Phe Asp
                325                 330

<210> SEQ ID NO 22
<211> LENGTH: 332
<212> TYPE: PRT
<213> ORGANISM: Lactobacillus plantarum

<400> SEQUENCE: 22

Met Lys Ile Ile Ala Tyr Ala Val Arg Asp Asp Glu Arg Pro Phe Phe
1               5                   10                  15

Asp Thr Trp Met Lys Glu Asn Pro Asp Val Glu Val Lys Leu Val Pro
            20                  25                  30

Glu Leu Leu Thr Glu Asp Asn Val Asp Leu Ala Lys Gly Phe Asp Gly
        35                  40                  45

Ala Asp Val Tyr Gln Gln Lys Asp Tyr Thr Ala Glu Val Leu Asn Lys
    50                  55                  60

Leu Ala Asp Glu Gly Val Lys Asn Ile Ser Leu Arg Asn Val Gly Val
65                  70                  75                  80

Asp Asn Leu Asp Val Pro Thr Val Lys Ala Arg Gly Leu Asn Ile Ser
                85                  90                  95

Asn Val Pro Ala Tyr Ser Pro Asn Ala Ile Ala Glu Leu Ser Val Thr
            100                 105                 110

Gln Leu Met Gln Leu Leu Arg Gln Thr Pro Met Phe Asn Lys Lys Leu
        115                 120                 125

Ala Lys Gln Asp Phe Arg Trp Ala Pro Asn Ile Ala Lys Glu Leu Asn
    130                 135                 140

Thr Met Thr Val Gly Val Ile Gly Thr Gly Arg Ile Gly Arg Ala Ala
145                 150                 155                 160

Ile Asp Ile Phe Lys Gly Phe Gly Ala Lys Val Ile Gly Tyr Asp Val
                165                 170                 175

Tyr Arg Asn Ala Glu Leu Glu Lys Glu Gly Met Tyr Val Asp Thr Leu
            180                 185                 190

Asp Glu Leu Tyr Ala Gln Ala Asp Val Ile Thr Leu His Val Pro Ala
        195                 200                 205

Leu Lys Asp Asn Tyr His Met Leu Asn Ala Asp Ala Phe Ser Lys Met
    210                 215                 220

Lys Asp Gly Ala Tyr Ile Leu Asn Phe Ala Arg Gly Thr Leu Ile Asp
225                 230                 235                 240

Ser Glu Asp Leu Ile Lys Ala Leu Asp Ser Gly Lys Val Ala Gly Ala
                245                 250                 255

Ala Leu Asp Thr Tyr Glu Tyr Glu Thr Lys Ile Phe Asn Lys Asp Leu
            260                 265                 270

Glu Gly Gln Thr Ile Asp Asp Lys Val Phe Met Asn Leu Phe Asn Arg
        275                 280                 285

Asp Asn Val Leu Ile Thr Pro His Thr Ala Phe Tyr Thr Glu Thr Ala
    290                 295                 300

Val His Asn Met Val His Val Ser Met Asn Ser Asn Lys Gln Phe Ile
305                 310                 315                 320
```

Glu Thr Gly Lys Ala Asp Thr Gln Val Lys Phe Asp
                325                 330

<210> SEQ ID NO 23
<211> LENGTH: 331
<212> TYPE: PRT
<213> ORGANISM: Leuconostoc carnosum

<400> SEQUENCE: 23

Met Lys Ile Phe Ala Tyr Gly Ile Arg Asp Glu Lys Pro Ser Leu
1               5                   10                  15

Glu Asp Trp Lys Ser Thr His Pro Glu Val Glu Val Asp Tyr Thr Gln
                20                  25                  30

Glu Leu Leu Thr Pro Glu Thr Ala Lys Leu Ala Ser Gly Ser Asp Ser
                35                  40                  45

Ala Val Val Tyr Gln Gln Leu Asp Tyr Thr Arg Glu Thr Leu Thr Ala
            50                  55                  60

Leu Ser Glu Val Gly Val Thr Asn Leu Ser Leu Arg Asn Val Gly Thr
65                  70                  75                  80

Asp Asn Ile Asp Phe Glu Ala Ala Lys Glu Leu Asn Phe Asn Ile Ser
                85                  90                  95

Asn Val Pro Val Tyr Ser Pro Asn Ala Ile Ala Glu His Ser Met Ile
            100                 105                 110

Gln Leu Ser Arg Leu Leu Arg Arg Thr Lys Ala Leu Asp Ala Lys Ile
            115                 120                 125

Ala Lys His Asp Leu Arg Trp Ala Pro Thr Ile Gly Arg Glu Val Arg
        130                 135                 140

Met Gln Thr Val Gly Val Ile Gly Thr Gly Asn Ile Gly Arg Val Ala
145                 150                 155                 160

Ile Lys Ile Leu Gln Gly Phe Gly Ala Lys Val Val Ala Tyr Asp Lys
                165                 170                 175

Phe Pro Asn Ala Glu Ile Ala Ala Gln Gly Leu Tyr Val Asp Ser Leu
            180                 185                 190

Asp Glu Leu Tyr Ala Gln Ala Asp Ala Val Ala Leu Phe Val Pro Gly
        195                 200                 205

Val Pro Glu Asn His His Met Ile Asp Ala Ser Ala Ile Ala Lys Met
        210                 215                 220

Lys Asp Gly Val Ile Ile Met Asn Ala Ser Arg Gly Asn Leu Met Ala
225                 230                 235                 240

Ile Asp Asp Ile Ile Asp Gly Leu Asn Ser Gly Lys Ile Ser Asp Phe
                245                 250                 255

Gly Met Asp Val Tyr Glu Glu Glu Val Gly Leu Phe Asn Glu Asp Trp
            260                 265                 270

Ser Asn Lys Glu Phe Pro Asp Ser Lys Ile Ala Asp Leu Ile Ser Arg
        275                 280                 285

Glu Asn Val Leu Val Thr Pro His Thr Ala Phe Tyr Thr Thr Lys Ala
        290                 295                 300

Val Leu Glu Met Val His Gln Ser Met Asp Ala Ala Val Ala Phe Ala
305                 310                 315                 320

Asn Gly Glu Thr Pro Ser Ile Ala Val Lys Tyr
                325                 330